(12) United States Patent
Musallam

(10) Patent No.: US 12,179,021 B2
(45) Date of Patent: Dec. 31, 2024

(54) NEUROMODULATION FOR TREATMENT OF BRAIN AND EYE STROKES AND/OR ACUTE DYSREGULATED REDUCED CEREBRAL OR OCULAR BLOOD FLOW

(71) Applicant: Ismail Mohammed Yousif Musallam, Jerusalem (IL)

(72) Inventor: Ismail Mohammed Yousif Musallam, Jerusalem (IL)

( * ) Notice: Subject to any disclaimer, the term of this patent is extended or adjusted under 35 U.S.C. 154(b) by 0 days.

(21) Appl. No.: 18/403,798

(22) Filed: Jan. 4, 2024

(65) Prior Publication Data

US 2024/0173548 A1     May 30, 2024

Related U.S. Application Data

(62) Division of application No. 16/932,773, filed on Jul. 19, 2020, now Pat. No. 11,911,620.

(Continued)

(51) Int. Cl.
*A61N 1/04*     (2006.01)
*A61K 31/045*     (2006.01)
(Continued)

(52) U.S. Cl.
CPC ........ *A61N 1/36046* (2013.01); *A61K 31/045* (2013.01); *A61K 31/375* (2013.01);
(Continued)

(58) Field of Classification Search
CPC ................ A61K 31/045; A61K 31/375; A61N 1/0456; A61N 1/36025; A61N 1/36046;
(Continued)

(56) References Cited

U.S. PATENT DOCUMENTS

| | | |
|---|---|---|
| 2011/0218589 A1 | 9/2011 | Degiorgio et al. |
| 2014/0135886 A1 | 5/2014 | Cook et al. |
| 2014/0142669 A1 | 5/2014 | Cook et al. |

*Primary Examiner* — Mark D Remaly

(57) ABSTRACT

Disclosed are devices, systems and methods for non-invasive neuromodulation system for prompt treatment of cerebral and/or ocular strokes caused by acute dysregulated reduced cerebral blood flow (CBF) and/or ocular blood flow (OBF) by up regulation of trigeminovascular system (TVS), and trigeminal autonomic brain reflexes (TABRs) through stimulation of ophthalmic nerve. Additionally or alternatively, the subject's sympathetic nervous system (SNS) is down regulated centrally by intravenous administration of pharmacological dose of ascorbic acid. The site of stimulation of ophthalmic nerve includes but not limited to nasal vestibule, nasal bridge, and forehead and upper eyelid. In some embodiments, the devices are handheld, portable with nose supported, having one or more intra-nasal or extra-nasal application heads. The signal can include vibration, chemical, ultrasonic, optical, electrical, hybrid electro-optical or combination of two or more of these types of stimuli. The subject's TVS and autonomic nervous system (ANS) are modulated in a manner that is effective to treat the subject for cerebral and ocular strokes. The invention, in some embodiments thereof, relates to a method for decreasing vascular resistance, enhancing vasodilatation in cerebral arteries, leptomeningeal collaterals and ophthalmic artery by the release of Vasoactive intestinal peptide (VIP), substance P and CGRP thereof increasing cerebral and/or OBF to the brain and the eye in subject's with acute dysregulated, reduced cerebral and/or OBF. The invention, in some embodiments thereof, is also relates to upregulation of TVS in a manner that is effective to induce acute development of leptomeningeal collateral circulation sufficient to ameliorate the ischemic effect of occluded cerebral artery, enhances successful recanalization, decreases the infarction volume and improves brain functional recovery without hemorrhagic transformation. In some embodiments TVS and ANS are also modulated in a manner that induce an acute increase in choroidal blood flow sufficient to ameliorate the ischemic effect of occluded artery until spontaneous recanalization of the occluded artery is accomplished. The invention is related to targeting the affected side via ipsilateral ONS without inducing intracerebral vascular steal phenomenon. The invention, in some embodiments thereof, is also relates to the methods for improving delivery of oxygen, glucose, anticoagulants, hormones, humoral mediators, growth factors and pharmacological agents to the targeted ischemic tissues of the brain, retina and optic nerve. The methods of the invention, when combined with r-tPA treatment and/or endovascular recanalization increases window time of treatment of stroke, enhance the efficacy of treatment and reduce its side effects. The methods of the invention, in some embodiments thereof, include priming of the brain, retina (Continued)

and/or optic nerve thereof to enhance the efficacy of cell transplantation therapy after exposure to stroke. Methods of the invention, in some embodiments thereof, may also include monitoring the subject for prophylactic treatment. The cerebral/and or OBF of subjects who had received neuromodulation treatment may also be monitored for re-treatment.

17 Claims, 17 Drawing Sheets

Related U.S. Application Data

(60) Provisional application No. 62/876,791, filed on Jul. 22, 2019.

(51) Int. Cl.
  *A61K 31/375* (2006.01)
  *A61N 1/36* (2006.01)
  *A61N 5/06* (2006.01)
  *A61N 7/00* (2006.01)

(52) U.S. Cl.
  CPC ....... *A61N 1/0456* (2013.01); *A61N 1/36025* (2013.01); *A61N 5/062* (2013.01); *A61N 5/0622* (2013.01); *A61N 7/00* (2013.01); *A61N 2007/0026* (2013.01)

(58) Field of Classification Search
  CPC .... A61N 2005/0626; A61N 2005/0662; A61N 2007/0026; A61N 5/062; A61N 5/0622; A61N 7/00
  See application file for complete search history.

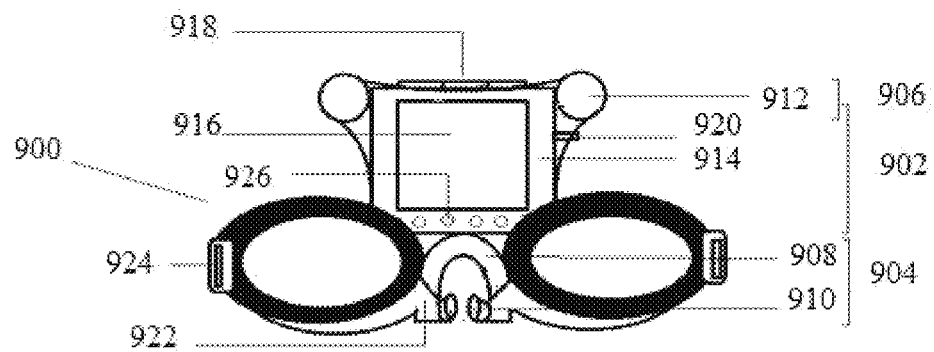
FIG. 9A
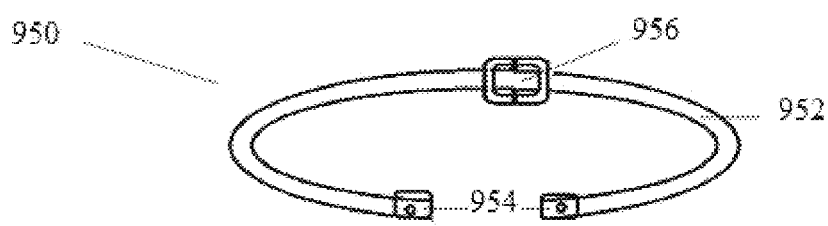
FIG. 9B
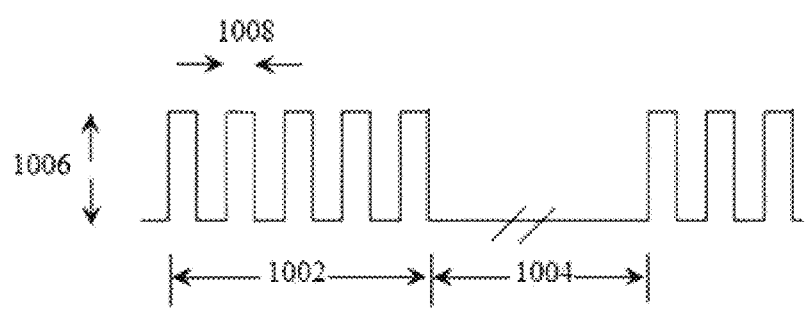
FIG 10.A

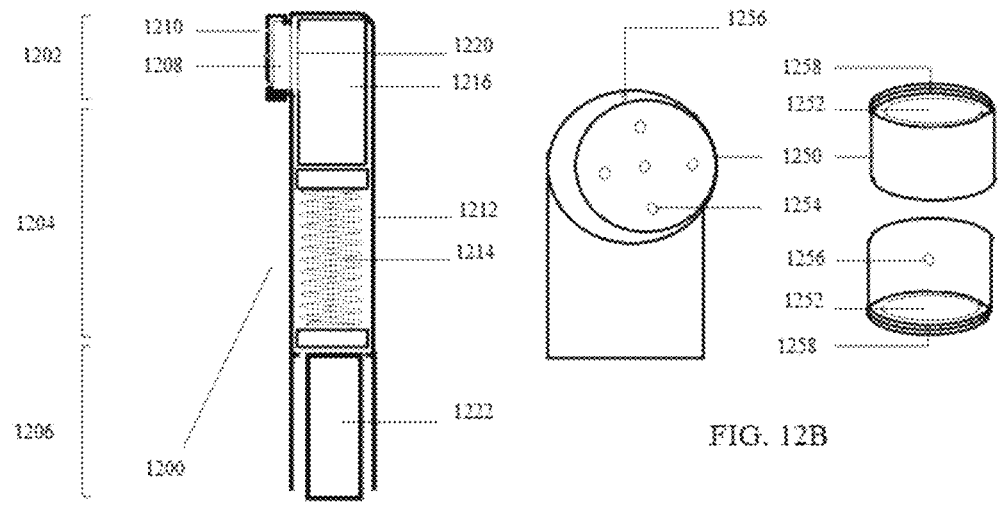
FIG. 12A
FIG. 12B
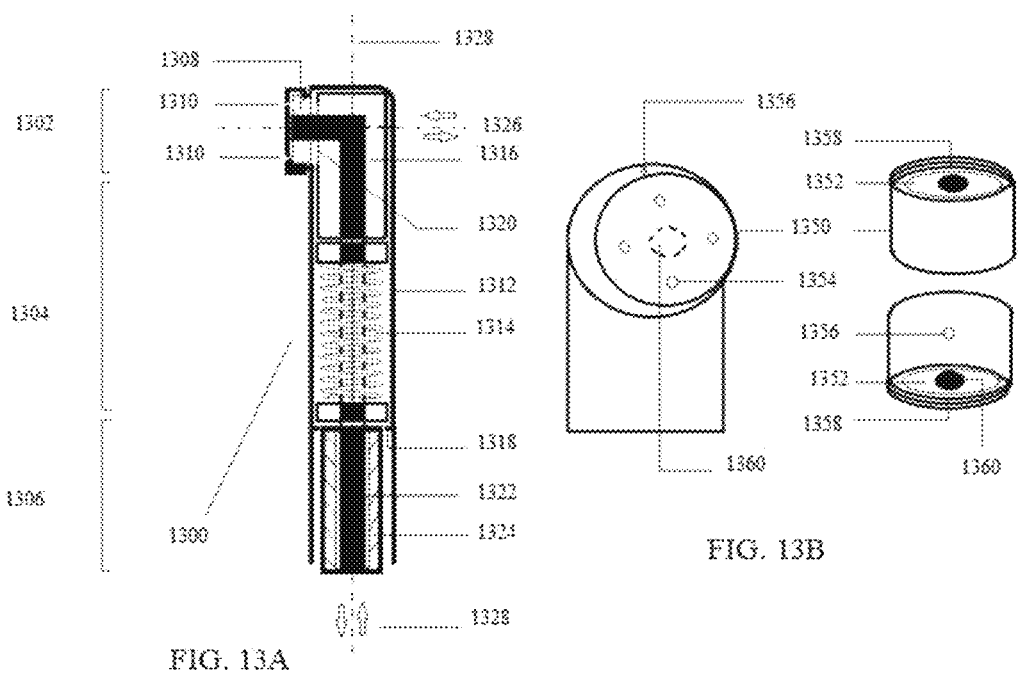
FIG. 13A
FIG. 13B

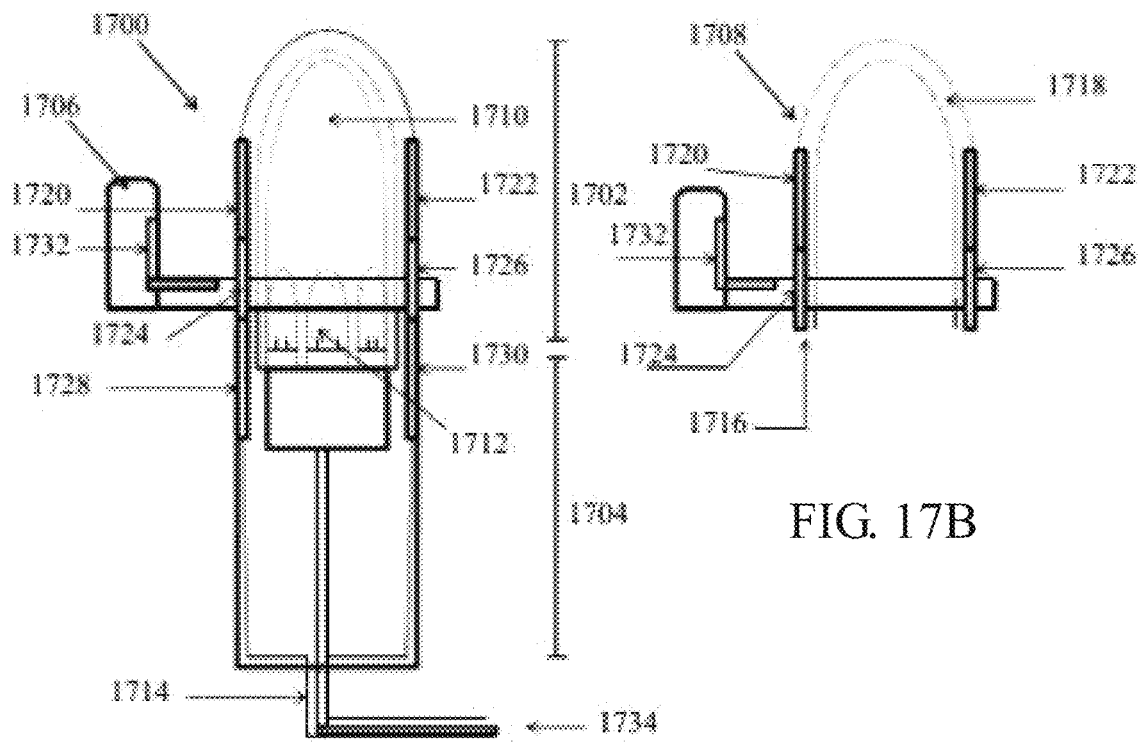
FIG. 17A
FIG. 17B
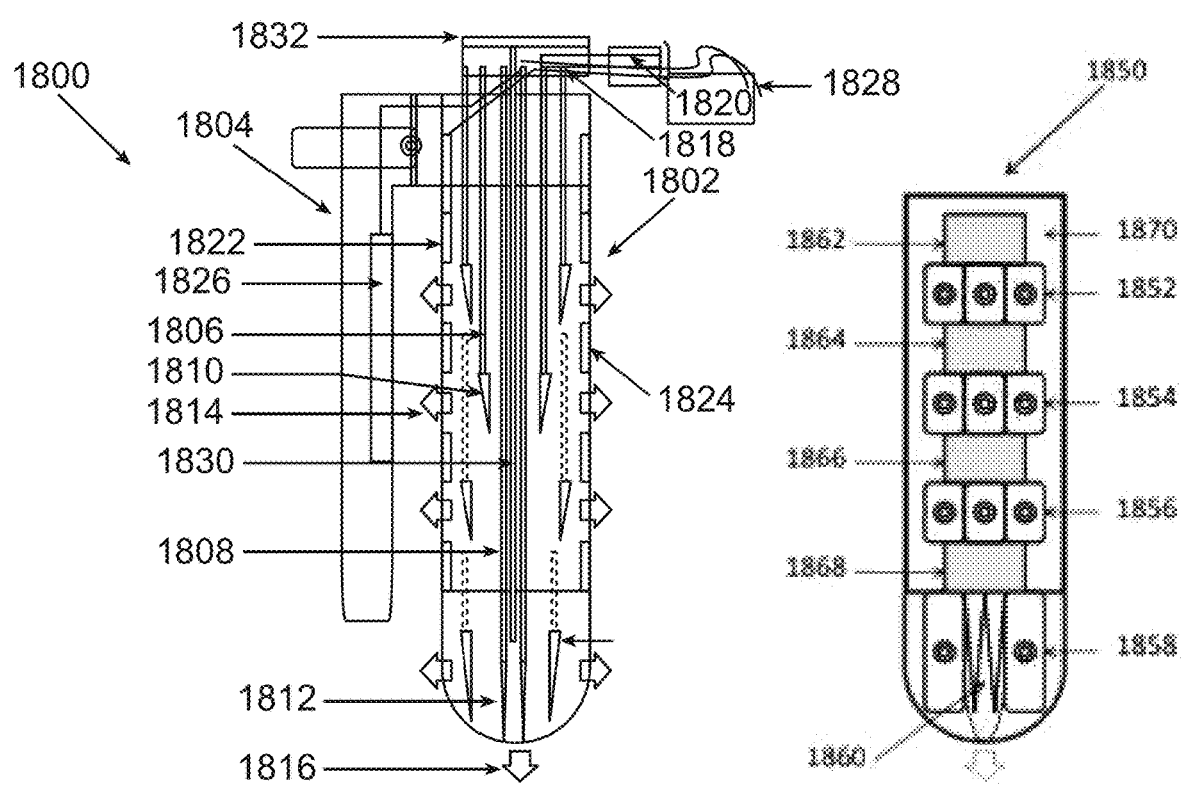
FIG. 18A
FIG. 18B

NEUROMODULATION FOR TREATMENT OF BRAIN AND EYE STROKES AND/OR ACUTE DYSREGULATED REDUCED CEREBRAL OR OCULAR BLOOD FLOW

The present invention, in some embodiments thereof, relates to a non-invasive method and/or device for treatment of acute dysregulated reduced cerebral and/or ocular blood flow, more particularly, but not exclusively, to a method and/or device for treatment of brain and eye strokes and/or transient ischemic attacks via application of an effective amount of ophthalmic nerve stimulation alone and/or in combination with intravenous administration of pharmacological doses of ascorbic acid as an antioxidant/sympatholytic agents. In some embodiments trigeminovascular system (TVS) and autonomic nervous system (ANS) are modulated in a manner that is effective to induce acute development of leptomeningeal collateral circulation sufficient to ameliorate the ischemic effect of occluded cerebral artery, enhances successful recanalization, decreases infarction volume and improving functional recovery, without hemorrhagic transformation. In some embodiments TVS and ANS are also modulated in a manner that induce an acute increase in choroidal blood flow sufficient to ameliorate the ischemic effect of occluded artery until spontaneous recanalization of the occluded artery is accomplished. The inventive method described here can be used along with other known therapeutic agents for treatment of clinically developed brain and eye strokes. The inventive method described here can also be used for treatment of sensory, motor and cognitive deficits induced by stroke during rehabilitative stage.

FIELD OF THE INVENTION

The present invention generally relates to methods systems and devices. More specifically, the invention relates to the use of vibrotactile, chemical, ultrasonic, electrical, optical, and/or hybrid electro-optical stimulation of ophthalmic nerve for treating acute cerebral or ocular strokes combined with intravenous administration of pharmacological dose of ascorbic acid as an antioxidant sympatholytic agents.

BACKGROUND OF THE INVENTION

In the present invention, ophthalmic nerve stimulation (ONS) combined with intravenous administration of pharmacological doses of ascorbic acid as an antioxidant sympatholytic agents is used to abort, treat or manage stroke and/or transient ischemic attacks and amaurosis fugax. A stroke is a medical condition in which poor blood flow to the brain results in cell death. There are two main types of strokes: ischemic, due to lack of blood flow, and hemorrhagic, due to bleeding. Both result in the acute loss of brain function due to loss of normal blood supply to the brain, brainstem, spinal cord, retina or optic nerve.

A thrombotic stroke occurs when a blood clot (thrombus) forms in one of the brain's arteries on top of atherosclerotic plaque. Less commonly, the thrombus may develop at the site of a vasospasm associated with migraine attack. An embolic stroke occurs when a blood clot or other detached atheromatous plaque is transported through the blood stream to lodge in an artery of the brain, retina and optic nerve. About half to two-thirds of all strokes are thrombotic strokes. Ischemic stroke occurs in 87% of stroke patients. In contrast, hemorrhagic strokes occur in 13% of stroke patients, who may be treated by neurosurgery. Hemorrhagic strokes include bleeding within the brain (intracerebral hemorrhage) and bleeding between the inner and outer layers of the tissue covering the brain (subarachnoid hemorrhage).

Ischemic brain injury (IBI) is one of the most common causes of mortality and morbidity in the world. Ischemic brain injury is accompanied by several side effects, including brain oedema, destruction of blood-brain barrier (BBB), inflammation and induction of oxidative stress. Oxidative stress in turn leads to oedema and more destruction of BBB which causes additional brain damage. Reperfusion with thrombolytic recombinant tissue plasminogen activator (r-tPA) and endovascular therapy remain the only treatments proved to be safe and effective when given within 3-24 hr after ischemia onset. It has been shown that delayed use of r-tPA leads to hyper perfusion which results in the accumulation of free radicals and the up-regulation of matrix metalloproteinases (MMPs) including MMP-9 and these events lead to more injuries to the brain parenchyma.

Signs and symptoms of a stroke may include an inability to move or feel on one side of the body, problems understanding or speaking, dizziness, or loss of vision to one side. Signs and symptoms often appear soon after the stroke has occurred. If symptoms last less than one or two hours it is known as a transient ischemic attack (TIA) or mini-stroke. A hemorrhagic stroke may also be associated with a severe headache.

A transient ischemic attack (TIA) is also caused by ischemia in the brain, spinal cord, retina or optic nerve. TIAs share the same underlying etiology as ischemic strokes and produce the same symptoms, such as contralateral paralysis, sudden weakness or numbness, dimming or loss of vision, aphasia, slurred speech and mental confusion. Unlike a stroke, the symptoms of a TIA can resolve typically within a day, whereas the symptoms from a stroke can persist due to death of neural tissue (acute infarction).

Every year stroke is responsible for the death of 5.5 million people and account for approximately 9.7% of all deaths worldwide. It is the third-leading cause of death in the United States, with more than 140,000 people dying of stroke each year. The total cost of stroke to the United States is estimated at $43 billion per year.

Research efforts to find novel treatment strategies focus primarily on rescuing the ischemic penumbra, the viable tissue surrounding the nonviable infarct core. In the penumbra, blood flow is critically reduced but still suffices to sustain neuronal integrity for several hours. The delayed nature of cell death in the penumbra leaves a unique window of opportunity for therapeutic interventions. If adequate cerebral perfusion is re-established sufficiently fast, then penumbral tissue can be effectively saved. Therefore, penumbral reperfusion at the earliest possible time is the most critical factor in determining neurological outcome and in preventing mortality after stroke.

Currently, the only clinical treatment option to increase penumbral blood flow and, hence, to prevent the progression of ischemic brain damage are endovascular therapy and/or thrombolysis by local or systemic administration of r-tPA. A major drawback of r-tPA, however, is that it may be fatal if administered in patients with hemorrhagic stroke who present with similar symptoms as ischemic stroke patients. Hemorrhagic stroke, however, can be ruled out by advanced imaging techniques. The therapeutic window for r-tPA, extended from 3 to 4.5 hours after the onset of ischemia. As a result, less than 5% of all stroke patients are eligible for r-tPA thrombolysis according to current protocols. The remaining 95% may only hope for spontaneous reperfusion, which in most cases occurs too late to prevent penumbral cell death and, hence, fails to restore neurological function. Accordingly, novel strategies are required to prolong neuronal survival in the ischemic penumbra.

Background art includes

REFERENCES

Arbab, MA-R, Wiklund, L., Svendgaard, N. A. (1986) Origin and distribution of cerebral vascular innervation from superior cervical, trigeminal and spinal ganglia investigated with retrograde and anterograde WGA-HRP tracing in the rat. Neuroscience 19:695-708.

Arbab, MA-R, Delgado, T., Wiklund, L., Svendgaard, N. A. (1988) Brain stem terminations of the trigeminal and upper spinal ganglia innervation of the cerebrovascular system: WGA-HRP transganglionic study. J Cereb Blood Flow Metab 8:54-63.

Bornstein N M. Saver J L. Diener H C. et al. (2019) Sphenopalatine ganglion stimulation to augment cerebral blood flow: a randomized, sham-controlled trial. *Stroke;*

Campbell B C, Christensen S, Tress B M, Churilov L, Desmond P M, Parsons M W, Barber P A, Levi C R, Bladin C, Donnan G A, Davis S M. EPITHET Investigators (2013) Failure of collateral blood flow is associated with infarct growth in ischemic stroke. J Cereb Blood Flow Metab. 33:1168-1172

Chen Q, Espey M G, Krishna M C, Mitchell J B, Corpe C P, Buettner G R, Shacter E, Levine M. (2005) Pharmacologic ascorbic acid concentrations selectively kill cancer cells: action as a pro-drug to deliver hydrogen peroxide to tissues. Proc Natl Acad Sci USA. 20; 102(38): 13604-9.

Chen Q, Espey M G, Sun A Y, Lee J H, Krishna M C, Shacter E, Choyke P L, Pooput C, Kirk K L, Buettner G R, Levine M. Ascorbate in pharmacologic concentrations selectively generates ascorbate radical and hydrogen peroxide in extracellular fluid in vivo. Proc Natl Acad Sci USA. 2007 May 22; 104(21):8749-54. Epub 2007 May 14.

Dimitriadou, V., Buzzi, M. G., Theoharides, T. C., Moskowitz, M. A. (1992) Ultrastructural evidence for neurogenically mediated changes in blood vessels of the rat dura mater and tongue following antidromic trigeminal stimulation. Neuroscience 48:187-203

Edvinsson, L., Ekman, R., Jansen, I., Ottosson, A., Uddman, R. (1987) Peptide-containing nerve fibers in human cerebral arteries: immunohistochemistry, radioimmunoassay and in vitro pharmacology. Ann Neurol 21:431-437.

Edvinsson, L., McCulloch, J., Kingman, T. A., Uddman, R. (1986) On the functional role of the trigeminocerebrovascular system in the regulation of cerebral circulation. In: Neural Regulation of the Cerebral Circulation (Owman, C., Hardebo, J. E., eds), Stockholm, Elsevier Science Publishers BV, pp 407-418.

Goadsby, P. J., Duckworth, J. W. (1987) Effect of stimulation of trigeminal ganglion on regional cerebral blood flow in cats. Am J Physiol 253:270-274.

Goadsby, P. J., Edvinsson, L., Ekman, R. (1988) Release of vasoactive peptides in the extracerebral circulation of man and the cat during activation of the trigeminovascular system. Ann Neurol 23:193-196.

Goadsby, P. J., Lambert, G. A., Lance, J. W. (1986) Stimulation of the trigeminal ganglion increases flow in the extracerebral but not the cerebral circulation of the monkey. Brain Res 381:63-67.

Hashem H E, El-Din Safwat M D, Algaidi S. (2012) The effect of monosodium glutamate on the cerebellar cortex of male albino rats and the protective role of vitamin C (histological and immunohistochemical study). J Mol Histol. 43(2):179-86

Ichijo M, Iwasawa E, Numasawa Y, Miki K, Ishibashi S, Tomita M, Tomimitsu H, Kamata T, Fujigasaki H, Shintani S, Mizusawa H. (2015a) Significance of development and reversion of collaterals on MRI in early neurologic improvement and long-term functional outcome after intravenous thrombolysis for ischemic stroke. AJNR Am J Neuroradiol. 36:1839-1845.

Lambert, G. A., Bogduk, N., Goadsby, P. J., Duckworth, J. W., Lance, J. W. (1984) Decreased carotid arterial resistance in cats in response to trigeminal stimulation. J Neurosurg 61:307-315.

Lambert, G. A., Goadsby, P. J., Zagami, A. S., Duckworth, J. W. (1988) Comparative effects of stimulation of the trigeminal ganglion and the superior sagittal sinus on cerebral blood flow and evoked potentials in the cat. Brain Res 453:143-149.

Lang, R., Zimmer, R. (1974) Neurogenic control of cerebral blood flow. Exp Neurol 43:143-161.

Lee, Y., Kawai, Y., Shiosaka, S., Takami, K., Kiyama, H., Hillyard, C. J. (1985) Coexistence of calcitonin gene-related peptide and substance P-like peptide in single cells of the trigeminal ganglion of the rat: immunohistochemical analysis. Brain Res 330:194-196.

Liu-Chen, L. Y., Han, D. H., Moskowitz, M. A. (1983a) Pia arachnoid contains substance P originating from trigeminal neurons. Neuroscience 9:803-808.

Liu-Chen, L. Y., Mayberg, M. R., Moskowitz, M. A. (1983b) Immunohistochemical evidence for a substance P-containing trigeminovascular pathway to pial arteries in cats. Brain Res 268: 162-166.

Liu-Chen, L-Y, Gillespie, S. A., Norregaard, T. V., Moskowitz, M. A. (1984) Co-localization of retrogradely transported wheat germ agglutinin and the putative neurotransmitter substance P within trigeminal ganglion cells projecting to cat middle cerebral. J Comp Neurol 225: 187-192.

Liebeskind D S. (2003) Collateral circulation. Stroke; 34:2279-2287

May J M et al. (2012) Vitamin C transport and its role in the central nervous system. Subcell Biochem.

Powers W J, Rabinstein A A, Ackerson T, et al. 2018 Guidelines for the early management of patients with acute ischaemic stroke: a guideline for healthcare professionals from the American Heart Association/American Stroke Association.

Qureshi A I, El-Gengaihi A, Hussein H M, Suri M F, Liebeskind D S. (2008) Occurrence and variability in acute formation of leptomeningeal collaterals in proximal middle cerebral artery occlusion. J VascInterv Neurol. 1:70-72.

Ruskell, G. L., Simons, T. (1987) Trigeminal nerve pathways to the cerebral arteries in monkeys. J Anat 155:23-37.

Rebec G V, Pierce R C. (1994) A vitamin as neuromodulator: ascorbate release into the extracellular fluid of the brain regulates dopaminergic and glutamatergic transmission. Prog Neurobiol. 43(6):537-65. Review.

Shah S A et al. (2015) Vitamin C neuroprotection against dose-dependent glutamate-induced neurodegeneration in the postnatal brain. Neurochem Res.

Sheth S A, Liebeskind D S. (2014) Imaging Evaluation of Collaterals in the Brain: Physiology and Clinical Translation. Curr Radiol Rep. 2:29.

Shuaib A. Butcher K. Mohammad A A. Saqqur M. Liebeskind D S. (2011) Collateral blood vessels in acute ischaemic stroke: a potential therapeutic target. *Lancet Neurol.* 10: 909-921

Simons T, Ruskell G L. (1988) Distribution and termination of trigeminal nerves to the cerebral arteries in monkeys. J Anat. 159:57-71.

Spoelstra-de Man A M E, Elbers P W G, Oudemans-van Straaten H M. (2018) Making sense of early high-dose intravenous vitamin C in ischemia/reperfusion injury. Crit Care. 20; 22(1): 70.

Suzuki N, Hardebo J E, Kahrstrom J, Owman C H, (1990) "Effect on cortical blood flow of electrical stimulation of trigeminal cerebrovascular nerve fibres in the rat," Acta Physiol. Scand., 138, 307-315

Suzuki N et al., (1989)"Trigeminal fibre collaterals storing substance P and calcitonin gene-related peptide associate with ganglion cells containing choline acetyltransferase and vasoactive intestinal polypeptide in the sphenopalatine ganglion of the rat. An axon reflex modulating parasympathetic ganglionic activity?" Neuroscience 30:595-604

Syelaz J, Hara H, Pinard E, Mraovitch S, Mackenzie E T, Edvinsson L, (1988) "Effects of stimulation of the sphenopalatine ganglion on cortical blood flow in the rat," Journal of Cerebral Blood Flow and Metabolism," 8, 875-878

Toda N et al., (2000) "Cerebral vasodilation induced by stimulation of the pterygopalatine ganglion and greater petrosal nerve in anesthetized monkeys," Neuroscience 96(2):393-398

UCLA Collateral Investigators. Bang O Y, Saver J L, Buck B H, Alger J R, Starkman S, Ovbiagele B, Kim D, Jahan R, Duckwiler G R, Yoon S, Viñuela F, Liebeskind D S. (2008) Impact of collateral flow on tissue fate in acute ischaemic stroke. J Neurol Neurosurg Psychiatry. 79:625-629

Patent Citations (37)

| Publication number | Priority date | Publication Date | Assingnee | Title |
|---|---|---|---|---|
| NZ214348A | 1985 Nov. 27 | 1988 Jul. 28 | Walker T H & Sons Ltd | *Electrically stunning animals through nose and neck contacts* |
| US4926880A | 1988 Nov. 8 | 1990 May 22 | Microcurrents | Method for relieving sinus and nasal congestion utilizing micro currents |
| RU1799577C | 1989 Aug. 17 | 1993 Mar. 7 | 07МсМежотраслевой научно-технический комплекс "Микрохирургия глаза | "Method for improving vision function affected by ophthalmic nerve and retina disease |
| US5099829A | 1990 Apr. 25 | 1992 Mar. 31 | Wu An Chuan | Massage device good for eyes |
| US5072724A | 1990 Nov. 23 | 1991 Dec. 17 | Joseph Marcus | Vibrational liquid-wave stimulating therapy mask apparatus for facial health and beauty care |
| US5360438A | 1993 Jan. 26 | 1994 Nov. 1 | Fisher Mary R | Method and device for improving cranial nerve function to improve muscle function and thereby overcome visual/perceptual dysfunction |
| US5713833A | 1994 Jan. 26 | 1998 Feb. 3 | Milligan; Lee John | Septum nerve stimulator |
| US5800685A | 1996 Oct. 28 | 1998 Sept. 1 | Cardiotronics Systems, Inc. | Electrically conductive adhesive hydrogels |
| US6458157B1 | 1997 Aug. 4 | 2002 Oct. 1 | Suaning Gregg Joergen | Retinal stimulator |
| US6020445A | 1997 Oct. 9 | 2000 Feb. 1 | Johnson & Johnson Vision Products, Inc | .Silicone hydrogel polymers |
| US6083251A | 1997 Nov. 13 | 2000 July 4. | Shindo; Kohei | Eye treatment method and apparatus |
| US6324429B1 | 1998 May 8 | 2001 Nov. 27 | Massachusetts Eye And Ear Infirmary | Chronically implantable retinal prosthesis |
| US6035236A | 1998 Jul. 13 | 2000 Mar. 7 | Bionergy Therapeutics, Inc | Methods and apparatus for electrical microcurrent stimulation therapy |
| US7146209B2 | 2000 May 8 | 2006 Dec. 5 | Brainsgate, Ltd | .Stimulation for treating eye pathologies |
| US7120489B2 | 2000 May 8 | 2006 Oct. 10 | Brainsgate, Ltd. | Method and apparatus for stimulating the sphenopalatine ganglion to modify properties of the BBB and cerebral blood flow |
| US6526318B1 | 2000 Jun. 16 | 2003 Feb. 25 | Mehdi M. Ansarinia | Stimulation method for the sphenopalatine ganglia, sphenopalatine nerve, or vidian nerve for treatment of medical conditions |
| JP4781576B2 | 2001 Feb. 28 | 2011 Sept. 28 | 株式会社ニデック | Intraocular implantable visual stimulation device |
| US7321795B2 | 2003 Mar. 24 | 2008 Jan. 22 | Les Bogdanowicz | Compositions for electric stimulation of the eye |
| JP2007044323A | 2005 Aug. 11 | 2007 Feb. 22 | Nidek Co Ltd | Eyesight regeneration supporting apparatus |
| US8311634B2 | 2006 Jun. 16 | 2012 Nov. 13 | Second Sight Medical Products Inc | .Apparatus and method for electrical stimulation of human retina |
| US20080183242A1 | 2007 Jan. 29 | 2008 Jul. 31 | Nidek Co., Ltd | Electrical stimulation method for vision improvement |

-continued

| Publication number | Priority date | Publication Date | Assingnee | Title |
|---|---|---|---|---|
| JP4970069B2 | 2007 Jan. 30 | 2012 Jul. 4 | 株式会社ニデック | Vision regeneration assisting device |
| SU1560205A1 | 1987 Apr. 27 | 1990 Apr. 30 | . Пензенский государственный институт усовершенствовани я врачей | Device for intranasal vibromassage |
| US4911149A* | 1984 Jun. 18 | 1990 Mar. 27 | Urological Instruments Research, Inc | .Vibratory treatment method and apparatus |
| SU1560205A1 | 1987 Apr. 27 | 1990 Apr. 30 | . Пензенский государственный институт усовершенствовани я врачей | Device for intranasal vibromassage |
| US9872814B2 | 2012 Mar. 20 | 2018 Jan. 23 | Chordate Medical Ag | Vibration pattern for vibration stimulation |
| US9474684B2 | 2012 Mar. 20 | 2016 Oct. 25 | Chordate Medical Ab | Electroactive vibration method |
| US9895279B2 | 2011 Dec. 16 | 2018 Feb. 20 | Chordate Medical Ab | Stimulation of hypothalamus |
| WO2013165697A1 | 2012 Apr. 30 | 2013 Nov. 7 | Vigilant Medical Solutions, Inc | Indirect and non-invasive trigeminal neuromodulation for the treatment of disease |
| US9440065B2 | 2013 Apr. 19 | 2016 Sept. 13 | Oculeve, Inc | Nasal stimulation devices and methods |
| US9687652B2 | 2014 Jul. 25 | 2017 Jun. 27 | Oculeve, Inc | Stimulation patterns for treating dry eye |
| US0195165A1 | 2006 Jan. 25 | 2006 Aug. 31 | Valam Corp, Gertner Michael | Optical therapy devices, systems, kits and methods for providing therapy to the body cavity |
| US7351253B2 | 2005 Jun. 16 | 2008 Apr. 1 | Codman and Shurtleff | Intranasal red light probe for treating Alzheimer's disease |
| US20110022130A1* | 2005 Jun. 16 | 2011-01-27 | Dimauro Thomas MIntranasal | Red Light Probe For Treating Alzheimer's Disease |
| US20170225011A1* | 2016 Feb. 8 | 2017-08-10 | Ricky A. Frost | Laser device for intracranial illumination via oral or nasal foramina access |
| US9265967B2* | 2011 Aug. 5 | 2016 Feb. 23 | Lumimed, Llc | Apparatus and method for treating rhinitis |
| US20170087377A1* | 2015 Sept. 28 | 2017 Mar. 30 | DePuy Synthes Products, LLC | Transnasal Delivery of Low Level Light Via the Sphenoidal Sinus to Irradiate the Substantia Nigra |

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

BRIEF DESCRIPTION OF THE DRAWINGS

Figure 1:
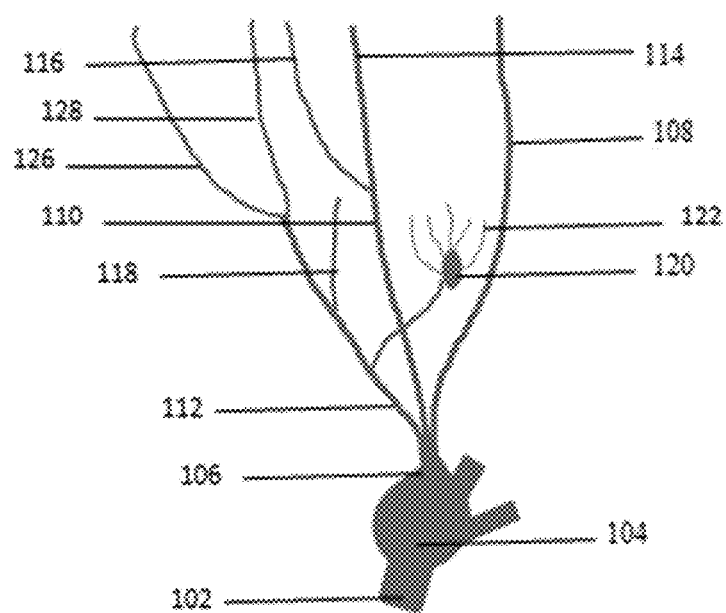
Figure 2A:
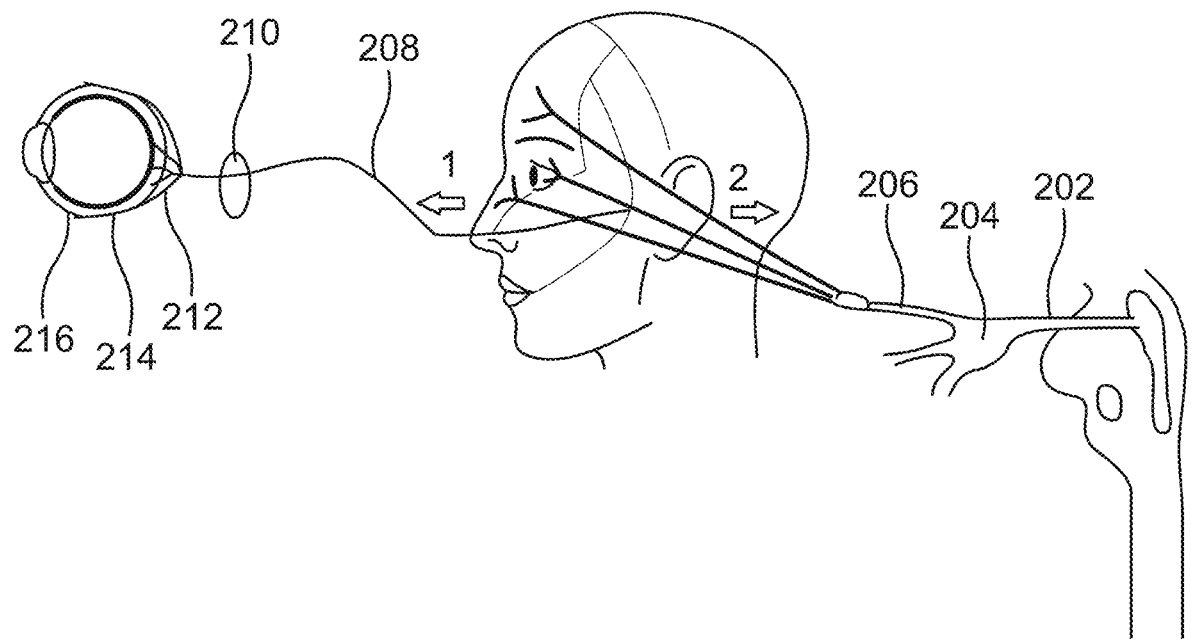
Figure 2B:
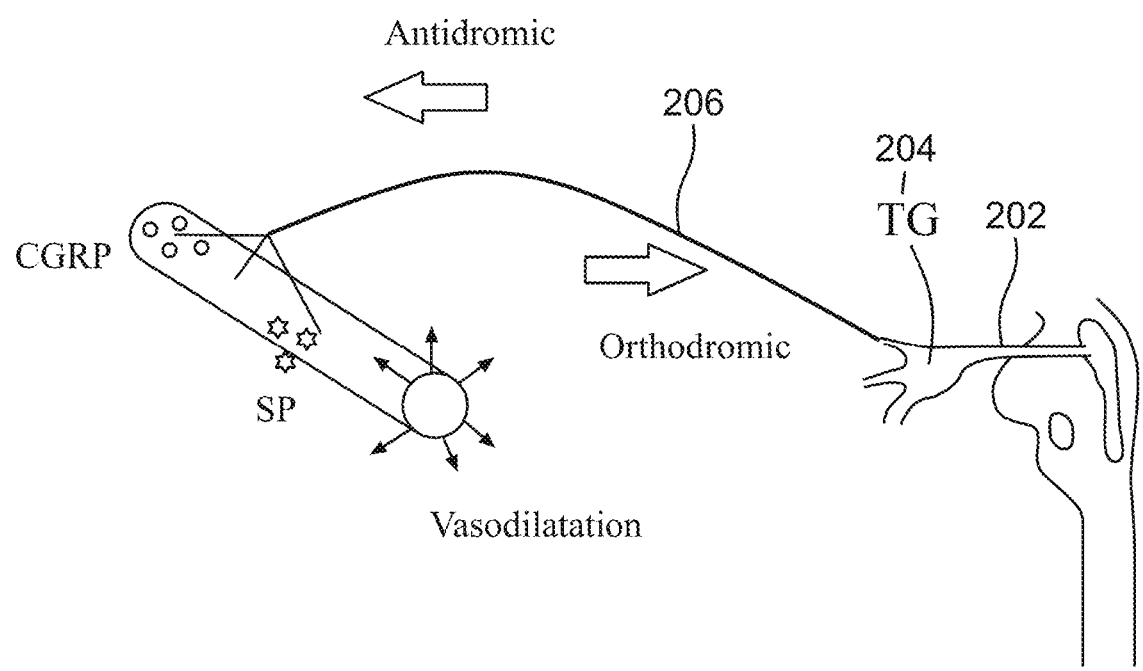
Figure 3:
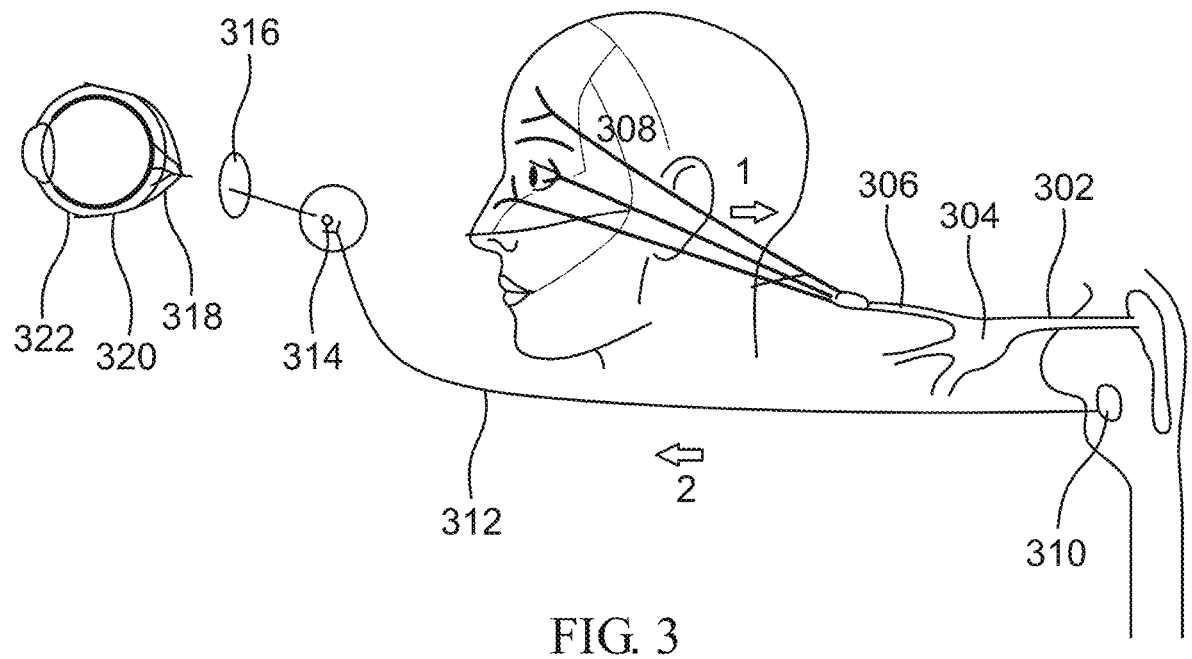
Figure 4:
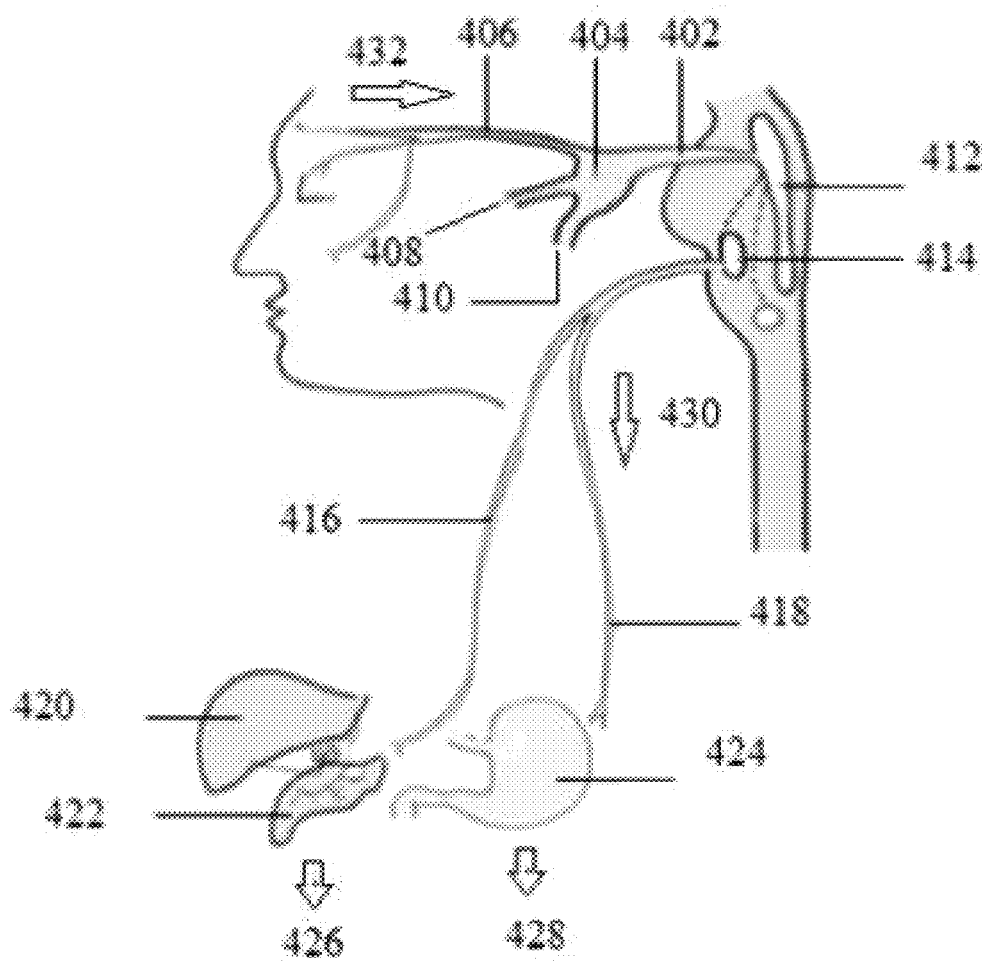
Figure 5:
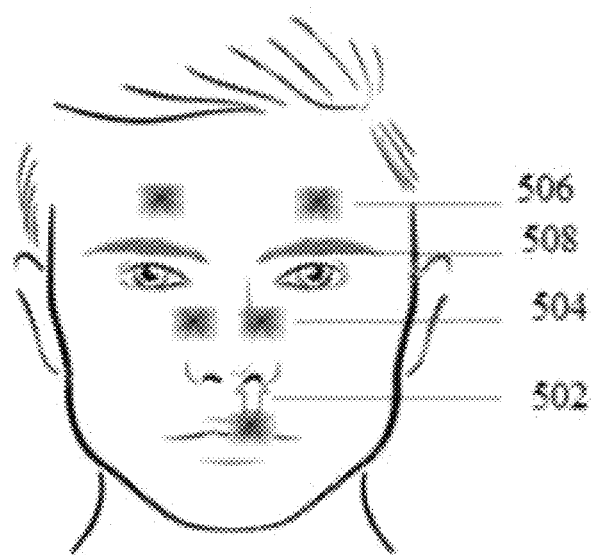
Figure 6:
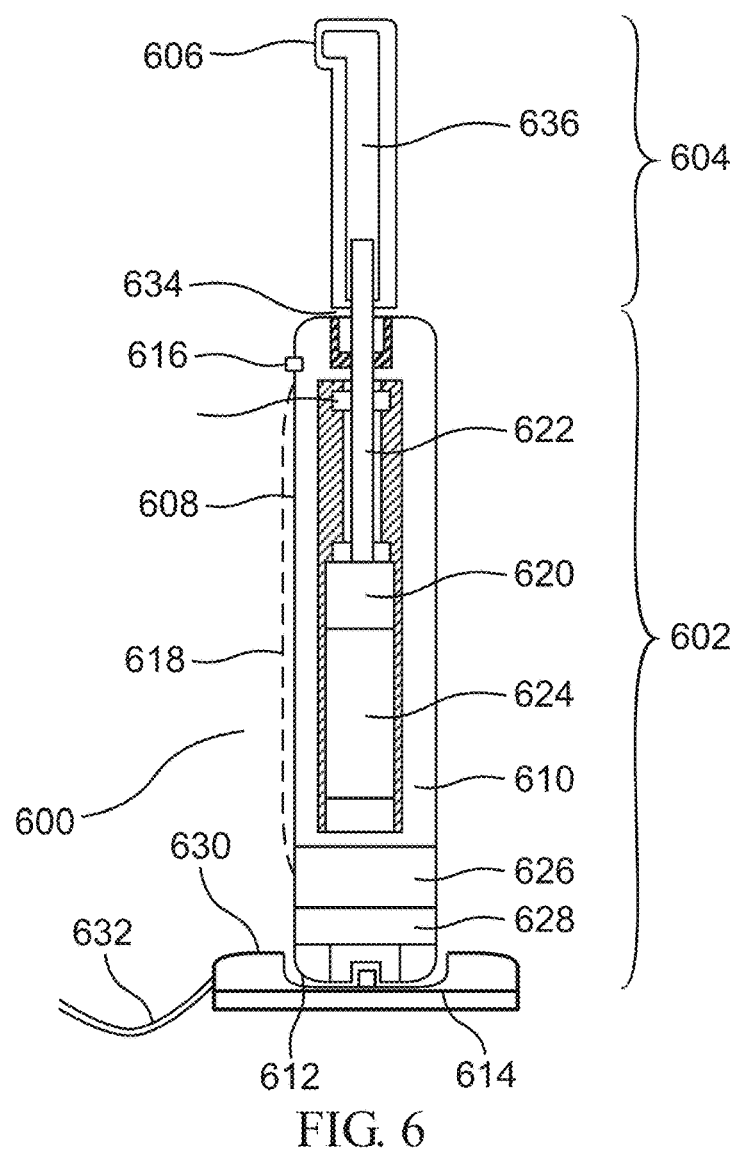
Figure 7A:
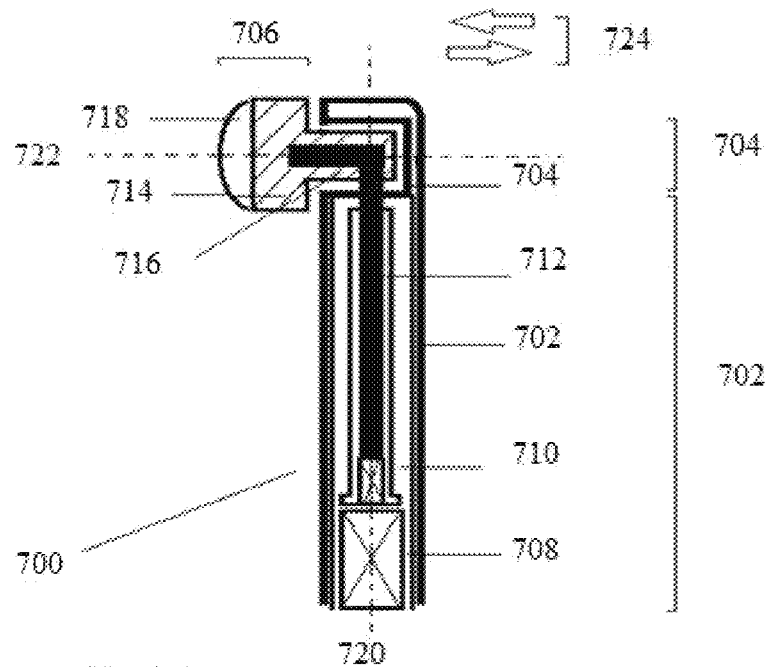
Figure 7B:
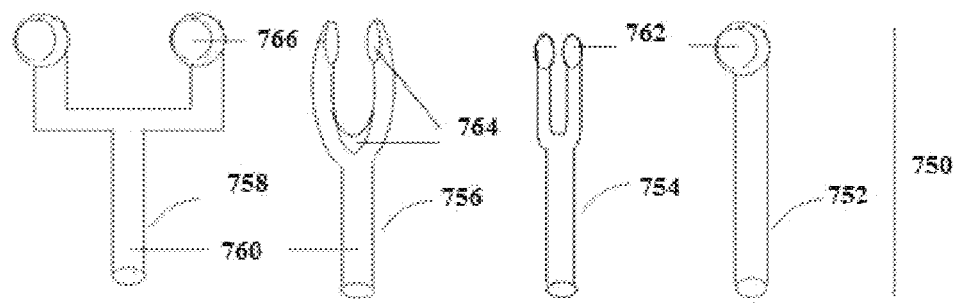
Figure 7C:
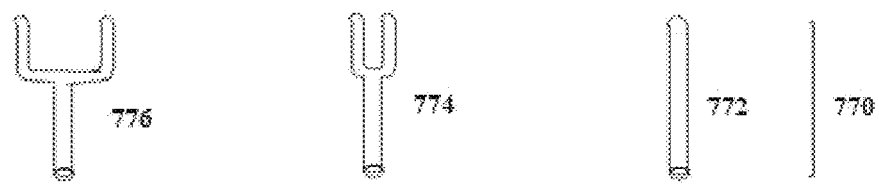
Figure 8:
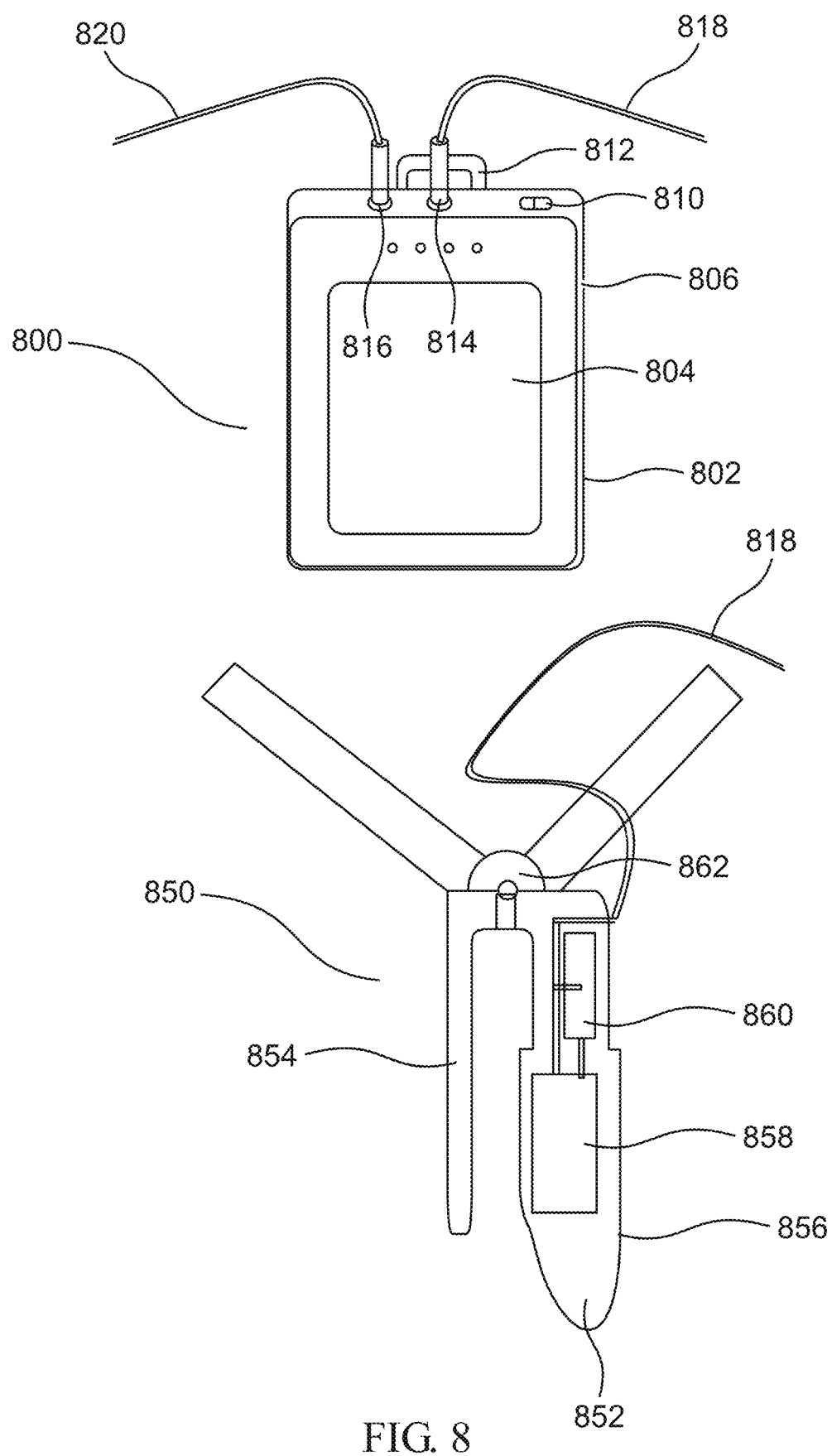
Figure 10B:
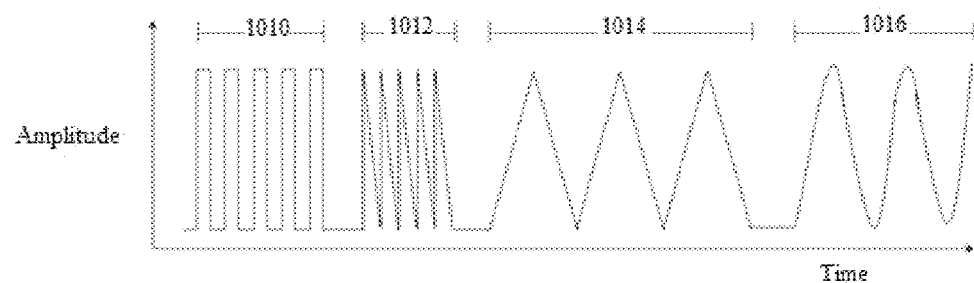
Figure 10C:
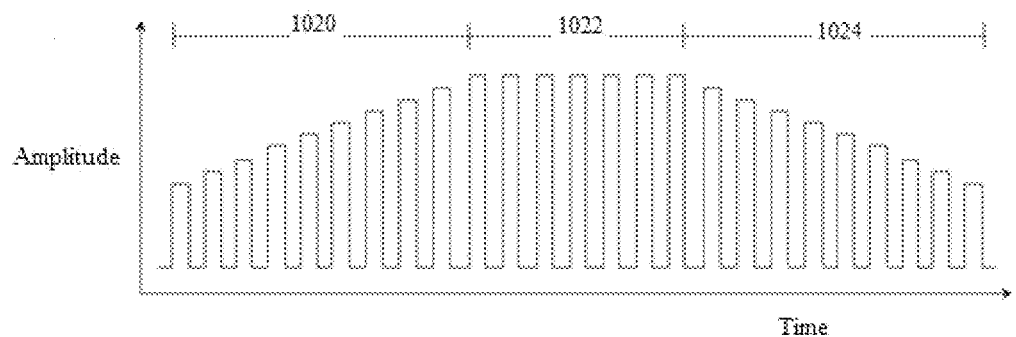
Figure 10D:
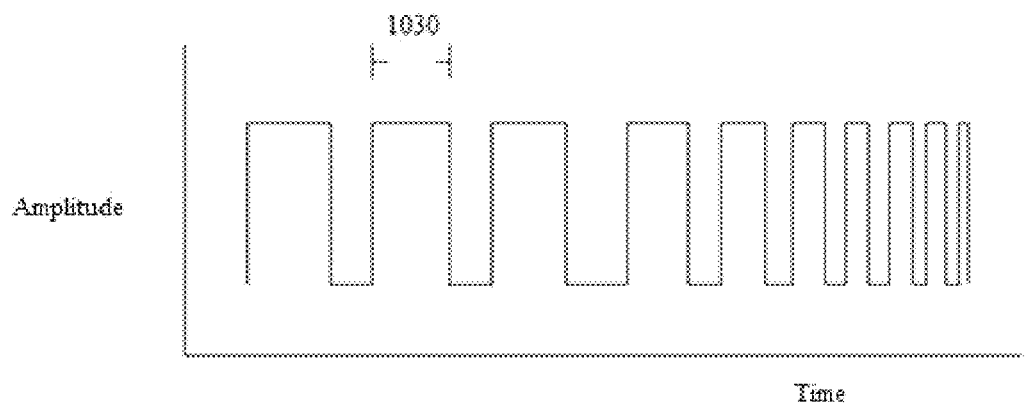
Figure 10E:
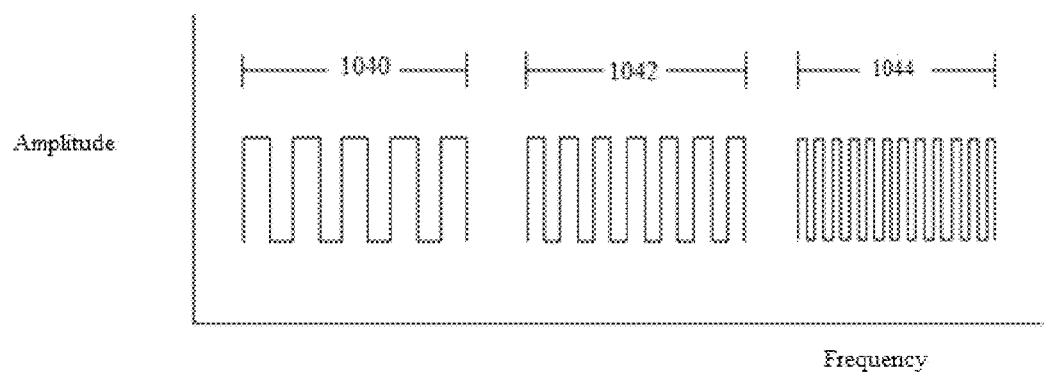
Figure 11:
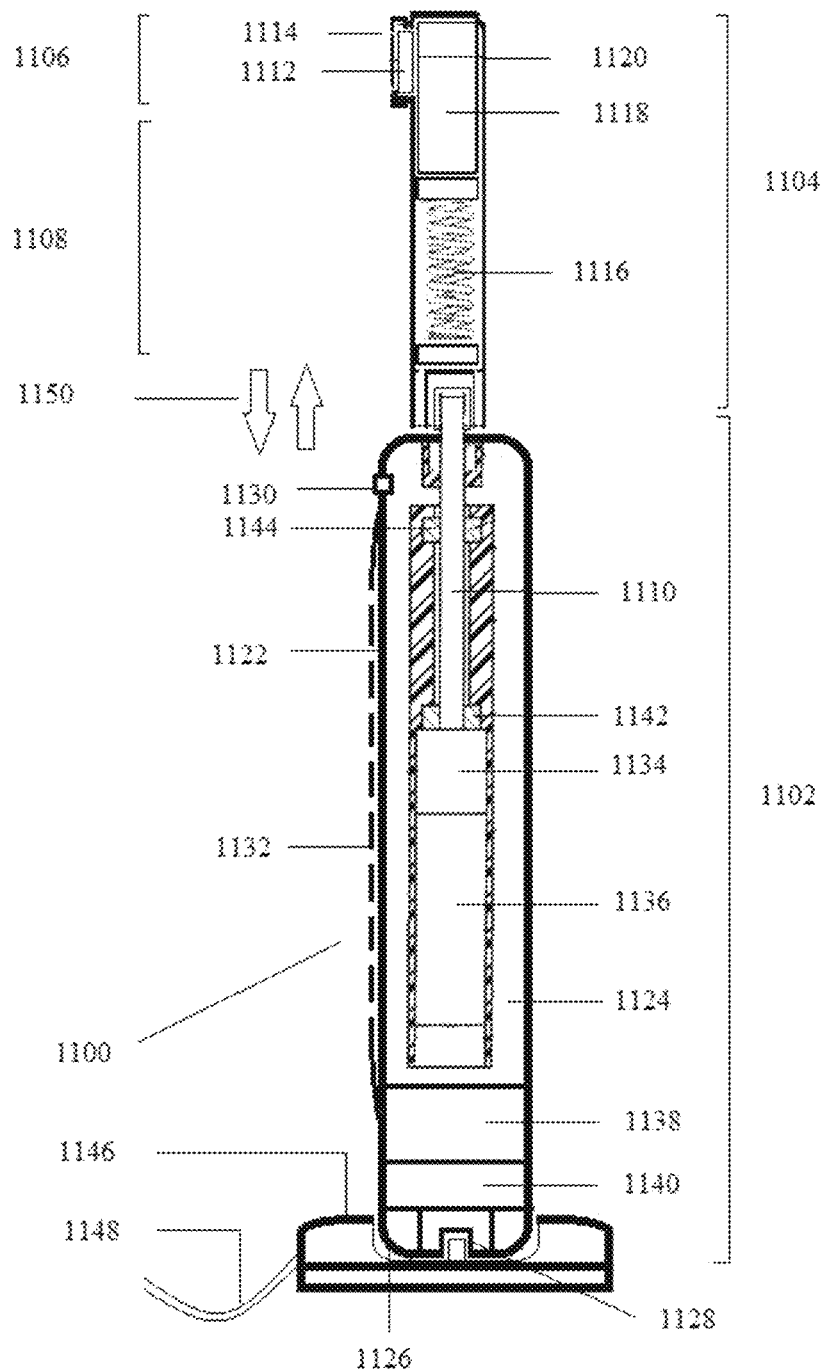
Figure 14A:
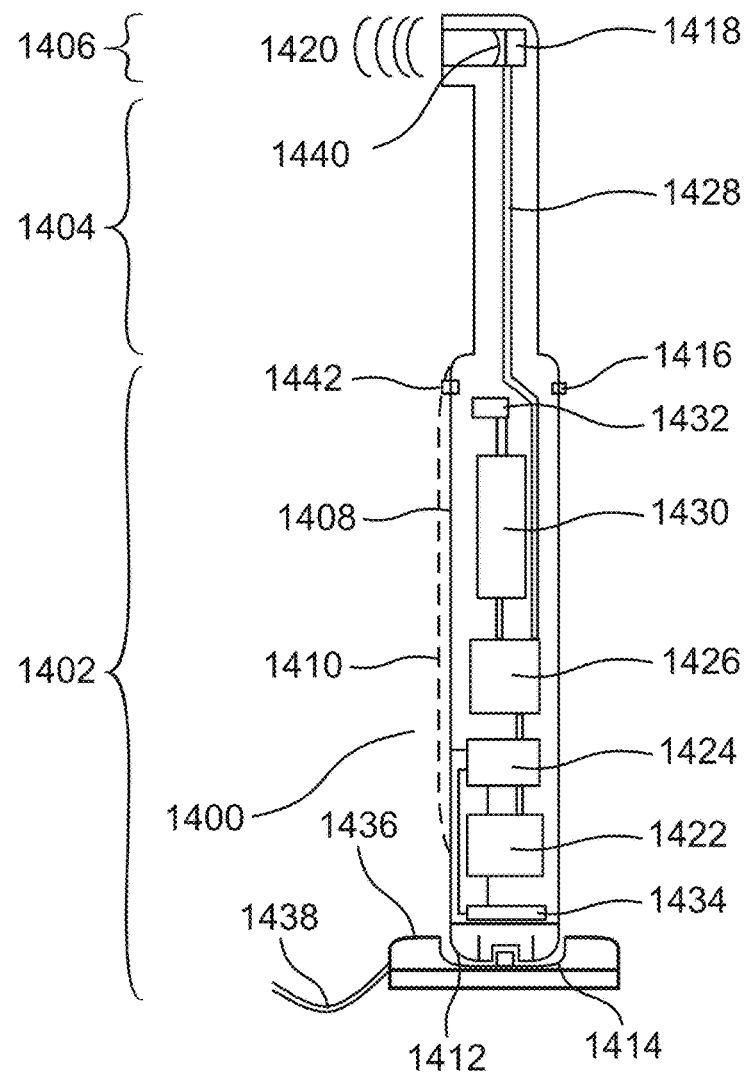
Figure 14B:
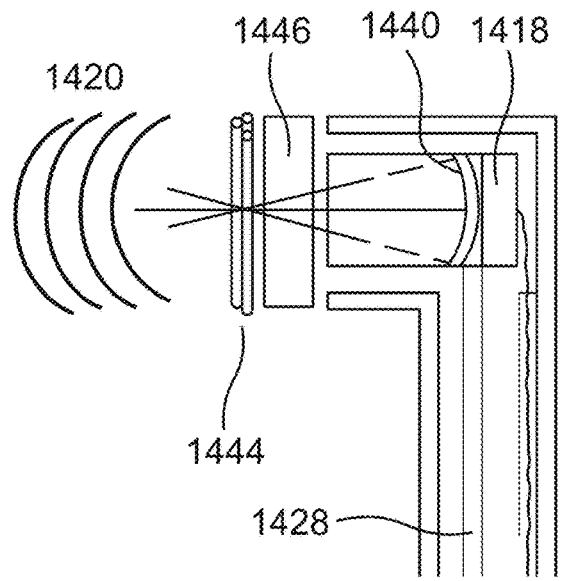
Figure 15:
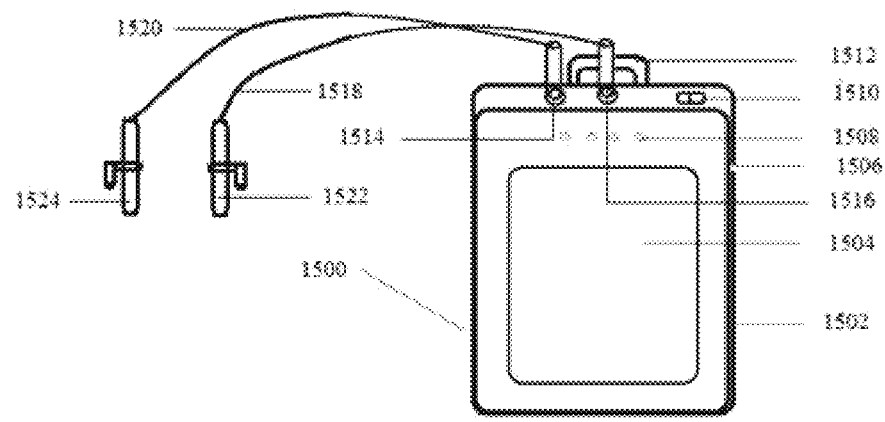

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.
In the drawings:
FIG. 1 Illustrates ophthalmic division of trigeminal nerve
FIG. 2A-B Illustrate a proposed pathway of trigemino-vascular system (TVS).
FIG. 3 Illustrates a proposed pathway of trigemino-autonomic brain reflex. The facial nerve presented as the efferent limb of the reflex.
FIG. 4. Illustrates a proposed pathway of trigemino-autonomic brain reflex. The vagus nerve presented as the efferent limb of the reflex and pancreas is the organ to be activated.
FIG. 5 Illustrates exemplary sites of stimulation of V1.
FIG. 6 Depicts an exemplary handheld vibrotactile Ophthalmic Nerve stimulator (V-ONS 600).
FIG. 7A. Illustrates distal portions of exemplary stimulator probe 700 for V-ONSor 600. FIGS. 7B and 7C illustrate various exemplary embodiments of disposable heads of the stimulator probe 750 and their covering 770.
FIG. 8. depict an exemplary embodiment of a portable V-ONSor with its nasally clipped application head.
FIGS. 9A and B depict an exemplary nasal supported version of V-ONSor 900
FIG. 10A shows exemplary regular un-modulated waveforms and the features of waveform (amplitude, pulse width, an on time, and off time). FIG. 10B shows exemplary shapes of un-modulated waveforms. FIG. 10C illustrates exemplary amplitude variations over time. FIG. 10.D illustrates exemplary pulse width variations over time. FIG. 10.E. illustrates exemplary modulations of frequency waveform parameters.
FIG. 11 Depict an exemplary handheld chemical stimulator Ch-ONSor 1100
FIGS. 12A-B illustrates an exemplary construction of the chemical stimulator probe 1200
FIGS. 13A-B illustrates an exemplary construction of the vibro-chemical stimulator probe FIGS. 14A-B Depicts an exemplary handheld ultrasonic ONSor (U-ONSor 1400) and its probe FIG. 15 Depicts an exemplary of portable optical ONSor (O-ONSor 1500)

Figure 16:
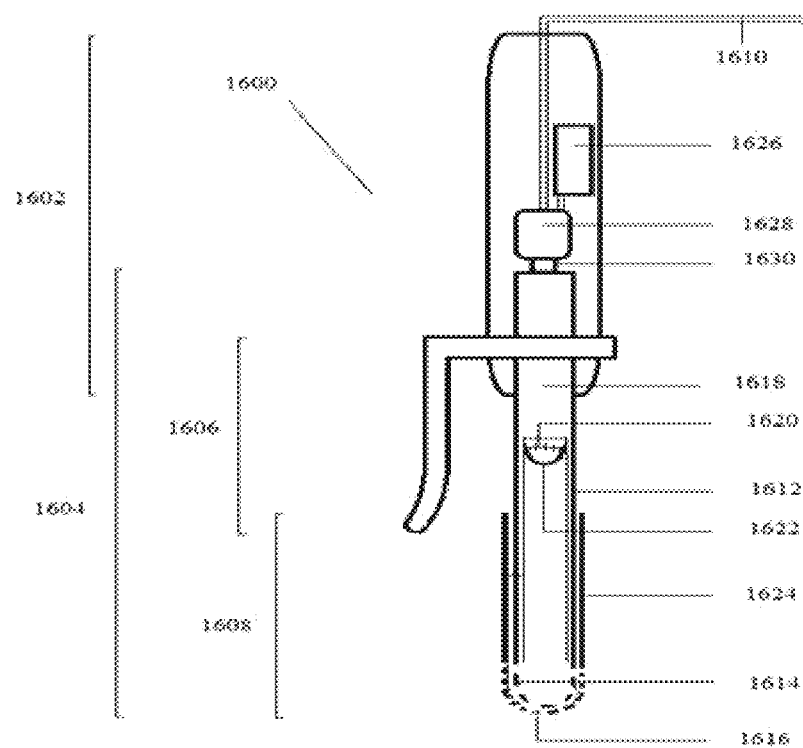

FIG. 16 depicts an exemplary of an exemplary construction of the optical stimulator tube 1600 with disposable sleeve FIGS. 17A-B is illustrates an exemplary construction of the hybrid electro-optical ONSor 1700 with an electrical stimulating sleeve 1708

FIGS. 18.A-B illustrates an exemplary construction of the hybrid electro-optical ONSor 1800

Figure 19A:
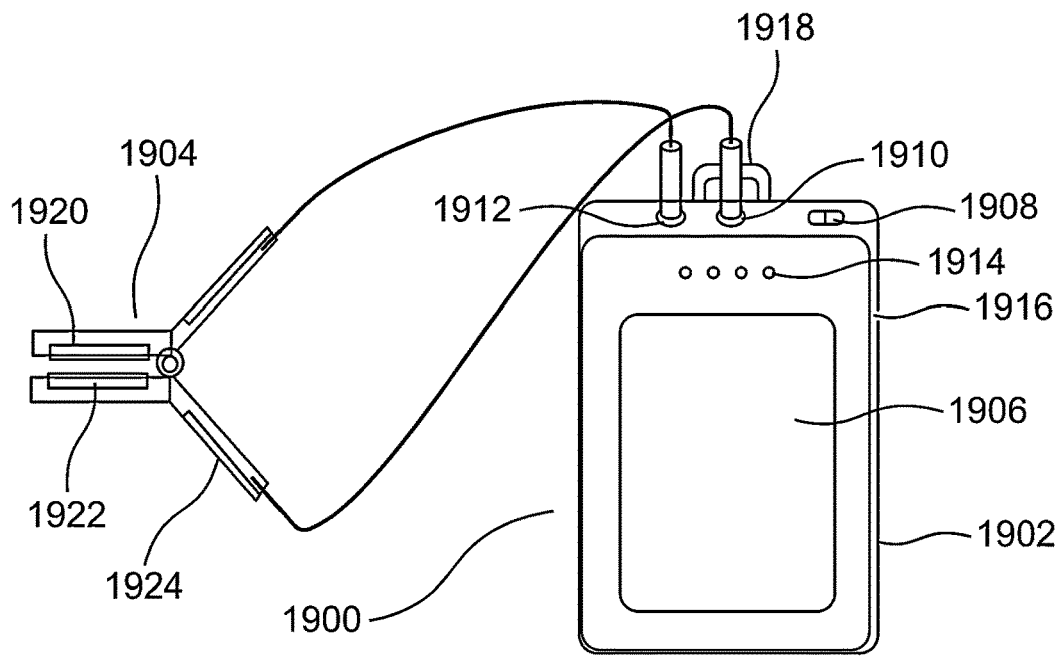
Figure 19B:
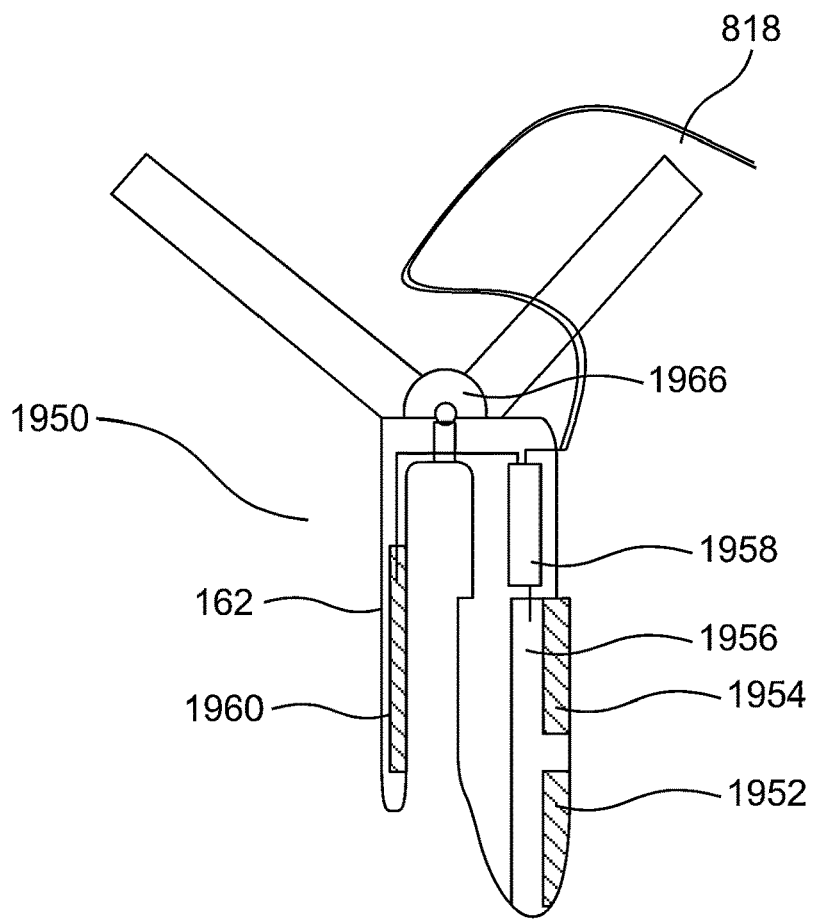

FIGS. 19A-B shows schematic illustrations of exemplary configurations of a portable electrical ONSor (E-ONSor 1900)

Figure 20:
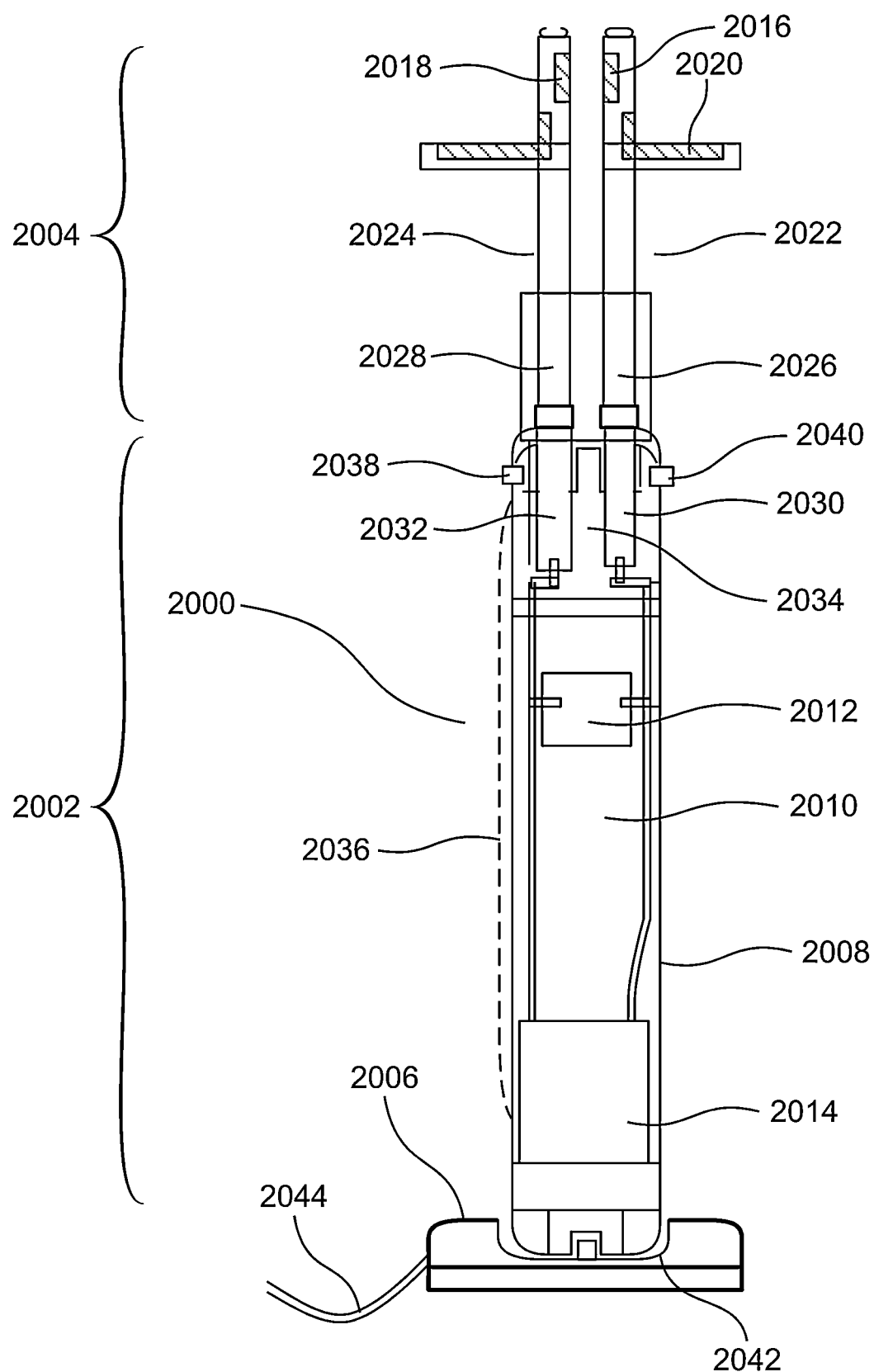

FIG. 20 show schematic illustrations of exemplary configurations of a portable hand held electrical ONSor (E-ONSor 2000)

Figure 21:
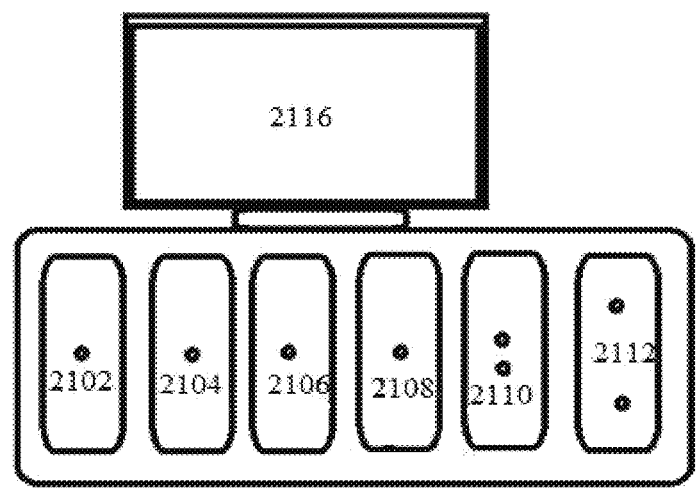

FIG. 21 depict an exemplary multi-modular system for ONS

DESCRIPTION OF SPECIFIC EMBODIMENTS OF THE INVENTION

Overview

An aspect of some embodiments of the current invention relates to treatment method and/or system for treatment of brain and/or eye strokes by improving CBF and/or OBF. In some embodiments, the treatment includes neuromodulation. Optionally the neuromodulation is non-invasive, relatively inexpensive, promptly and easily applicable by medical staff of stroke unit, and by physicians in emergency units prior arrival of subject to specialized units for stroke treatment. For example, the treatment may include up-regulation of the trigemino-vascular system TVS and/or activation of parasympathetic circuit of cerebral and/or ocular circulation. For example, treatment objective may be achieved using neuromodulation and/or inhibition of sympathetic activity. For example, inhibition of sympathetic activity may be applied when sympathetic activity is abnormally increased. Optionally, inhibition of sympathetic activity may be achieved via intravenous administration of pharmacological dose of ascorbic acid.

An aspect of some embodiments of the current invention relates to restoration of a physiological microenvironment that facilitated improved CBF and/or OBF and/or delivery of sufficient oxygen, glucose, anticoagulants, pharmaceuticals agents to the targeted tissues of the brain, retina, and/or the optic nerve and/or control of hyperglycemia associated with strokes via enhancement of pancreatic secretion of insulin. In some embodiments, ONS and improved CBF may prevent or slow down nerve cell death, improve functional neuroplasticity, reduce neuroinflammation and/or create local conditions favorable to cell survival. In some embodiments, ONS combined with intravenous administration of pharmacological doses of ascorbic acid may be used to target diverse pathophysiologies of acute brain and/or ocular ischemia.

In some embodiments of the present invention, an acute ocular/cerebral stroke and/or emergency medical condition of a subject is treated by stimulating ipsilateral V1 at least at one site, by applying vibrotactile, chemical, ultrasonic, optical, electrical and/or hybrid electric-optical stimulation to the site. Such treatment is typically applied as soon as possible within 3-24 hours of the onset of acute ischemia. The easy applicability, availability, relatively low cost and simplicity of ONS make such an intervention an effective method for stroke treatment.

Specific Embodiment

DESCRIPTION OF SPECIFIC EMBODIMENTS OF THE INVENTION

In some embodiment treatment may include nerve stimulation. For example, the ophthalmic division of trigeminal nerve (V1) may be stimulated on the ipsilateral side of the stroke. Optionally, stimulation may include regulation (for example up regulation) of trigeminovascular system (TVS) and/or trigeminal autonomic brain reflexes (TABRs) and/or pancreatic Trigemino-vagal reflex (TVR). For example, intranasal site of stimulation of V1 more specifically the mucosa of nasal septum of the vestibule is preferable site of stimulation in the present invention. Other extranasal sites for V1 stimulation include, skin of nasal bridge, and forehead. In some embodiments, the subject's TVS and/or autonomic nervous system (ANS) are modulated promptly in a manner that is effective to treat the subject for acute brain and/or eye stroke In some embodiments, the subject's ipsilateral TVS is modulated in a manner that is effective to induce acute development of leptomeningeal collateral circulation sufficient to ameliorate the ischemic effect of occluded cerebral artery via increasing blood flow to the penumbra, enhancing successful recanalization, decreasing the infarction volume, limiting the stroke damage and improving functional recovery without hemorrhagic transformation. The leptomeningeal collateral circulation is a network of small blood vessels in the brain that connects branches of the middle, anterior and posterior cerebral arteries that maintain and stabilize CBF when principle routes of blood flow were occluded or compromised. Active dilatation of leptomeningeal collateral circulation via ONS is an effective method for increasing blood flow to the penumbra and limiting the stroke damage. Sensory fibers innervating the blood vessels of leptomeningeal collateral circulation arise from the trigeminal nerve, mostly within $V_1$.

In some embodiments of this invention, ONS at one or more sites may cause up regulation of TVS and/or TABRs. For example, up regulation of TVS and/or stimulation of V1, may include V1 sensory fibers innervating internal carotid artery, basilar artery, anterior cerebral artery, middle cerebral artery, and posterior cerebral artery, anterior communicating artery, posterior communicating arteries, leptomeningeal collateral arteries and their branches that contain both SP and/or CGRP. Additionally or alternatively, up regulation of TVS and/or stimulation of V1, may include V1 sensory fibers innervating ophthalmic artery, anterior and posterior ciliary arteries, and/or choroidal blood vessels that contain both SP and/or CGRP. These potent vasodilating agents will be released from V1 nerve endings in response to ONS causing acute development of leptomeningeal collateral circulation and a robust vasodilator effect and/or increased CBF and/or OBF. Optionally, a specific portion of TVS and/or ANS is modulated via stimulating ipsilateral V1 causing a robust vasodilator effect and/or increased CBF and/or OBF in the affected side for example hemisphere of the brain or an eye to avoid intracerebral vascular steal phenomenon. Additionally or alternatively, a specific portion of ANS may be modulated causing stimulation of efferent vagal nerve which affects insulin secretion by beta cells of islets of Langerhans. For example, excess insulin may increase glucose uptake and/or glycolysis by starving ischemic nerve cells of the brain, retina and/or optic nerve, promoting their survival. Additionally, insulin secretion might control hyperglycemia associated with cerebral stroke prevents its harmful effects on ischemic tissue and promote functional recovery. Alternatively or additionally, vagal nerve activation via ONS may activate anti-inflammatory effects on the brain, retina and/or optic nerve and minimize the inflammatory response produced by ischemia/reperfusion.

In some embodiments of the present invention, ONSor is provided for the treatment of acute ischemic brain or ocular stroke. The system is configured to apply excitatory stimulation to dilate primary collateral circulation (circle of Willis) or secondary collateral circulation (leptomeningeal collateral circulation) thereof maintaining sufficient blood flow to the targeted decompromised ischemic brain tissue, preventing progression of ischemia and increases the chances of successful recanalalization rate without hemorrhagic transformation.

In some embodiments of the present invention, ophthalmic nerve stimulator ONSor is provided for the treatment of acute ischemic brain stroke. The system is configured to apply excitatory stimulation to induce acute development of leptomeningeal collateral circulation and dilate cerebral vessels at the vicinity of occlusion, thereof increases retrograde blood flow that may help to expose all portions of the thrombus to thrombolytic agents and enhances spontaneous or r-tPA mediated recanalization of occluded cerebral artery and restoration of sufficient CBF.

In some embodiments of the present invention, ONSor is provided for the treatment of acute ischemic brain or eye stroke. The system is configured to apply excitatory stimulation to V1 intranasally and/or at extra nasal sites. The system configures the stimulation to decrease vascular resistance and dilate cerebral vessels and ocular blood vessels, thereby increasing CBF and/or OBF to affected brain tissue and/or ocular tissue and tissue in a vicinity thereof, and/or to induce the release of one or more potent vasodilating substances such as CGRP, substance P and neurokinin. Such stimulation is primarily intended to arrest the spreading of the initial ischemic core, such as by restoring blood flow to the penumbra and/or increased choroidal flow in order to prevent damage to cells therein, and/or by releasing neuroprotective substances. Such stimulation may also save some cells within the ischemic core, such as neuronal cells.

In some embodiment treatment may include ONS. Optionally, stimulation may include regulation pancreatic Trigemino-vagal reflex (TVR). For example, In some embodiments, the subject's pancreatic TVR is modulated in a manner that is effective to treat hyperglycemia associated with brain stroke of the subject thereof to improve long term functional recovery of the brain in a subject.

In some embodiments of the present invention, ophthalmic nerve stimulator (ONSor) is provided stimulation within 3 to 24 hours of the stroke onset, while a significant penumbra remains. In some embodiment, ONS is applied hourly in the first 6 hours of acute stage of the stroke and 3 hourly thereafter for one week (acute stage), 6 hourly during sub acute phase (2nd week), and/or once to twice daily during the chronic rehabilitative stage (2 weeks-6 months). ONS of this invention is non invasive, portable easily and instantly applicable and relatively non expensive method for subjects who are in an urgent need to such a treatment following brain and/or the eye stroke.

In some embodiments of the present invention, ONS is instantly applied to the ipsilateral side of the brain with stoke. This selective unilateral stimulation of V1 prevents relative decreased CBF in the ischemic tissue after vasodilation (Intracerebral steal phenomenon), and enhances preferential redistribution of CBF toward the affected side.

In some embodiments of the present invention, ONSor is provided for the treatment of acute ischemic brain or ocular stroke. The system is configured to dilate cerebral vessels including leptomeningeal collateral circulation and ocular blood vessels, thereby increasing cerebral blood flow (CBF) and/or ocular blood flow via release of one or more potent vasodilating substances such as CGRP, substance P and neurokinin. To guard against breakdown of BBB and/or BOB, ONS and intravenous administration of anti-oxidants were given during the acute phase and/or the dose and strength of ONS is adjusted to a level that could not significantly disrupt these barriers.

In some embodiments of the present invention, ONS is combined with administration high dose of intravenous anti-oxidants as a sympatholytic agent to combat the sympathetic overactivity induced by ischemic stroke. In some embodiments, ONS is combined with high dose of intravenous anti-oxidants to alleviate and minimize oxidative damage induced by ischemia/reperfusion in the affected tissue. In other embodiments of the present invention, ONS is combined with high dose of intravenous anti-oxidants for example, pharmacological doses of ascorbic acid to restore endothelial function of the blood vessels of brain and the eye in order to restore ocular blood flow autoregulation.

In some embodiments of the present invention, ONS is combined with intravenous administration of pharmacological doses of ascorbic acid as a potent antioxidant/sympatholytic agent to combat the sympathetic overactivity induced by ischemia/reperfusion wherein this combined therapy is sufficient to increase OBF more specifically the choroidal blood flow to compensate for occluded central retinal artery or compromised retinal blood flow until recanalization of occluded central retinal artery occurs and normal retinal blood flow is restored.

In some embodiments of the present invention, ONS combined with acute administration of intravenous ascorbic acid is efficient to restore sufficient OBF to the optic nerve head in individual suffering from acute anterior or posterior ischemic optic neuropathy via increasing OBF through other patent ciliary arteries or pial arteries until recanalization of occluded ciliary artery occurs and normal blood flow in the optic nerve head is restored.

In some embodiments, a potential subject is identified. For example, a subject may be a person who is identified as affected by and/or at risk for dysregulated reduced cerebral blood flow and/or acute cerebral disorders wherein said cerebral disease include, but are not limited to ischemic cerebral stroke related to cerebral arteries occlusion such as middle cerebral artery, vasospasm following subarachnoid hemorrhage (SAH), and traumatic brain injury (TBI).

In some embodiments, a potential subject is identified. For example, a subject may be a person who is identified as affected by and/or at risk for dysregulated reduced OBF and/or acute ocular disorders wherein said ocular disorders include, but are not limited to, ophthalmic artery occlusion, central retinal artery occlusion, branch retinal artery occlusion, central retinal vein occlusion, and branch retinal vein occlusion anterior ischemic optic neuropathy, posterior ischemic optic neuropathy, and ischemic optic neuropathy associated with giant cell arthritis.

In some embodiments, a potential subject is identified. For example, a subject may be a person who is identified as being at risk for dysregulated reduced CBF (TIAs) wherein a prophylactic ONS is delivered to prevent brain stoke. Additionally or alternatively, a subject may be a person who is identified as being at risk for dysregulated reduced OBF (Amaurosis fugax) wherein a prophylactic ONS is delivered to prevent eye stoke.

In some embodiments, the subject may be monitored for example, to determine when to treat, whether to treat and/or how to treat his condition. Methods may optionally include monitoring the subject for prophylactic treatment where the patients are at pre-clinical stage of the disease for example amaurosis fugax and/or transient ischemic attacks. The CBF and/or OBF of subjects who had received neuromodulation treatment may also be monitored for example to determine a need of re-treatment. For example, prophylactic treatment may be applied where the patients are at pre-clinical stage of the disease.

In certain embodiment, the ischemic brain or/ocular tissue is depleted from antioxidants, For example ascorbic acid level is markedly reduced after brain ischemic stroke. For example the oxidative damage of the ischemic tissue and penumbra of the brain is modulated and inhibited by acute intravenous administration of pharmacological doses of ascorbic acid. Ascorbic acid may enhance the activity of anti-oxidant enzymes such as catalase and superoxide dismutase providing further protection against oxidative stress to the ischemic neurovascular brain tissues. For example it protects BBB and BOB disruption thereby prevents brain/retinal edema after ischemic stroke. Additionally or alternatively ascorbate treatment inhibits glutamate excitotoxicity produced by release of intracellular glutamate from damaged neural cells of the infracted brain tissue.

In certain embodiment, intravenous ascorbic acid administration in pharmacological doses can modulate the effect of various oxygen free radicals that excessively produced by ischemia-reperfusion in a way that effectively scavenge the highly toxic reactive oxygen species such as superoxide radicals and hydroxyl radicals and leads to formation of less toxic hydrogen peroxide ($H_2O_2$). The latter can diffuse through aquaporin 3 and cell membranes to reach the ischemic brain tissues and infracted core. Supported by catalase, $H_2O_2$ decomposes to water and oxygen. This chemically produced oxygen might be tissue saving in ischemic brain stroke. Additionally or alternatively, physiological levels of $H_2O_2$ is essential and plays an important role in brain cell signaling In certain embodiment, Intravenous administration of pharmacological doses of ascorbic acid serves as a prodrug for selective delivery of $H_2O_2$ to the extracellar space. High level of $H_2O_2$ in the ischemic tissue of the brain (penumbra) may severe as a local chemical source for $O_2$ in the presence of catalase thereof acts as instant tissue saver. $H_2O_2$ can spread to ischemic penumbra and infracted core through aquaporin 3 channels releasing essential $O_2$ to nerve cells suffering from hypoxia. In other embodiment pharmacological ascorbate anti-oxidant effects protects against BBB and BOB disruption thereby prevents brain and retinal edema after ischemic stroke. Additionally or alternatively ascorbate treatment inhibits glutamate excitotoxicity produced by release of intracellular glutamate from damaged neural cells of the infracted brain tissue. In some embodiments of the present invention, ONS is configured to apply excitatory stimulation to induce acute development of leptomeningeal collateral circulation and dilate cerebral vessels at the vicinity of occlusion, thereof increases delivery of intravenously administered ascorbate to a concentration sufficient to restore physiological level of this vitamin in penumbra and infracted core. Restored physiological levels of ascorbic acid in the penumbra and or ischemic ocular tissue might minimize oxidative damage, glutamate toxicity to ischemic brain tissue and reactionary edema induced by BBB disruption.

In certain embodiment, the endothelial dysfunction is modulated by pharmacological doses of ascorbic acid. Oxidative stress plays a major role in endothelial dysfunction. The cerebral endothelium produces several vasoactive mediators such as NO. This suggests that pharmacological doses of ascorbic acid could restore endothelial function and NO-dependent vasodilatation via its anti-oxidative effects.

Currently, reperfusion with thrombolytic r-tPA remains the only treatment proved to be safe and effective when given within 3-4.5 hr after ischemia onset. Delayed use of r-tPA leads to hyper-reperfusion which resulted in the accumulation of free radicals, the up regulation of matrix metalloproteinases including MMMP-9 and destruction of BBB, and these events lead to more damage to brain parenchyma. In certain embodiment of this invention include administration of effective amount of ONS and pharmacological doses of ascorbic acid to prolong the window time for brain and ocular stroke treatment and to reduce the side effects of delayed application of r-tPA in stroke therapy.

Recently, reperfusion with endovascular therapy to remove the thrombus and restore arterial patency has been employed to treat selective cases of cerebral strokes within a limited time frame from the onset of ischemia. In certain embodiment of this invention include combined administration of effective dose of ONS and intravenous ascorbic acid to prolong the window time for brain stroke treatment by endovascular therapy and improve the functional brain recovery.

The treatment optionally increases CBF and/or OBF to the brain, retina and/or optic nerve head. The treatment optionally, improves delivery of oxygen, glucose, insulin, humoral mediators, growth factors, antioxidants, anticoagulant, and/or pharmacological agents to the targeted tissues at the brain, retina, and/or optic nerve. For example, compound may target photoreceptors (PRs) of the retina, and nerve cells of the brain.

There is further provided, in accordance with an embodiment of the present invention, a method for modifying a property of a brain of a subject, including applying ONS to a subject using vibrotactile, ultrasonic chemical optical, electrical or hybrid electro-optical energy configured to induce an increase in permeability of a blood-brain barrier (BBB) and or BRBs of the subject.

In some embodiments, the present invention provides an apparatus and a method for optical, electrical or by hybrid electro-optical stimulation of neurons of V1 in the nasal cavity to obtain a physiological response in a subject (e.g., increased CBF) and to treat cerebral stroke and acute reduced dysregulated CBF In some embodiments, one or more electrodes are placed adjacent the AEN, a branch of V1 intranasally to provide a sensitizing stimulation signal that by itself, would not be sufficient to trigger a nerve action potential (NAP), but when combined with an optical stimulation signal applied in temporal proximity, enhances the probability of triggering a desired NAP along the V1

In some embodiments, simultaneous application of both an optical stimulation signal and an electrical stimulation signal provides more efficacious generation of NAP responses in the subject than either optical or electrical stimulation alone. In addition, the much higher precision possible when using optical stimulation permits many more channels of ophthalmic nerve pathway such as unmyelinated C nerve fibers and and/or Aδ fiber neurons to be individually and distinctly stimulated than is possible using electrical stimulation alone. In some embodiments, the application of an electrical field before or during the application of the optical stimulation pulse permits more reliable generation of NAP signals than is possible using the optical signal pulse alone, and permits reliable generation of NAP signals.

In some embodiments, stem cell therapy may be combined with ONS and ascorbate treatment. The treatment includes the regulation of the subject's TVS and TABRs along with pharmacological doses of ascorbate. For example, the exogenous cell therapy might be used in the sub acute stage of cerebral/or retinal/optic nerve stroke. For example, the ONS may be administered by using a set pre-determined waveform of ONS sufficient enough to increase homing of administered stem cells at the infracted site of the brain and/or the eye. Pharmacological doses of ascorbate are important for survival of stem cells at the site of recruitment. In certain embodiment ONS is employed, wherein ONS is adapted to configure the stimulation of V1 to increase the molecular passage of a number of neurotrophic factors across the BBB and or BOBs. The said neurotrophic factors are selected from the list consisting of neurotrophic factors, including but not limited to IGF1, IGF2, GDNF, BDNF, CNTF, TGF-alpha, TGF-beta 1, TGF-beta 2, and TGF-beta 3. These factors may enhance stem cell survival and the potentiate the process of nerve tissue regeneration at the site of infarction In some embodiments of this invention include chronic ONS may be administered using a set pre-determined waveform with parameters sufficient enough to enhance motor, sensory and cognitive recovery during sub acute and chronic stages of the cerebral stroke.

In certain embodiment, the targeted autonomic circuit is modulated by increasing the parasympathetic activity via ONS and/or decreasing the sympathetic activity by pharmacologic neuromodulating agent such as intravenous administration of antioxidants to produce sympatholytic effect on the targeted autonomic circuit and/or to reduce the ocular vasomotor tone and sympathetic overactivity in brain and or the eye as a result of the stroke.

In certain embodiment, a targeted autonomic circuit is modulated by increasing the parasympathetic activity. In certain embodiment the targeted autonomic circuit is modulated by increasing the parasympathetic and/or decreasing the sympathetic activity. In certain embodiment the targeted autonomic circuit is modulated by increasing the parasympathetic/sympathetic activity ratio.

In some embodiments, treatment may be applied via a handheld device. For example, a treatment device may include a nose supported stimulator probe. Optionally a device may have a stimulator body and/or a stimulator probe. For example, the device may include one or more intra-nasal and/or extra-nasal application heads. The signal may include, for example, vibration, ultrasonic, chemical, optical, electrical, hybrid electro-optical and/or a combination of two or more of these types of stimuli.

In some embodiments, the site of stimulation of V1 includes; nasal vestibule (Septal branch of anterior ethmoid nerve AEN), nasal bridge (external nasal nerve and/or infratrochlear nerve), and forehead (supraorbital and/or supratrochlear nerve).

In some variations, the devices described here include a single module device producing one type of stimulation such as vibration. In some variations, the devices described here are bi-modular devices using two types of stimulation such as vibration and/or chemical stimulation. In some variations, the system described here are multi-modular and/or composed of a number of modules which produce various types of stimuli such as vibrotactile, chemical, photic, optogenetic, ultrasonic, or electromagnetic or electrical stimuli. The devices are handheld, or having portable body with nose supported stimulator probe. The multi-modular device is table mounted with a number of modules having various stimulating probes.

In some embodiments, treatment is applied using a single mode, hand held vibrotactile ophthalmic nerve stimulator (V-ONSor): In some variation, the handheld vibrotactile devices described here may have a stimulator body, a stimulator probe, and/or an application head. In some variations, the stimulator probe is releasably connected to the stimulator body. In some variations, the stimulator body, the stimulator probe and/or the head constitute one continuous unit with no releasable joints.

In some variation, the disposable intranasal stimulator probe includes a smooth face of the application head that comes in contact with the mucosa of the nasal septum of the vestibule. The intranasal application head comprises a polycarbonate, or any other material suitable to transmit vibration and/or reduce heat energy produced by vibration.

In some of these variations, the stimulator probe comprises at least one head. In some of these variations, the stimulator probe comprises two intranasal heads.

In some variations, the intranasal head is covered by disposable sterile thin walled cover made of rubber materials. In some variation the cover might be impregnated with TRPM8 agonist such as menthol.

In some variations, the handheld vibrotactile devices described includes, a micro pump that might be incorporated in the intranasal head with a reservoir containing TRPM 8 agonist (such as menthol) in the form of solution or soft gel. The face of the intranasal head has multiple irrigation holes through which the reservoir's contents are released in a pulsatile fashion to stimulate nasal mucosa during the session of ONS.

In some variations, the handheld vibrotactile devices described here, the head has V-shaped pattern that rests over the nasal bridge during administration of ONS.

In some variations, the handheld vibrotactile devices described here, the head has single or double or multiple heads with a flat faces that rest on one side of the forehead during administration of ONS.

In some variations, the device further comprises a user interface. In some of these variations, the user interface comprises one or more operating mechanisms to adjust different parameters of the stimulus such as the frequency of stimulus (between 20 Hz and 89 Hz.), the amplitude (more or less than 1.5 μm, the duty cycle (less or more than 50%) type of waveform (rectangular, sinusoidal, etc.) and/or the duration of session in minutes. Additionally or alternatively, the user interface may comprise one or more feedback elements.

In some variations, a stimulator comprises a rechargeable power source and/or a control subsystem to control a stimulus to be delivered to the subject via the stimulator probe application head, and/or a base station to recharge the rechargeable power source. In some of these variations, the stimulator body comprises memory to store data, and/or the base station is configured to retrieve data from the stimulator.

In some of these variations, the device is portable with portable case and/or nasally clipped application heads, with pre-programmed features designed for the use by treating doctors in clinics after establishment of ischemic stroke and prior patient referral to stroke unit.

In some of these variations, the device includes a portable nose-supported butterfly like frame glasses, with pre-programmed features designed for doctors use in clinics and emergency units after establishment of ischemic stroke and prior arrival of the patient to stroke unit.

In some of these variations, the device is hand held bi-modalular (vibro-chemical mode) with pre-programmed features designed for doctors use in clinics.

In some variations, the devices described here includes a Single Mode, portable, optical ophthalmic nerve stimulator (Op-ONSor), For example an Op-ONSor may include a single module portable devices with nose supported stimulator probe, and/or intranasal application head in the form of a tube emitting blue light (e.g. 480 nm) or red/infrared light (630-829 nm) toward the nasal mucosa. The blue light with wavelength of about 480 nm (e.g. between 475 to 485 nm and/or 460 to 470 nm) will stimulate melanopsin containing nerve fibers of V1 causing a robust vasodilator effect and/or increased OBF and/or CBF of the ipsilateral side of the stroke. In other variations the intranasal probe emits light to the nasal cavity as a whole including the nasal mucosa of the septum. One or two nasal probes are inserted into nasal vestibules for unilateral or bilateral ONS simultaneously or in succession.

In some variations, the device further comprises a user interface. In some of these variations, the user interface comprises one or more operating mechanisms to adjust different parameters of the stimulus such as the frequency of stimulus (between 10 Hz and 40 Hz.), the energy output (10 mW/cm2-100 mW/cm2), duty cycle (less or more than 50%), type of waveforms and/or the exposure time minutes (5-10 minutes).

In some embodiments, a treatment device may include a single mode, handheld, ultrasonic ophthalmic nerve stimulator (U-ONSor). For example, the device relates to pulsed ultrasonic nerve stimulation device for treating brain and ocular stroke caused by acute dysregulated reduced CBF and/or OBF via up regulation of TVS and/or TABRs through stimulation to V1 intranasally. Pulsed Low Intensity Low Frequency Ultrasound (LILFU) optionally stimulates peripheral neuron thermally and/or by mechanical ways.

Low frequency ultrasound is typically in the range of 0.3 MHz to 0.8 MHz or above. A rate of 300 Hz (or lower) may cause inhibition (down-regulation). A rate in the range of 500 Hz to 5 MHz may cause excitation (up-regulation). Power is generally applied at a level less than 60 mW/cm2.

In some variation, the handheld ultrasonic devices described here may have a stimulator body, a stimulator probe, and/or an application head. The US-ONSor stimulator body optionally contains a drive motor and/or an electronic control module. The output shaft of the drive motor typically carries an off-center weight. The shaft of the drive motor and/or the off-center weight attached to it rotate at least at approximately 30,000 rpm, creating a 500 Hertz ultrasonic frequency vibration in the application head. The application head comprised an ultrasound transducer which is typically made of a PZT-8 piezoelectric ceramic or similar material.

In some embodiments, upon activating the hand held US-ONSor, low voltage DC energy is converted into an ultrasonic frequency DC current by the electronic frequency generator module, which is connected to the ultrasound transducer. Under the influence of the ultrasonic frequency DC current the ultrasound transducer resonates, expands and/or contracts volumetrically, in tune with the frequency supplied by the electronic frequency generator module and/or thereby converting the electronic energy into ultrasonic pressure waves. These ultrasonic pressure waves are impacting nasal septal mucosa and/or stimulate septal branch of AEN.

In some variations, the device further comprises a user interface. In some of these variations, the user interface comprises one or more operating mechanisms to adjust different parameters of the stimulus such as the frequency of stimulus and/or the ultrasound power. Additionally or alternatively, the user interface may comprise one or more feedback elements.

In some of these variations, the device may be programmed according to the specific requirement needed for brain and/or ocular stroke as an example middle cerebral artery occlusion, central retinal artery occlusion (CRAO) or anterior ischemic optic neuropathy. Some or all features US-ONS can be adjusted, such as duration of session, frequency of stimulation, US power, duty cycle, pulse characters. In some embodiments, for this type of devices, only the treating doctor has the access for programming these devices.

In some embodiments, treatment is applied using a single mode, portable, electric ophthalmic nerve stimulator (E-ONSor): This invention in some embodiments thereof relates to portable transcutaneous electrical nerve stimulation (TENS) devices for increasing CBF and/or OBF for example in patients with middle cerebral artery occlusion and CRAO. More specifically, some embodiments of the invention relate to a TENS device that operates in the electrical current range of about 0.7 mA to 3.5 mA, using a frequency ranged from 10-40 Hz. The devices are configured to deliver a pulse-based electrical waveform, which might be biphasic, alternating monophasic, or monophasic or the like.

In some variations, the devices described here are a single module, with portable case, and/or disposable intranasal application head. The intranasal application head might be self supported in the form of intranasal septal clip, or extra nasal application heads with nasal bridge clips. In other variations the adhesive electrodes of the E-ONSor were applied to the forehead or upper eyelid of the subject In some variations, the devices described here are a single module, portable handheld device, comprised a stimulator body, and/or intranasal stimulator probe, with one or two intranasal application heads. In some variations, stimulator probe is disposable and/or releasably connected to the stimulator body. The intranasal head carrying one or more electrodes is simple with a smooth face that comes in contact with the mucosa of the nasal septum of the vestibule. A return electrode might be allocated on the application head in contact with skin of nasal opening or incorporated in the body of the stimulator probe In some variations, the device further comprises a user interface. In some of these variations, the user interface comprises one or more operating mechanisms to adjust different parameters of the stimulus such as the frequency of stimulus (between 10 Hz and 40 Hz.), the amplitude (0.7 mA to 3.5 mA), amplitude modulation frequency (2-2.5 Hz), pulse width (0-300 µs) Pulse width modulation (1 Hz), the duty cycle (less or more than 50%) type of waveform (rectangular, sinusoidal, etc.) And/or the duration of session in minutes (5-10 minutes). Additionally or alternatively, the user interface may comprise one or more feedback elements.

In some variations, the systems described here, the stimulator body comprising a rechargeable power source and/or a control subsystem to control a stimulus to be delivered to the subject via the stimulator probe head, and/or a base station to recharge the rechargeable power source. In some of these variations, the stimulator comprises memory to store data, and/or the base station is configured to retrieve data from the stimulator. Additionally or alternatively, the stimulator probe is irremovably connectable to the stimulator body.

In some variations, the methods described here comprise methods for treatment of acute ocular disorders such as CRAO. In some variations, the standard protocol of ONS is administered hourly in the first 6 hours, and 3 hourly thereafter during the 1st 3-4 days coupled with normobaric $O_2$ therapy and intravenous administration of pharmacological dose of ascorbic acid (acute stage).

In some variations, the methods described here comprise methods for treatment of acute brain disorders such as middle cerebral artery occlusion. In some variations, the standard protocol of ONS is administered hourly in the first 6 hours, and 3 hourly thereafter during the 1st week coupled with normobaric $O_2$ therapy and intravenous administration of pharmacological dose of ascorbic acid (acute stage).

There is yet additionally provided, in accordance with an embodiment of the present invention, a method for treating an ischemic brain stroke of a subject, including: the use of mechanical thrombolysis via endovascular recanalization or administering a tissue plasminogen activator to the subject; applying ONS to a site of the subject selected from the group consisting of: nasal septum, nasal bridge, or and/or forehead; and configuring the stimulation to excite nervous tissue of the site at a strength sufficient to induce an increase in permeability of a blood-tumor barrier (BTB) of the subject, but insufficient to induce a substantial increase in permeability of a blood-brain barrier (BBB) of the subject. Additionally or alternatively application ONS along with effective leptomeningeal collateral circulation and preventing hemorrhagic transformation mechanical and/or r-tPA thrombolysis may improve the functional outcome via acute development of effective leptomeningeal collateral circulation and preventing hemorrhagic transformation.

Illustrative embodiments of the invention, in some embodiments thereof, are described herein. It will be apparent to those skilled in the art, that is, to those who have knowledge or experience in this area of technology, that many uses and/or design variations are possible for the devices for V1 stimulation. The following detailed discussion of various alternative and/or preferred features and/or embodiments will illustrate the general principles of the invention, in some embodiments thereof, with reference to non-invasive devices for stimulating V1. It is important to point out that not all features of an actual implementation are described in this specification. In the development of any such actual embodiment, numerous implementation-specific decisions may be made to achieve the design-specific goals, which will vary from one implementation to another. It will be appreciated that such a development effort, while possibly complex and/or time-consuming, would nevertheless be a routine undertaking for persons of ordinary skill in the art having the benefit of this disclosure. Other embodiments suitable for other applications will be apparent to those skilled in the art given the benefit of this disclosure.

Unless otherwise defined, all technical and/or scientific terms used herein have the same meaning as commonly understood by one of ordinary skill in the art to which the invention pertains. Although methods and/or materials similar or equivalent to those described herein can be used in the practice or testing of embodiments of the invention, exemplary methods and/or materials are described below. In case of conflict, the patent specification, including definitions, will control. In addition, the materials, methods, and/or examples are illustrative only and/or are not intended to be necessarily limiting.

Implementation of the method and/or system of embodiments of the invention can involve performing or completing selected tasks manually, automatically, or a combination thereof. Moreover, according to actual instrumentation and/or equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Some embodiments of the invention are herein described, by way of example only, with reference to the accompanying drawings. With specific reference now to the drawings in detail, it is stressed that the particulars shown are by way of example and/or for purposes of illustrative discussion of embodiments of the invention. In this regard, the description taken with the drawings makes apparent to those skilled in the art how embodiments of the invention may be practiced.

In some embodiments, the methods disclosed herein include stimulating V1 by different methods including vibrotactile, chemical, ultrasonic, optical, electrical and/or hybrid electro-optical methods. The stimulating agent will stimulate branches of V1 directly, or indirectly providing sensory information back to the CNS and/or ocular blood vessels, pancreas or the nasal mucosa and/or sub-mucosa. With that approach, neural tissue may be activated in some manner. For example, referring to FIG. 5, without limiting the ideas to a theoretical framework, a possible mechanism of action includes that the activation at an intra-nasal 502 or extra-nasal locations 504, 506, 508, 510 may cause action potentials to run antidromically back to the eye (arrow 1) or brain blood vessels, as shown in FIG. 2A and FIG. 2B, and/or orthodromically from the activation point to cause sensory input to the brain (arrow 2). Sensory input to the brain reaches the brain stem, after passing several ganglia on the way, as shown by arrow 2. Accordingly, the activation of neural tissue, directly or indirectly, may cause circuitry in the CNS (e.g., brain, potentially the ganglia in the peripheral cranial nervous system) to respond to the input. Output from the brainstem may then send feedback, as shown in FIG. 2, FIG. 3 and FIG. 4 to the brain and/or the eye and/or cerebral arteries and/or ophthalmic artery branches causing increased CBF and/or OBF and or to the pancreas to increase insulin secretion.

In some embodiments, the devices and/or systems may be configured for non-invasive stimulation of branches of V1. The devices may be single mode devices or multi-modal systems. The methods may further comprise treating ocular disorders by regular activation of the TVS and/or TABRs through up regulation of PNS, and/or restoring autonomic balance and/or this aimed to enhance the neural plasticity and/or maintain long term effects.

Single Mode Devices

In some variations, the devices may comprise a single mode for ONS. The device delivers one type of ONS include exemplary embodiments of vibrotactile ONSor devices 600, 800, 900, Ultrasonic ONSor device 1400, optical ONSor device 1500 and 1600, Electrical ONSor device 1900, 2000 and/or Electromagnetic ONSor device, When the devices and/or systems are used to treat brain, retinal, and/or optic nerve acute ischemic disorders the methods may comprise stimulating V1 to increase CBF and/or OBF, restore lost function, or improve brain and ocular health. Optionally single mode devices are designed for physician use in clinics, emergency departments and stroke specialized units. Additionally, it can be used in clinics and/or eye hospitals by professional ophthalmologist and/or medical staff.

Multimodal Machine

In some variations the stimulation system described here may comprise two modules, (e.g. vibro-chemical module 1300, hybrid electro-optical module 1700 and 1800). In some variations the stimulation system described here may comprise of combination of two or more modules (Multinodular device 2100) that produces vibrotactile, chemical, ultrasonic, light based, electrical, electromagnetic or the like. When the devices and/or systems are used to treat brain strokes and or acute ischemic ocular disorders such as CRAO, ischemic optic neuropathy, the methods may comprise stimulating V1 to increase CBF/or OBF, prevent progression of ischemia and loss of function of affected brain or ocular tissue. Optionally, Multinodular systems 2100 are designed for hospitals, institutions, and/or clinics for use by professional neurologists and ophthalmologist or by other medical staff supervised by experienced doctors.

The Intranasal Pathway

A challenge of intranasal ONS was to make the application head small enough to fit comfortably and/or safely within the restricted size of the nasal vestibule. Intranasal pathway may have many potential advantages which include presence of plenty of different types of receptors on sensory nerve fibers of V1 that make stimulation of these receptors easier and/or more effective. V1 exhibits mechanosensory and/or chemosensory and/or photo sensory nerve fibers and/or their specific receptors (e.g. mechanoreceptors, TRPM8, Melanopsin) in the nasal cavity that may makes vibrotactile and/or chemical and/or optical stimulation more selective and/or effective and/or might prove to have synergetic effects. Mechanosensory fibers are represented by large fast-conducting Aβ-fibers. Chemosensory fibers refer to thin and/or slow-conducting unmyelinated C-fibers and/or thin, fast-conducting myelinated Aδ-fibers that are involved in thermoreception (temperature perception) and/or nociception. Electrophysiological data indicate that an area of increased trigeminal chemosensitivity might be found at the anterior third of the septum. The presence of melanopsin containing nerve fiber in the trigeminal nerve makes V1 a natural target for optical stimulation to increase CBF/OBF. Furthermore, administration of vibrotactile, chemical, photic, ultrasonic, electrical and/or hybrid electro-optical stimulation trans-nasally may be advantageous as they may be located closer to important targets to be stimulated. This include AEN, SPG and/or midbrain area where much of the autonomic functions lie, with little barrier in between the source of stimulus and/or the target.

Site of Stimulation

FIG. 5 illustrates some preferred sites for ONS. The site of stimulation includes nasal vestibule 502, nasal bridge 504, forehead and/or eye brows 506.

The nasal vestibule is the most anterior part of the nasal cavity. It is enclosed by the cartilages of nose and/or lined by keratinized stratified epithelium composed of basal cells along the basal lamina and/or several layers of squamous cells, which become progressively flatter toward the luminal surface. The other part of the nasal cavity, which is lined by the respiratory epithelium, is called nasal cavity proper. The mucosa of the anterior part of nasal cavity 502 receives sensory nerve supply from AEN, a branch of nasociliary nerve of V1. The AEN runs through the cribroethmoidal foramen and/or then passes forward and/or downward along the border between the nasal septum and the lateral wall of the nose. A preferred site for stimulation at the nasal vestibule is the anterior part of nasal septal area which is supplied by septal branch of AEN.

The upper nasal bridge 504 is a convenient site for stimulation of V1. It is innervated by infratrochlear nerve, a branch of nasociliary nerve. The lower part of nasal bridge is supplied by external nasal nerve, the terminal branch of external branch of anterior ethmoid nerve, which is a branch of nasociliary nerve.

The skin of forehead 506 is innervated by supratrochlear and/or supraorbital nerves, branches of frontal nerve. The latter is a branch of V1. This site of stimulation may be suitable for patients with a history of nasal trauma or nasal septal surgery, and/or probable nerve damage to AEN.

Type of Stimulation

The signal may include vibration, chemical, ultrasonic, photic, optogenetic, electrical, electromagnetic or combination between two or more of these types of stimuli.

Electrical stimulation may be effective for triggering neurons. Stimulation by vibration may be used in some embodiments as an alternative technique for V1 stimulation. It may include selective stimulation mechanoreceptors and/or of nerve fibers according to vibration frequency.

In some embodiments, facial vibrotactile stimulation (i.e., approximately 89 Hz frequency and/or approximately 1.9 μm amplitude) might activate PNS. This setting may produce pupillary constriction, salivation, bradycardia and/or biggest P-R intervals. Subjects may show a decrease in pulse frequency during 89 Hz-vibrotactile face stimulation compared to during 114 Hz-face stimulation. Constant mechanical vibration applied to the skin may induce hypoesthesia, specifically, a reversible decrease in the perception of vibration at the stimulated site. This phenomenon may be defined as vibrotactile adaptation and/or is generally characterized by an increase of vibrotactile detection threshold or a reduction of vibrotactile sensibility. Without limiting the invention to a theoretical framework, according to two-channel theory, the transduction of low-frequency vibrations (10-60 Hz) is preferentially achieved by rapidly adapting type I (RA) and/or slowly adapting type I (SAI) mechanoreceptors whereas the transduction of high-frequency vibrations (200-300 Hz) is preferentially achieved by rapidly adapting type II Pacinian (RAII/PC) mechanoreceptors. For example, vibrotactile stimulation with a frequency of 20-89 Hz may be employed for of ONS in order to avoid rapidly adapting type I mechanoreceptors.

Vibrotactile Ophthalmic Nerve Stimulator 600 (V-ONSor 600)

FIG. 6 shows an exemplary diagram of a hand held VONSor 600. V-ONSor 600 is a single mode hand held device. The devices may comprise a stimulator body 602 and/or a stimulator probe 604 as illustrated in FIG. 6, where the stimulator probe ended with different types of stimulator probe application heads as shown in FIG. 7.B. 752, 754, 756, and/or 758. Generally, the stimulator body 602 in FIG. 6 may be configured to generate a stimulus that may be delivered to the subject. The stimulator body 602 may comprise a front housing, back housing, and/or two side housing 608, which may fit together to define a body cavity 610, base 612, The body cavity 610 may contain a vibration power source 620 and/or control subsystem 624 and, which together with the user interface 618 located at the front housing may generate and/or control the vibrotactile stimulus.

FIG. 7A illustrates a Stimulating probe 700 which may be push-fitted onto the body of the stimulator and/or the drive shaft of the V-ONSor 600. The stimulator probe 700 includes a mounting tube 702 extending in the direction of a longitudinal axis 720. At its free end close to the body of stimulator, the mounting tube 702 has a profile ring 708 with an inside contour 710 complementary with the outside contour of the body of stimulator. The inside and/or outside contours may be of a square, stellate or similar configuration when viewed in cross section, optionally the inside and outside contours are conformed to each other. In this manner, the stimulator probe 700 can be push-fitted onto the body of the stimulator in a manner inhibiting relative movement, while at the same time a secure seat of the stimulator probe 700 on the body of the stimulator is ensured. At its end remote from the body of the stimulator, the mounting tube 702 has a bearing 704 in which a shaft 712 is carried so as to be vibrating at the level vertical to the shaft. The shaft 712 is arranged in the longitudinal axis 720 of the mounting tube 702 and/or is preferably made of metal. The shaft 712 extends from the bearing 704 in the direction close to the body of stimulator approximately up to the center of the mounting tube 702. At its end remote from the body of the stimulator, the mounting tube 702 has a cap structure covering approximately the area by which the shaft 712 projects beyond the bearing 704 and/or thus beyond the mounting tube 702. Further arranged in this area are an application head 706 of the stimulator probe 700 as well as means for coupling the application head structure 706 to the shaft 712 and/or to the mounting tube 702. The application head structure 706 includes a disk-shaped plate 714 and/or a hub 716 and/or is essentially vibrating along the axis 722 disposed at an angle of about 90 degrees to the longitudinal axis 720. On its side facing away from the shaft 712, the plate 714 has a slightly curved smooth surface 718 covered by polymethyl methacrylate. When the V-ONSor 600 is turned on, the drive shaft 622 projecting outwardly from the body of stimulator produces a vibration movement 724 coincides with the axis 722 and/or vertical to the longitudinal axis 720 and/or to the shaft 712 of the stimulating probe. In consequence, the application head executes a vibration movement along the axis 722. This means that the application head 706 performs approximately a forward and/or backward movement. This vibration movement produced by the application head of the stimulator probe 706 is employed to execute mechanical stimulation of the intranasal 502 or extra-nasal locations 504, 506 during vibrotactile ONS. The stroke length of the vibrating back-and forth motion 724 may advantageously lie in a range from about 1.5 mm to about 3.0 mm. The frequency of the vibration may be between about 10 Hz and/or about 89 Hz, in particular at about 45 Hz FIG. 7B illustrates exemplary types of stimulator probe for portable hand held V-ONSor 600. In some variations, the intranasal stimulator probe 752 may comprise at least one intranasal head, which may be configured to be easily inserted into the nasal cavity and/or come in contact with the nasal septum of the nasal vestibule of a subject or patient. In the handheld V-ONSor 600, the stimulator probe 754 may comprise two intranasal application heads in a way that the heads come in contact with mucosal lining of the nasal septum of both nasal vestibules.

In some variations, the stimulator probe may comprise a V-shaped head 756 for stimulation of the nasal bridge. Optionally, a facet is present on some arms and/or each arm of the V shaped head. The two limbs with their facets hold and/or contact the nose from sides, while the connecting point of the two arms rest on the nasal bridge.

In some variations the stimulator probe 758 may comprise two or more heads that can be applied simultaneously to touch both sides of the forehead.

In some variations, the stimulator probe described here may comprise a thin silicone cap to protect the stimulator probe and/or its application head. For example, FIG. 7C show different types of silicone caps that can fit to various types stimulator heads. As shown there, the cap 772 may fit over the stimulator probe 752, while the cap 774 may fit over both the stimulator probe 754 and/or 756. The cap 776 may be suitable for stimulator probe 758. More particularly, for intranasal stimulator probes, it may be desirable for the cap to protect the nasal insertion site from contamination.

In some variations, the cap might be impregnated with a TRPM8 agonist such as menthol. In some variations, the cap may be translucent or transparent, while in other variations, the cap may be opaque for discreteness.

In some embodiments, a stimulator probe 604 may be detachable. The connection 634 between the detachable probe and/or the rest of the device is optionally made in a manner to facilitate transmission of vibration from the stimulating body 602 to the head 606 of stimulator probe 604.

In this variation, the stimulator probe is covered by simple sterile disposable silicone cap. In some variation, the cap might be impregnated with chemical substances that stimulate the V1 chemically such as menthol. In some variations, no parts of the device are disposable.

In some embodiments, a stimulus may be delivered to a subject via the head 606 of stimulator probe 604. The stimulator body 602 and/or stimulator probe 604 may be reversibly attachable. In variations where the stimulator probe and/or the stimulator body are not detachable, the stimulator probe is covered by disposable sterile cap. Detachable stimulator probes are optionally disposable. Detachable stimulator probe is optionally sterile and/or disposable. In some variation, a chemical micro pump might be incorporated with the detachable stimulator probe. The head shape varies according to the site of stimulation. FIG. 7B. shows types of application heads for vibrotactile stimulation 752, 754, 756, 758.

The stimulator body 602 may comprise housing 608, a user interface 618, a control subsystem 624, and/or a power source 628.

FIG. 6 shows a perspective view, of the stimulator body 602. The stimulator body 602 may have any suitable shape, such as cylindrical or tetragonal with blunted edges. In some variations, it may be desirable for the stimulator body 602 to be shaped such that it can be easily gripped by a user, such that it can be held with one hand. However, it should be appreciated that the stimulator body may have other shapes.

FIG. 6, a stimulator body 602 may have a flat base 512 ends with a circular small tunnel for energy connection 614 and/or a tapered proximal end that gives attachment to the stimulator probe 604. In some variation, the proximal end of the body 602 is continuous with the stimulator probe 604 with no joint between them.

For example, as mentioned above, the stimulator tetragonal body may comprise a housing 608. The front housing may also comprise an opening configured to receive a number of small lights 616 (4 lights) that give an indication of status of battery. In some instances, it may be desirable for the stimulator body to be sealed, such that it may be waterproof or the like. In variations in which the housing comprises openings for other elements of the stimulator body (user interface, electrical connection at the base of the body, or the like), the interface between those elements and/or the stimulator housing may be watertight, and/or may comprise seals.

In some variations, housings may comprise a thermoplastic such as acrylonitrile butadiene styrene (ABS), polycarbonate, polyetherimide. However, the housing may comprise any suitable material or materials.

The stimulator body 602 may comprise a user interface 618 comprising one or more operating mechanisms to adjust one or more parameters of the stimulus. For example, the operating mechanisms may allow the user to power the device on or off, start or stop the stimulus, change the frequency of the stimulus, change the duty cycle, change the duration of the stimulus, change the stimulus pattern, or the like. In some variations, the user interface may comprise one or more operating mechanisms, which may allow the user to use a predetermined protocol. Another function (lock and/or unlock function). This function is used to lock changes in the setting prior treatment to avoid accidental finger touch of the user to the user interface that might interfere with any function during the session of treatment. For intentional modification of the setting, unlock button might be used. In instances where the stimulators described here comprise a user interface, the user interface may comprise one or more ways of alarming signal to indicate the end of session such as an alarming sound. The number and/or locations of illuminated status indicators 616 may indicate the charging status of rechargeable battery; the color (e.g., red) of the illuminated status indicator(s) may indicate a low battery. The operating mechanisms may provide information to the control subsystem, which may comprise a processor, memory, and/or stimulation subsystem.

It should be appreciated that while the user interfaces 618 described above are located on the stimulator body 602, in other variations, all or a portion of the user interface of the stimulator may be located on a separate unit, which may be physically or wirelessly attached to the stimulator.

In some embodiments, a control subsystem 624 may be configured to control a stimulus to be delivered to a subject via the stimulator probe. The control subsystem 624 may be contained within the housing of the stimulator. The control subsystem may be connected to the operating mechanisms of the stimulator which may allow the control subsystem to receive input from a user. The communication subsystem may be configured to facilitate communication of data and/or energy between the stimulator and/or an external source. Additionally or alternatively, some or all of the safety mechanisms of the control subsystem may be part of the processor. For example, the processor may comprise software that limits the frequency within an allowed range. In some variations, the frequency may be limited between about 10 Hz and/or about 30 Hz, between about 10 Hz and/or about 60 Hz, between about 25 Hz and/or about 89 Hz.

Power Source: The stimulator may comprise a power source. The power source may be any suitable power supply capable of powering one or more functions of the stimulator, such as one or more batteries, capacitors, or the like. As shown in FIG. 6, in some variations the power source may comprise a lithium coin cell battery. The battery 628 may be secured in place via any suitable method. In some variations, the power source may be rechargeable using a suitable charger 630.

In some embodiments, the stimulator body 602 comprises a power source, in other variations the stimulator body need not comprise a power source. In some variations, the stimulator body may comprise a port, cord 632, or other mechanism for connecting the stimulator to an external power source (such as a wall outlet or separate battery pack), which in turn may be used to power one or more portions of the stimulator. In some other variations, such a port, cord, or other mechanism may be used to recharge a rechargeable power source. The stimulator body 602 may comprise such a port (e.g., a USB port) at any suitable location in the housing.

In some variations the stimulators described here may be configured to connect to an external device, such as a mobile phone or a computer, or the like. In some variations, the stimulators may use a wireless or wired connection to connect to the internet, via which they may be connected to an external device.

Portable V-ONSor 800 with Nasally Clipped Application Heads

FIG. 8 illustrates one embodiment of the present invention wherein the V-ONSor 800 consists of a portable control unit 800 and/or vibration producing device 850. In this particular embodiment the case or housing of the control unit is equipped with a clip 812 that allows the unit to be worn on the shirt pocket or belt or the like during use. The other side of the case relative to the belt clip is equipped with a display 804 (user interface) which may be a touch screen that allows the user to adjust different parameters of the vibrotactile stimulus such as the frequency, amplitude, pulse width, shape of waveform etc., and/or modulating these parameters or select preset features of the stimulus. In some variations the system 800 delivers vibrotactile stimulation from application head 852 of the vibration producing device 850. The Control unit 800 of the system communicates with the vibration producing system 850 via power coupling 818. In some embodiment there are one or two vibration producing devices and/or both are connected to the control unit 800 via power coupling 818, 820. The application head 852 is designed to have round shaped tip that can be inserted easily in the nasal cavity and/or can be maintained in contact with nasal mucosa via nasal clips 854.

In some embodiments, the top face of the case 802 is further provided with an on/off switch 810 and/or a two power coupling 818, 820 connecting the vibration producing device 850 and/or the control unit 800 by two power outlets 814, 816 provided on the top face of the case 802. During administration of vibrotactile ONS, typically application head 852 is inserted into one nasal vestibule, touching the nasal mucosa of the septum and/or held in place via nasal clips 854.

In some embodiments, for example as shown in FIG. 8, the vibration producing device 850 comprises an application head 852 for providing vibrotactile stimulation to the nasal cavity in accordance with one embodiment of the present invention. The vibration producing device 850 in this embodiment generally includes a housing 856 and/or a vibration producing motor 858 positioned in or near the housing. The application head 852 is configured to be inserted into a target nasal cavity to stimulate V1 by administration of vibrotactile to the nasal mucosa of the nasal septum In some embodiments, housing 856 of the vibrotactile producing device 850 can be held in place by nasal clip 854 for an extended period of time (therapeutic time) without undue effort or discomfort, due to the lightweight, portable design of the device.

As will be appreciated by those skilled in the art, it may be desirable to control variables or control parameters associated with the output of the vibrotactile producing device 850. Examples of such variables include power, timing, frequency, duty cycle, shape of waveform. In one embodiment, the control circuit 860 controls the delivery of power from the power supply through the power coupling 1818 or 1820 to the vibration producing device 850 according to the activation or status of the controller 800. For example, in one embodiment, the control circuit 860 includes a relay, or a transistor. When the button 810 switch of the control unit 800 is pressed or activated, power from the power supply is able to flow through the control circuit 860 and/or the vibration producing system 858. For delivering a dose of vibrotactile ONS, a preset of waveform is selected, the application head is inserted into the nasal cavity, and/or the system is activated for specific duration. Vibrotactile ONS may be delivered into the nostrils of the ipsilateral side of the stroke. However, in cases where the stroke affects both sides, ONS is delivered to both sides in succession using single application head, or simultaneously using two application heads, with one application head is inserted into each nostril Portable Self Supported V-ONSor 900

FIGS. 9A, 9B illustrate another version of a portable self supported V-ONSor 900 in the form of a butterfly like a glasses frame. The stimulator comprised two pairs of wings and/or a centrally located simulator body 902. In some variations, it may be desirable for the V-ONSor 900 to be self supported and/or easily adapted over the nasal bridge and/or fixed to the head of the subject using an adjustable elastic band 950 around the head circumference. The stimulator body 902 may comprise housing 914 a user interface 916, a control subsystem connected to control buttons 918 and/or a power source 920.

In some variations, the stimulation might be delivered by an inverted V-shaped application head 908 that rest over and/or stimulate the nasal bridge. The two arms of the V-shaped application head 908 with their facets hold and/or contact the nose from both sides, and/or the connecting point of the two arms rest over the nasal bridge.

In some variations, the V-ONSor 900 might be delivered vibrotactile stimulation intranasally via two intranasal application heads 910. In this case the vibrotactile stimulation is transmitted via two limbs 922 extending from the inferior part of the stimulator body as an extension of inverted V-shaped nasal bridge application head 908. At each end of these two limbs, an application head 910 is located and/or designed in a way to come in contact with the nasal septal mucosa.

In some variations, the V-ONSor 900 might be delivered vibrotactile stimulation to forehead via one or more forehead application heads 912 which are located at the end at rear wings of the stimulator.

The application heads 908, 910 and/or 912; of V-ONSor 900 are maintained in close contact with sits of stimulation by weight bearing effect the stimulator body 902 on the nasal bridge and/or the tension of an adjustable elastic band 952 that surround the circumference of the head. Ends 954 of the elastic band 952 are attached to the stimulator at an attachment sits 924, and/or its length and/or tension is adjustable using a metallic adjustment unit 956.

The stimulator may comprise a power source. The power source may be any suitable power supply capable of powering one or more functions of the stimulator, such as one or more batteries, capacitors, or the like. As shown in FIG. 9A in some variations the power source may be rechargeable through any suitable electrical adaptor 920. The number of illuminated status of light indicators 926 may indicate the charging status of any rechargeable battery.

Features of the waveform: FIG. 10A illustrate basic features of square waveform, which include amplitude 1006, pulse width 1008, periods of on time 1002, and/or period of off time 1004. The vibration stimulation waveforms delivered by the stimulators described herein may be having different features and/or specifications. These include the shape, frequency, and/or amplitude, pulse width, with fixed or variable features. The waveform described herein may be having different shapes as shown in FIG. 10B; these include, square wave 1010, the saw tooth wave 1012, the triangular wave 1014, and/or the sine wave 1016.

Modulation of Parameters of waveform: As is described in more detail herein, the employed stimulation waveforms parameters might be fixed or modulated. The shape, frequency, amplitude, and/or the pulse width may be modulated over time. The waveform may be modulated linearly, exponentially at random or in regular basis. Modulation of stimulus parameters is optionally aimed to improve the efficacy of the stimulation, improve the clinical outcome of ONS and/or to prevent patient habituation to the applied stimulation (i.e., may help to prevent mechanoreceptor adaptation to vibrotactile stimulation)

Transition during modulation: In some variations the transition of modulation of the waveform may be gradual such as gradual increase or decrease in the amplitude of stimulus. These increases and/or decreases may have any suitable form, such as linear increases and/or decreases or sinusoidal increases and/or decreases. In other variations, the transition may have a saw tooth shape; in other instances, the modulation of the waveform might be presented in an abrupt fashion to prevent or reduce patient habituation to the applied stimulation and/or to improve the efficacy of the stimulation.

Age and/or Duration of Starting Session: The duration of sessions in the course of vibrotactile ONS might vary according to the age of the patient. In some instances, it may be desirable to increase the duration of session in older age group of patients compared to children and/or young adults in order to promote the therapeutic effect. The number of mechanoreceptors and/or degree of their sensitivity of these receptors is decreased by aging. The amplitude of stimulation might also be increased in older age group for the same purpose.

Ramping up and/or ramping down: In some instances, the waveforms described herein may be delivered during the whole session of stimulation without any change in its features as shown in FIG. 10C; 1022. In stimulation bursts may be delivered periodically at regular or irregular intervals. The stimulation amplitude, pulse width, or frequency may be modified during the course of stimulation. For example, the stimulation amplitude may be ramped from low amplitude 1020 to higher amplitude 1022 over a period of time. In other variations, the stimulation amplitude may be ramped from high amplitude 1022 to lower amplitude 1024 over a period of time. The stimulation pulse width

1030 may also be ramped from a low pulse width to a higher pulse width over a period of time as shown in FIG. 10.D. The stimulation pulse width may be ramped from a high pulse width to a lower pulse width over a period of time. The ramp period may be between 5 second and/or 30 seconds. The ramping up or ramping down time might be longer or shorter than this figure.

Frequency: In order to treat cerebral or ocular stroke or otherwise produce an increase in CBF and/or OBF by administration of ONS, the stimulators described herein may be configured to generate one or more waveforms at frequencies suitable for stimulating V1 for specific purpose. Generally, the frequency is preferably between about 10 Hz and/or about 89 Hz. This frequency is chosen to activate TVS, TABRs, TVR and or PNS. In some of these variations, the frequency is preferably between about 30 Hz and/or about 60 Hz. In others of these variations, the frequency is preferably between about 50 Hz and/or about 70 Hz. In some variations, the frequency may be about 10 Hz, about 15 Hz, about 20 Hz, about 25 Hz, about 30 Hz, about 35 Hz about 40 Hz, about 45 Hz about 50 Hz, about 55 Hz about 60 Hz, about 65 Hz about 70 Hz, about 75 Hz, or about 80 Hz. about 85 Hz, or about 89 Hz. The frequencies described herein may be suitable for stimulating the targeted tissue to initiate a reflex circuit that activates TVS and/or TABRs in order to increase CBF and/or OBF and/or suitable for directly driving efferent fibers innervating the cerebral arteries, leptomeningeal collateral circulation, ophthalmic artery, ciliary and/or choroidal arteries.

Amplitude: In order to treat acute brain and/or ocular ischemic disorders or otherwise produce an increase of CBF and/or OBF by stimulating V1, the stimulators described herein may be configured to deliver vibrotactile stimulus with suitable amplitude. The sensitivity of mechanoreceptors is decreased by aging. Therefore, the amplitude of vibrotactile stimulus might be higher for older people compared to children. In some variations the amplitude may be between about 1.5 μm and/or about 3.0 μm. In other variations, the amplitude may be variable. For example, the amplitude may vary between about 1.5 μm and/or about 2.0 μm, about 2.0 μm and 2.5 μm, about 2.5 μm and/or about 3.0 μm. For example, the stimulation amplitude may be ramped from low amplitude 1020 to higher amplitude 1022 over a period of time as shown in FIG. 10.C.

Modulation of Amplitude: In some variations, the amplitude of the stimulus may be constant over time. In other variations, the amplitude of the stimulus may vary over time. This may reduce patient accommodation. In some variations, the amplitude of stimulus may increase (linearly, exponentially, etc.) from a minimum value to a maximum value, drop to the minimum value, and/or repeat as necessary FIG. 10C. In some variations, the amplitude of the pulses may vary according to a sinusoidal profile. Each of these types of amplitude modulation may be implemented alone or in combination with any other type of amplitude modulation, and/or may reduce patient accommodation.

Frequency of amplitude modulation: In some variations in which the amplitude varies over time, the amplitude may vary at a frequency suitable for reducing patient accommodation or increasing patient comfort such as between about 0.1 Hz and/or about 5 Hz, between about 1 Hz and/or about 5 Hz, between about 1 Hz and/or 2 Hz, between about 2 Hz and/or 3 Hz, between about 3 Hz and/or 4 Hz, or about 4 Hz and/or 5 Hz.

Duty cycle and/or pulse width: A duty cycle is the fraction of one period in which a signal active. Duty cycle is commonly expressed as a percentage or a ratio. A period is the time it takes for a signal to complete an on-and-off cycle. For ONS protocol, 50% duty cycle is considered. A 50% duty cycle means the signal is on 50% of the time but off 50% of the time. The "on time" for a 50% duty cycle could be a fraction of a second depending on the length of the period.

The pulse width duration 1030: In order to treat acute brain and/or ocular strokes or otherwise increased CBF and/or OBF response by ONS, the stimulators described herein may be configured to deliver a waveform in which the pulse width lies between 5 ms and/or about 10 ms. The width of stimulus might be used to target specific nerve fibers. Larger-diameter nerve fibers of the trigeminal nerve might be activated by smaller-pulse width, while larger-pulse width might target the smaller nerve fibers (e.g., a-delta fibers, c fibers, sympathetic and/or parasympathetic fibers), In some variations, the pulse width may be constant over time. In other variations, the pulse width may vary over time. Pulse width modulation over time as seen in FIG. 10D may increase the efficacy and/or comfort of the stimulation. In some variations, the pulse width may ramp up from a minimum value to a maximum value, ramp down to the minimum value. In some variations, the pulse width may vary according to a sinusoidal profile.

On/Off Periods: On-time and/or off-time parameters may be used to define an intermittent pattern in which a repeating series of signals is generated for stimulating the V1 during the on-time (such a sequence may be referred to as a "pulse burst"), followed by a period in which no signals are generated and/or the nerve is allowed to recover from the stimulation during the pulse burst. The on/off duty cycle of these alternating periods of stimulation and/or no stimulation may have a ratio in which the off-time may be set to zero, providing continuous stimulation. Typically, however, the ratio off-time/on-time may range from about 0.5 to about 10. Exemplary on/off durations include without limitation, 4 second on/1 second off, 5 seconds on/1 second off, 6 seconds on/1 seconds off, 7 seconds on/1 seconds off.

Exemplary Waveforms: It should be appreciated that any of the above waveform parameters and/or variations in parameters may be combined to generate a temporally patterned waveform as described herein, and/or these waveforms may be delivered by the stimulator described herein. For example, the waveform comprises pulse which may have any suitable frequencies, pulse widths, and/or amplitudes. The stimulation amplitude, pulse width, and/or frequency may be the same from pulse to pulse, or may vary over time. Combinations of these parameters may increase the efficacy and/or comfort of stimulation.

Programming of the device: Certain parameters of the vibrotactile stimuli generated by the V-ONSor 600, 800, 900 are programmable. Programming the neurostimulator may be performed in a variety of manners, including those known to persons skilled in the art having benefit of the present disclosure.

Programming for safety: There are a number of safety measures that may be taken into consideration before releasing the device for individual use. One example is the frequency of waveform. The frequency is limited between 10-89 Hz. Higher frequencies might stimulate the sympathetic system and/or cause vasoconstriction of cerebral/ocular blood vessels and/or decreased CBF/OBF. Moreover, high frequency might induce tachycardia or arrhythmia.

Programming for function and/or improved efficacy: Different acute brain ocular ischemic disorders might need different set up of waveform parameters. In one particular example such as an initial poor response to ONS, a stimulator described herein may be configured to deliver a plurality of different waveforms each having a combination of one or more of shape modulation, maximum amplitude modulation, pulse width modulation, and/or frequency modulation, as described herein, to improve the clinical outcome.

Saved Waveform Settings: Some variations of the stimulators described herein may be configured with a number of stimulation waveforms. In some variations, a preferred set of waveforms is selected according to the age of patient, type and staging of the ischemic disorder, and/or the history of nasal trauma or surgery. In some variations, random selection of a different waveform each time is employed to decrease the risk of patient's accommodation to any of waveform of particular stimulation pattern.

Selective waveform for different types and stages of the disease: The vibration stimulation waveforms delivered by the stimulators described herein may be tailored for specific treatment regimens according to the staging of the disease and/or specific type of acute brain and or ocular ischemic disorders. In variations of stimulators configured to deliver vibration, different waveforms may be delivered via stimulator, and/or the delivered waveform may be changed over time. The suitable waveform is defined according to the clinical outcome of these signals.

Chemical Ophthalmic Nerve Stimulator (Ch-ONSor 1100)

Ch-ONSor 1100 is —Single Mode, Hand Held Device. The present invention, in some embodiments thereof, is based on the interesting finding that a TRPM8 agonist can stimulate the V1 and/or further that the same TRPM8 agonist can increase CBF/OBF as a treatment of cerebral stroke via a reflex induced increased CBF/OBF possibly by activation of TVS and parasympathetic system.

The TRPM8 channel is a nonselective cation channel found on lightly myelinated and/or unmyelinated A-delta and/or C primary afferent neurons. They are expressed in trigeminal neurons and/or dorsal root ganglion (DRG) neurons. TRPM8 channels are activated by moderate cold (15-30° C.) and/or by cooling compounds, such as menthol and/or icilin. A low concentration of menthol increased the activity of cool cells, whereas a high concentration caused these neurons to inactivate after a brief period of activity.

Nasal vestibule is a strong reflexogenic and/or preferable site for vibrochemical ONS as this location has the following features; a) easy accessibility B) Increased vibro-chemical sensitivity of mucosa of nasal cavity as indicated by an electrophysiological study, whereas anterior third of nasal septum reacts more to chemical compared to mechanical stimulation of V1. c) Menthol sensitizes peripheral afferents and/or trigeminal neurons to cold stimulation and/or mechanical stimulation. d) Characterization and/or cloning of trigeminal sensory neurons revealed that 55% of these neurons activated by menthol and/or cold. Accordingly, the invention, in some embodiments thereof, as described herein provides methods of treating, preventing or halting progression cerebral/ocular stroke in a subject comprising administering to the nasal mucosa of the vestibule of the subject a composition comprising a pharmaceutically acceptable carrier and/or a pharmaceutically effective amount of a TRPM8 agonist such as of menthol, icilin, camphor.

FIG. 11 illustrates a Ch-ONSor 1100 according to one implementation of the invention. The Ch-ONSor 1100 can be used to provide chemical stimulation to the nasal septal mucosa of the vestibule (AEN) in a pulsatile controlled fashion.

The Ch-ONSor 1100 may comprise a stimulator body 1102 and/or a stimulator probe 1104, where the stimulator probe ended with intranasal application head 1106. Generally, the chemical stimulator is configured to generate a chemical stimulus that may be delivered to the subject. The chemical stimulator probe designed to accommodate a micro pump 1112 for injection of chemical agent to septal mucosa of nose of a subject.

FIG. 12A-B illustrates stimulator probe 1200 of Ch ONSor 1100. The stimulator probe 1200 comprised detachable, disposable application head 1202, a stainless-steel syringe 1204 with spring like plunger, and/or the shaft of vibrating system 1206. The application head 1202 is cylindrical in shape and/or made of rigid plastic material. It contains a compressible elastic reservoir 1208 with irrigation holes 1210 for releasing its content during the activation of the system. The stainless-steel syringe 1204 is composed of a barrel 1212, which contains spring like plunger 1214 and/or pressure transmitting elastic bag 1216. The plunger and/or pressure transmitting elastic bag are maintained in place by an annular diaphragm 1218, through which the vibrating head 1222 moves up and/or down pushing the spring like plunger forward.

The pressure transmitting bag 1216 is separated from the reservoir by a thin elastic membrane 1220. As this elastic membrane is located between the reservoir 1208 and/or the pressure transmitting bag 1216, its function is to transmit the pressure pulsation from the vibrating head 1222 to the reservoir 1208 in order to release fluids from the irrigation holes 1210 in a pulsatile controlled fashion. Whenever the pressure inside the reservoir is decreased, the elastic membrane 1220 moves toward and/or bulge into the reservoir 1208 to compensate for decreased pressure induced by release of fluid from the reservoir 1208 through the irrigation holes 1210. In this embodiment, the function of the syringe with spring like plunger is to maintain optimal pressure inside the pressure transmitting bag as well as the reservoir after each pulsation.

FIG. 12B illustrates the features of the application head. It is composed of a plastic cylinder 1250 that can be connected to the stimulator probe by means of screw like mechanism 1258 or any other suitable mechanism. It contains a reservoir 1252 filled with chemical stimulant (TRPM 8 agonist) like menthol. On its external face, the application head has a number of irrigation holes 1254, through which reservoir 1252 content is released by pulsatile pressure of the vibrating system.

The stimulator body 1102 may comprise a housing 1122 and/or a defined a body cavity 1124, and/or base 1126. The body cavity 1124 may contain a control subsystem 1136 and/or a vibration power source 1134, and/or the user interface 1132 which together may generate and/or mechanically control the chemical stimulus. The power source may be any suitable power supply capable of powering one or more functions of the stimulator, such as one or more batteries, capacitors, or the like.

The stimulus may be delivered to a subject via the head 1202 of the stimulator probe 1200 which may be configured to be easily inserted into the nasal cavity and/or come in contact with the mucus membrane of nasal septum of a subject, FIGS. 2A and/or B. Stimulator probes are optionally detachable, sterile and/or disposable. The stimulator body 1102 and/or stimulator probe 1104 may be reversibly attachable.

The reservoir 1208 of the micro pump is located in the application head of stimulating probe. The reservoir is filled through an injection port 1256 at the superior end of the head, and/or its contents are released under pulsatile pressure through one or more irrigation holes 1254. In some embodiment, the reservoir 1252 is preloaded with chemical stimulant (TRPM 8 agonist) in the form of soft jell or thick fluid containing TRPM8 agonist such as menthol. A filling kit composed of a syringe preloaded with enough amount of sterile chemical stimulant is used to fill the reservoir of the micro pump through a specially designed cannula. It is appreciated that during filling of reservoir with stimulant solution, the irrigation holes 1254 are facing upward while the syringe is inserted into the injection port via a special cannula at a horizontal plan. Whenever the reservoir is fully filled, and/or the pressure reaches an appropriate level, the fluid will start to leave the reservoir through the irrigation holes. The irrigation holes 1254 are provided with one-way micro valve that let fluid out under pressure but prevented air to come into the reservoir. A similar one-way micro valve is present in the injection port 1256 to prevent outside leak of reservoir content.

On activating the Ch-ONSor 1100, the vertical movement 1150 produced by the head 1110 of vibration producing system will be coupled to the spring like plunger 1116 to transmit this pulsation through the pressure transmitting bag 1118 and/or finally to the reservoir 1112 of micro pump in order to release micro droplets of chemical stimulant from irrigation holes 1114 in a pulsatile way. The released contents will be in the form of very small droplets chemical stimulant for activation of the septal branch of AEN.

The stimulator body 1102 may comprise a user interface 1132 comprising one or more operating mechanisms to adjust one or more parameters of the chemical stimulus. The on/off switch can be connected to an internal controller 1136 located within the handle. The internal controller 1136 can be electrically coupled to the vibrating system 1134 to actuate the release of chemical stimulant by a mechanical movement of the head of vibrating system 1110.

Vibro-chemical stimulator (V-Ch-ONSor 1300): V-Ch ONSor 1300 is bi-modular device in which vibrotactile stimulation, and/or chemical stimulation can be provided through the same stimulator probe 1300 using a common user interface in a hand-held device. Providing two actions on a single system makes it easier for an operator for delivering specific dose of chemical stimulation and/or vibrotactile stimulation simultaneously or in a succession.
Vibrochemical Ophthalmic Nerve Stimulator 1300 (V-Ch ONS 1300)

FIG. 13A-B demonstrated the basic structure of V-Ch ONSor probe 1300. The micro pump is basically and/or functionally is the same as that had been described previously in a single mode Ch-ONSor 1100. However, some modifications have been made to allocate the chemical pump and/or the vibrotactile probe in the same stimulating head.

In this embodiment, the V-Ch ONSor 1300 is configured to generate vibrotactile stimulation and/or to accommodate a micro pump for pulsatile injection of chemical agent to stimulate septal mucosa of nose of a subject. As shown in FIG. 13A, 13B, The V-Ch ONSor 1300 probe is basically composed of a modified micro pump traversed at its center by a vibrating shaft 1322. The micro pump comprised an annular reservoir 1308, a pressure transmitting elastic bag of an inverted L shaped annular cylinder 1316, and/or an annular spring like plunger adapting at its center the shaft 1322 of the vibrating probe. The reservoir 1308 and/or pressure transmitting bag 1316 toke an annular shape or the shape of a hollow cylinder surrounding a centrally located vibrating shaft 1322. The irrigation holes 1310 located at the periphery of the application head. The pressure transmitting bag 1316 is separated from the reservoir 1308 by a thin annular shaped elastic membrane 1320. As this elastic membrane is located between the reservoir 1308 and/or the pressure transmitting bag 1316, its function is to transmit the pressure pulsation from the vibrating head 1324 to the reservoir 1308 in order to release fluids containing chemical stimulant through the irrigation holes 1310 in a pulsatile controlled fashion. Whenever the pressure inside the reservoir 1308 is decreased, the annular elastic membrane 1320 moves toward and/or bulge into the reservoir 1308 to compensate for decreased pressure induced by released fluid through the irrigation holes 1310. In this embodiment, the function of the spring like plunger 1314 is to maintain the optimal pressure inside the reservoir 1308 and/or to compensate for pressure loss caused by release of fluid through irrigation holes 1310 after each pulsation.

The stimulator body may comprise a housing and/or a defined a body cavity, and/or base. The body cavity may contain a control subsystem, the user interface and/or two vibration power sources, one for production of vibrotactile stimulation through the shaft 1322, and/or the other 1324 for mechanical pulsatile injection of chemical stimulant. The generated vibrotactile stimulation oscillates along the axis 1326 in order to produce mechanical stimulation of the AEN supplying the nasal septal mucosa of the vestibule. The power source may be any suitable power supply capable of powering one or more functions of the stimulator, such as one or more batteries, capacitors, or the like.

On activating the chemical module of V-Ch-ONSor the spring like plunger is pushed forward by a cylindrical vibrating shaft 1324 produced by the second vibration producing system. The vibration is transmitted via the pressure transmitting bag 1316, pressurizing the reservoir 1308 to release its content through the irrigation holes 1310 in a pulsating way. The released contents will be in the form of very small droplets of chemical stimulant for activation of the septal branch of AEN.

In instances where the stimulators described here are bi-modular such as vibro-chemical ONSor 1300, the user interface may comprise one or more operating mechanisms, which may allow the user to control the function of both stimulators such as the sequence of stimulation (simultaneous or sequential). For example, the micro pump is delivering the chemical agent in a pulsatile way with a frequency ranging from 0.5 Hz to 2 Hz, and/or 2 second on/13 second off. Programming of vibrotactile and/or chemical stimulation might be in the form of initial 2 second of chemical stimulation followed by 11 second of vibrotactile stimulation, followed by 2 second off for both chemical stimulation and/or vibrotactile stimulation. This pattern can be repeated over the session of treatment.
Ultrasonic Ophthalmic Nerve Stimulator 1400 (US-ONSor 1400)

US-ONSor 1400 is a h and held Ultrasonic Ophthalmic Nerve Stimulator. In some embodiments, US-ONSor 1400 relates to pulsed Low Intensity Low Frequency Ultrasound (LILFU) Nerve Stimulation systems for treating brain and ocular strokes, for example those caused by dysregulated reduced CBF/OBF by up regulation of TVS and/or TABRs through stimulation to V1 intranasally or at extra-nasal sites. The subject's TVS, ANS, and/or SG are modulated in a manner that is effective to treat the subject for the acute brain and ocular ischemic disorders. Generally, the systems are hand held devices with intranasal application head. The invention, in some embodiments thereof, relates to a method for increasing CBF/OBF to the brain retina and/or choroid and/or optic nerve in subject's dysregulated and/or reduced CBF/OBF. The invention, in some embodiments thereof, relates to the method for improving delivery of oxygen, glucose, anticoagulants, antioxidants, humoral mediators, growth factors and/or pharmacological agents to the targeted tissues of the brain, retina, and/or optic nerve.

LILFU stimulates peripheral neurons by two mechanisms. The first is thermal; where pulsed ultrasound enhances neural activity by increasing temperature of targeted nerve fibers up to 42 degrees C. for short time periods. In the second mechanism the stimulation is mechanical. LILFU stimulates neuronal activity at least partially by triggering voltage-gated Na transients and/or voltage-dependent $Ca^{2+}$ transients, which resulted in the generation of action potentials of the targeted neuron. Additionally, the LILFU-induced changes in neuronal activity were sufficient to trigger synaptic vesicle exocytosis and/or synaptic transmission at central synapses thereby driving network activity.

Pulsed LILFU has also been shown to stimulate the production of bFGF, TGF-β, BMP-7, VEGF, and/or IGF-1. Certainly bFGF, TGF-β, BMP-7, VEGF, and/or IGF-1 have differential yet significant effects on the nervous system by affecting processes involved in synaptic transmission, neuronal growth/survival, cell fate specification, tissue patterning, axon guidance in the nervous system, and/or angiogenesis in the brain. Moreover, VEGF, TGF-β, and/or bFGF are neuroprotective against hypoxic-ischemic injury and/or neurodegeneration. These observations prompt the intriguing question of whether it is possible for US to trigger these pathways in the brain, retina and/or or the production and/or secretion of growth factors such as brain-derived neurotrophic factor, neurotrophin-3, or nerve growth factor.

LILFU is typically in the range of 0.3 MHz to 0.8 MHz or above. A rate of 300 Hz (or lower) causes inhibition (down-regulation). A rate in the range of 500 Hz to 5 MHz causes excitation (up-regulation). Power is generally applied at a level less than 60 mW/cm$^2$. US pulses may be monophasic or biphasic, the choice made based on the specific patient and/or condition. The US transducer is pulsed, typically tone burst durations of (but not limited to) 25 to 500 μsec.

Turning now to the embodiments of the invention; US-ONSor system 1400 in the preferred configuration is shown in FIG. 14. A US-ONSor 1400 comprises of a body of the stimulator 1402, a neck 1404, and/or a head portion 1406 constructed of a rigid plastic material such as Acrylonitrile Butadiene Styrene (ABS). In some variations, the US stimulator probe 1400 may comprise one application head, which is small rounded that enable the user to introduce it easily in the nasal vestibule.

Housing: US-ONSor 1400 may have any suitable shape, such as cylindrical or tetragonal with blunted edges. In some variations, it may be desirable for the stimulator body 1402 to be shaped such that it can be easily gripped by a user, with a base connected to charging unit such that it can be placed upright on it as shown in FIG. 14.A. The stimulator body 1402 may have a flat base proximal end 1412 with a circular small tunnel 1414 for energy connection and/or a tapered proximal end that gives attachment to the shaft 1404 of the stimulator.

As mentioned above, the stimulator tetragonal body may comprise a housing 1408 formed by a front housing, a back housing, side housings, and/or a proximal housing for the base 1412 with tunnel for electric charging 1414 and/or distal end for attachment of the shaft (the neck) of the stimulator. The front housing, back housing, and/or side housing might constitute a continuous shell of a tetragonal cylinder, with one rectangular opening at front housing where the user interface 1410 can be adapted. The back housing may comprise an opening configured to receive a number of small lights 1416 (4 lights) that give an indication of status of battery. In some instances, it may be desirable for the stimulator body to be sealed, such that it may be waterproof or the like. In variations in which the housing comprises openings for other elements of the stimulator body (user interface, electrical connection at the base of the body, or the like), the interface between those elements and/or the stimulator housing may be watertight, and/or may comprise seals.

The selection of the ABS material for the US-ONSor 1400 body 1402, shaft 1404 and/or application head portion 1406 is made due to the excellent acoustic characteristic of ABS, and/or its ability to encapsulate the ultrasound transducer 1418. To increase the efficiency of the ultrasound transducer 1418, closed cell foam filler might be utilized at the back surface of the ultrasound transducer 1418 to redirect the radiation of ultrasonic pressure waves 1420 from the back surface of the ultrasound transducer 1418 toward the application head 1406 surface, thereby significantly increasing the output of the ultrasound transducer 1418 toward the targeted nerve to be stimulated. In some variations, housings 1408 may comprise other types of thermoplastic such as polycarbonate, polyetherimide. However, the housing may comprise any suitable material and/or materials.

User Interface: The stimulator body 1408 may comprise a user interface 1410 comprising one or more operating mechanisms to adjust one or more parameters of the US stimulus. For example, the operating mechanisms may allow the user to power the device on or off, start or stop the stimulus, change the US power or frequency of the stimulus, change the duty cycle, change the duration of the stimulus, change the stimulus pattern, or the like.

In some variations, the user interface 1410 may comprise one or more operating mechanisms, which may allow the user to use a predetermined protocol. In instances where the user interface may also comprise one or more ways of alarming signal to indicate the end of session such as an alarming sound. The number and/or locations of illuminated status indicators 1416 may indicate the charging status of any rechargeable battery Control Subsystem: Generally, the control subsystem 1424 may be configured to control a stimulus to be delivered to a subject via the stimulator probe 1404. The control subsystem 1424 may be contained within the housing of the stimulator. The control subsystem may be connected to the operating mechanisms of the stimulator which may allow the control subsystem to receive input from a user. The communication subsystem may be configured to facilitate communication of data and/or energy between the stimulator and/or an external source. Additionally or alternatively, some or all of the safety mechanisms of the control subsystem 1424 may be part of the processor. For example, the processor may comprise software that limits the frequency within an allowed range. In some variations, the frequency may be limited to about 500 Hz and/or about 800 Hz, between about 500 Hz and/or about 5 MHz, between about 500 Hz and/or about 1 MHZ, The stimulator body houses battery pack 1422, an electronic control module 1424, an electronic frequency generator module 1426, connecting wiring 1428, and/or a driving motor 1430. The electric motor generates sonic frequency of physical vibration of the head portion through a motion transducer, and/or an electronic system to provide operational control of the US-ONSor. The electronic system typically has an on-off switch, battery charge control, speed control for the motor and/or generates the ultrasonic frequency electrical current to power the ultrasonic transducer.

The US-ONSor device 1400 accommodates an ultrasonic transducer 1418, which protrudes from the application head of the device.

The US-ONSor 1400 stimulator body 1402 also contains a drive motor 1430 and/or an electronic control module 1424. The output shaft of the drive motor 1430 typically carries an off-center weight 1432. The shaft of the drive motor 1430 and/or the off-center weight 1432 attached to it rotate at least at approximately 30,000 rpm, creating a 500 Hertz ultrasonic frequency vibration in the application head 1406. In some variations, the stimulator probe may comprise one intranasal head 1406, which may be configured to be easily inserted into the nasal cavity and/or come in touch with the nasal septum of the nasal vestibule of a subject or patient. The application head 1406 is designed with a weight distribution plan wherein the head portion 1406 is significantly lighter weight than the loaded weight of the stimulator body 1402. The neck portion 1404 is designed to be lightweight and/or flexible, to act as a motion transducer. The weight of the stimulator body 1402 and/or the user's hand dampens the vibration amplitude of the stimulator body 1402, while the flexing neck portion 1404 causes the head portion 1406 to vibrate.

Ultrasonic Transducer: The best currently available material selection for the ultrasound transducer 1418 is typically a PZT-8 piezoelectric ceramic or similar material. In some embodiments, ultrasonic pressure waves may be produced by piezoelectric means and/or other methods known to the people experienced in the ultrasound generating art. The construction of the ultrasound transducer 1418 is not limited to piezoelectric ceramics, and/or not limited to a single element. The invention, in some embodiments thereof, eliminates the attenuation of the ultrasound energy emitted by the piezoelectric transducer by eliminating surface interfaces.

FIG. 14.B illustrates a side view of US transducer 1418, US-conduction-medium insert 1446 with US field focused on the target nerve bundle 1444. Depending on the focal length of the US field, the length of the US transducer assembly can be increased with a corresponding increase in the length of ultrasound-conduction-medium insert 1446. The focus of US transducer 1418 can be purely through the physical configuration of its transducer array 1440 (e.g., the radius of the array) or by focus or change of focus by control of phase and/or intensity relationships among the array elements. In an alternative embodiment, the US array is flat or other fixed but not focusable form and/or the focus is provided by a lens that is bonded to or not-permanently affixed to the transducer. In a further alternative embodiment, a flat US transducer is used and/or the focus is supplied by control of phase and/or intensity relationships among the transducer array elements.

Even though the target is relatively superficial; the transducer can be moved back in the holder to allow a longer focal length. Other embodiments are applicable as well, including different transducer diameters, different frequencies, and/or different focal lengths. In an alternative embodiment, focus can be deemphasized or eliminated with a smaller US transducer diameter with a shorter longitudinal dimension, if desired, as well. Ultrasound conduction medium will be required to fill the space. Examples of sound-conduction media are Dermasol from California Medical Innovations or silicone oil in a containment pouch.

Upon activating the hand held US-ONSor 1400 by the control switch 1442, the low voltage DC energy supplied by the battery pack 1422 is converted into an ultrasonic frequency DC current by the electronic frequency generator module 1426, which is connected to the ultrasound transducer 1418 by the connecting wiring 1428. Under the influence of the ultrasonic frequency DC current the ultrasound transducer 1418 resonates, expands and/or contracts volumetrically, in tune with the frequency supplied by the electronic frequency generator module 1426 and/or thereby converts the electronic energy into ultrasonic pressure waves 1420. These non-attenuated ultrasonic pressure waves 1420 are impacting nasal septal mucosa and/or stimulate septal branch of AEN.

The time averaged intensity of the ultrasonic pressure waves 1420 is ideally limited to approximately 30 mW/cm$^2$, which is effective for the purpose of nerve stimulation and/or at the same time it is below the tissue heating range. However, higher intensities can be applied with the appropriate safeguards against tissue heating or damage. The ultrasonic pressure waves 1420 could be applied in a pulsed burse mode modality such as 200-microsecond burse width repeated at 1 kilohertz repetition rate to further limit tissue heating. Depending on the final acoustic energy output of the ultrasound transducer, various burse widths and/or repetition rates are possible to assure that no tissue damage occurring. The ideal frequency of the ultrasonic pressure waves 1420 is between 0.44 MHz and/or 0.67 MHz.

The illustrated section of the neck portion 1404 is shown in FIGS. 14A and/or 14.B explains the motion transducer function of the neck portion 1404. The vibration created by the off-center weight 1432 and/or the motor 1430 in the stimulator body 1402 is a circular vibration. A motion transducer by definition converts one form of vibration into another form of vibration. To transform the circular vibration of the handle portion 1402 into a lateral vibration of the head portion 1406, the dimension Y of the neck portion 1404 is selected to be significantly larger than dimension X. Depending on the selection of the ratio between the X and/or Y the vertical vibration can be practically eliminated while maximizing the lateral vibration.

The electronic control module 1424 controls the rotation speed of the drive motor 1430. The control switch is a part of user interface 1410 provides on-off signals to the control module 1424 to start the sonic frequency motion of the head portion and/or the application head 1406. The user interface 1410 is also used to send programming impulses to the control module 1424 to create higher or lower ultrasonic frequency vibrations of the head portion 1406 by changing the rotational speeds of the drive motor 1430. Lower frequency vibration of the head portion 1406 will have smaller vibration amplitude and/or cause a gentler feedback to the user. Conversely, a higher frequency vibration will have higher vibration amplitude and/or provide a more powerful feedback to the user. A typical design will provide the user with multiple selectable speed options.

Power Source: The stimulator may comprise a power source. The power source may be any suitable power supply capable of powering one or more functions of the stimulator, such as one or more batteries, capacitors, or the like. As shown in FIG. 14.A, in some variations the power source may comprise a lithium coil cell battery 1434. The battery 1434 may be secured in place via any suitable method. In some variations, the power source may be rechargeable, as described in more detail below.

While the stimulator body 1402 comprises a power source 1422, in other variations the stimulator body need not comprise a power source. In some variations, the stimulator body may comprise a port, cord, or other mechanism for connecting the stimulator to an external power source (such as a wall outlet or separate battery pack), which in turn may be used to power one or more portions of the stimulator. In some other variations, such a port, cord, or other mechanism may be used to recharge a rechargeable power source. The stimulator body 102 may comprise such a port (e.g., a USB port) at any suitable location in the housing.

External Device Connection: In some variations the stimulators described here may be configured to connect to an external device, such as a mobile phone or a computer, or the like. In some variations, the stimulators may use a wireless or wired connection to connect to the internet, via which they may be connected to an external device.

The secondary inductive coil 1434 located in the stimulator body 1402 typically charges the rechargeable battery 1422 through the electronic control module 1424, which controls the voltage and/or current to properly charge the battery. The matching primary inductive coil is typically located in a separate charger assembly connected to household current.

Features of the waveform: The US vibration stimulation waveforms delivered by the stimulators described herein may be having different features and/or specifications. These include the shape, frequency, and/or US power, pulse width, with fixed or variable features.

Modulation of Parameters of waveform: As is described in more detail herein, the employed stimulation waveforms parameters might be fixed or modulated. The frequency, US power, and/or the pulse width may be modulated over time. The waveform may be modulated linearly, exponentially at random or regular basis. It should be understood that modulation of stimulus parameters is aimed to improve the efficacy of the stimulation, improve the clinical outcome of ONS and/or to prevent patient habituation to the applied stimulation (i.e., may help to prevent mechanoreceptor adaptation to vibration stimulation)

Ramping up and/or ramping down: In some instances, the waveforms described herein may be delivered during the whole session of stimulation without any change in its features. In some variations, stimulation bursts may be delivered periodically at regular or irregular intervals. The US stimulation power, pulse width, or frequency may be modified during the course of stimulation. For example, the US stimulation power may be ramped from low power to higher power over a period of time. In other variations, the US stimulation power may be ramped from high power to lower power over a period of time. The stimulation pulse width may also be ramped from a low pulse width to a higher pulse width over a period of time. The stimulation pulse width may be ramped from a high pulse width to a lower pulse width over a period of time.

Frequency: In order to treat brain and/or eye strokes or otherwise produce an increase in CBF/OBF by administration of US ONS, the stimulators described herein may be configured to generate one or more waveforms at frequencies suitable for US stimulating V1 for specific purpose. Generally, the frequency is preferably between about 500 Hz and/or about 8 MHz. In some of these variations, the frequency is preferably between about 500 Hz and/or about 1 MHz In others of these variations, the frequency is preferably between about 500 Hz and/or about 2 MHz. In some variations, the frequency may be about 500 Hz, about 600 Hz, about 700 Hz, about 800 Hz, about 900 Hz, about 1 MHz about 1.2 MHz, about 1.4 MHz about 1.6M. The frequencies described herein may be suitable for stimulating the targeted tissue to initiate a reflex circuit that activates TVS and TABRs thereby increasing the CBF/OBF and/or suitable for directly driving efferent fibers innervating the cerebral arteries, leptomeningeal collateral arteries, ophthalmic artery, ciliary and/or choroidal arteries.

US power: US power is generally applied at a level less than 60 $mW/cm^2$. In order to treat acute brain or ocular ischemic disorders or otherwise produce an increase of CBF/OBF by stimulating V1, the stimulators described herein may be configured to deliver US stimulus with suitable power. In some variations the US power may be between about 30 $mW/cm^2$ and/or about 60 $mW/cm^2$. In other variations, the power of US power may be variable. For example, the power may vary between about 30 $mW/cm^2$ and/or about 40 $mW/cm^2$ and/or about 40 $mW/cm^2$ and/or about 50 $mW/cm^2$, about 50 $mW/cm^2$ and/or about 60 $mW/cm^2$. For example, the US stimulation power may be ramped from low power to higher power over a period of time.

On/Off Periods: On-time and/or off-time parameters may be used to define an intermittent pattern in which a repeating series of signals is generated for stimulating the V1 during the on-time (such a sequence may be referred to as a "pulse burst"), followed by a period in which no signals are generated and/or the nerve is allowed to recover from the stimulation during the pulse burst. A 50% duty cycle is used. The on/off duty cycle of these alternating periods of stimulation and/or no stimulation may have a ratio in which the off-time may be set to zero, providing continuous stimulation. Typically, however, the ratio off-time/on-time may range from about 0.5 to about 10. Exemplary on/off durations include without limitation, 4 second on/1 second off, 5 seconds on/1 second off, 6 seconds on/1 seconds off, 7 seconds on/1 seconds off.

Exemplary Waveforms: It should be appreciated that any of the above waveform parameters and/or variations in parameters may be combined to generate a temporally patterned waveform as described herein, and/or these waveforms may be delivered by the stimulator described herein. For example, the waveform comprises pulse which may have any suitable frequencies, pulse widths, and/or US power. The US stimulation power, pulse width, and/or frequency may be the same from pulse to pulse, or may vary over time. In some variations, the power of US pulses may increase (linearly, exponentially, etc.) from a minimum value to a maximum value, drop to the minimum value, and/or repeat as necessary. In some variations, the power of the pulses may vary according to a sinusoidal profile. Combinations of these parameters may increase the efficacy and/or comfort of stimulation.

Programming of the device: Certain parameters of the US stimuli generated by the US-ONSor 1400 are programmable. Programming the neurostimulator may be performed in a variety of manners, including those known to persons skilled in the art having benefit of the present disclosure.

Programming for safety: There are a number of safety measures that should be taken into consideration before releasing the device for physician use. One example is the frequency of waveform. The frequency is limited between 500 Hz to 8 MHz. Lower frequencies might have inhibitory effects on ophthalmic nerve Saved Waveform Settings: Some variations of the stimulators described herein may be configured with a number of stimulation waveforms. In some variations, a preferred set of waveforms is selected according to the age of patient, staging of the disease, and/or the history of nasal trauma or surgery. In some variations, random selection of a different waveform each time is employed to decrease the risk of patient's adaptation to any of waveform of particular stimulation pattern.

Optical Nerve Stimulation

This invention, in some embodiments thereof, relates to pulsed optical nerve stimulation systems for treating brain and ocular strokes for example, those caused by dysregulated reduced CBF and/or OBF by up regulation of TVS and/or TABRs through stimulation to V1. The site of stimulation may include; nasal cavity mucosa, skin of the face supplied by V1. The subject's TVS, ANS, pancreatic TVR and/or SG are modulated in a manner that is effective to treat the subject for different acute brain, retinal, and optic nerve ischemic disorders. Generally, the systems are portable devices and/or may have portable case, and/or intranasal heads, face mask. The invention, in some embodiments thereof, relates to a method for increasing CBF/OBF to the brain, retina and/or optic nerve head in subject's dysregulated and/or reduced CBF/OBF. The invention, in some embodiments thereof, is also related to the method for improving delivery of oxygen, glucose, anticoagulants, humoral mediators, growth factors and/or pharmacological agents to the targeted tissues of the brain, retina, and optic nerve.

Optical neural stimulation is emerging as an exciting and/or more advantageous alternative to traditional electrical stimulation. The method relies on direct but transient (non-contact, pulsed) irradiation of the nerve surface by using a light source such as lead or laser. The response to optic stimulation is spatially precise, permitting selective targeting of individual nerve fascicles with no observed tissue damage. Genetic modification of neurons to express opsins, i.e. light-sensitive proteins on neuronal membranes, renders neurons sensitive to light of a specific wavelength with millisecond precision.

Transdermal melanopsin-mediated optical stimulation of V1

Transdermal melanopsin-mediated optical stimulation of V1 is a non-invasive alternative approach of optical stimulation of peripheral sensory neurons. It relies on stimulation of subset of neurons of V1 naturally expressing melanopsin and the use of blue light as a source for stimulating these neurons. This technique depends on the concentration of melanopsin in the targeted tissue and/or the optical properties of the intermediate tissues e.g. skin and/or subcutaneous tissue. Melanopsin is a type of photopigment belonging to a larger family of light-sensitive retinal proteins called opsins and/or encoded by the gene Opn4. Melanopsin photoreceptors are sensitive to a range of wavelengths and/or reach peak light absorption at blue light wavelengths around 480 nanometers. In human, TG neurons expressing melanopsin range from 14 to 46 μm, classifying them as C fiber or Aδ fiber neurons. The said melanopsin-expressing neurons also likely express receptors for other sensory stimuli, for example, TRPM8 for temperature and/or evaporation in small (10-30 μm) C fibers or piezo2 for pressure in medium-sized (30-50 μm) Aδ fibers have demonstrated a decrease in corneal mechanical sensitivity in OPN4$^{dta/dta}$ mice, consistent with ablation of melanopsin-expressing mechanoreceptive Aδ fibers. Coincident blue light stimulation of melanopsin-expressing neurons that express also TRPM8 may lead to enhanced SP and CGRP expression and activation of TVS and/or TABRs and/or may decrease the threshold of stimuli for either light, cold stimuli and mechanical stimuli.

Intranasal cavity is a self-contained cavity and/or was chosen for optical stimulation for a number of reasons, these include; the near location of branches of V1 to the surface of nasal mucosa, the relatively thin keratin layer. Additionally, nasal vestibule is richly supplied with unmyelinated C fiber or Aδ fiber neurons of V1 that express melanopsin.

Optical Ophthalmic Nerve Stimulation

This invention, in some embodiments thereof, relates to pulsed optical nerve stimulation systems to V1. The site of stimulation may include; nasal cavity mucosa supplied by AEN. Generally, the systems are portable devices and/or may have portable case, and intranasal stimulating heads. The invention, in some embodiments thereof, relates to a method for increasing OBF to the retina and/or choroid and optic nerve head in subject's dysregulated and/or reduced OBF.

Optical neural stimulation is emerging as an exciting and/or more advantageous alternative to traditional electrical stimulation. The method relies on direct but transient (non-contact, pulsed) irradiation of the nerve surface by using a light source such as lead or laser. The response to optic stimulation is spatially precise, permitting selective targeting of individual nerve fascicles with no observed tissue damage. Genetic modification of neurons to express opsins, i.e. light-sensitive proteins on neuronal membranes, renders neurons sensitive to light of a specific wavelength with millisecond precision.

Transdermal Melanopsin-Mediated Optical Stimulation of V1

Transdermal melanopsin-mediated optical stimulation of V1 is a non-invasive alternative approach of optical stimulation of peripheral sensory neurons. It relies on stimulation of subset of neurons of V1 naturally expressing melanopsin and the use of blue light as a source for stimulating these neurons. This technique depends on the concentration of melanopsin in the targeted tissue and/or the optical properties of the intermediate tissues e.g. skin and/or subcutaneous tissue. Melanopsin is a type of photopigment belonging to a larger family of light-sensitive retinal proteins called opsins and/or encoded by the gene Opn4. Melanopsin photoreceptors are sensitive to a range of wavelengths and/or reach peak light absorption at blue light wavelengths around 480 nanometers. In human, TG neurons expressing melanopsin range from 14 to 46 μm, classifying them as C fiber or Aδ fiber neurons. The said melanopsin-expressing neurons also likely express receptors for other sensory stimuli, for example, TRPM8 for temperature and/or evaporation in small (10-30 μm) C fibers or piezo2 for pressure in medium-sized (30-50 μm) Aδ fibers have demonstrated a decrease in corneal mechanical sensitivity in OPN4$^{dta/dta}$ mice, consistent with ablation of melanopsin-expressing mechanoreceptive Aδ fibers. Coincident blue light stimulation of melanopsin-expressing neurons that express also TRPM8 may lead to enhanced SP and CGRP expression and activation of TVS and/or TABRs and/or may decrease the threshold of stimuli for either light, cold stimuli and mechanical stimuli.

Intranasal cavity is a self-contained cavity and/or was chosen for optical stimulation for a number of reasons, these include; the near location of branches of V1 to the surface of nasal mucosa, the relatively thin keratin layer. Additionally, nasal vestibule is richly supplied with unmyelinated C fiber or Aδ fiber neurons of V1 that express melanopsin.

Optical Ophthalmic Nerve Stimulation (Op ONSor 1500)

Portable optical ONSor system 1500: FIG. 15 illustrates one particularly preferred embodiment of the present invention wherein the Op-ONSor 1500 consists of a portable control unit 1500. In this particular embodiment the case or housing 1502 is equipped with a clip 1512 that allows the unit to be worn on the shirt pocket or belt or the like during use. The other side of the case relative to the belt clip is equipped with a display 1504 (user interface) which may be a touch screen that allows the user to adjust different parameters of the optical stimulus such as the frequency, energy, intensity, type of light emitted by the light source, irradiance (25-50 mW/mm$^2$), Pulse width (10 ms), shape of waveform and/or modulating these parameters or select preset features of the stimulus. In some variations the system 1500, delivers pulsed blue light. In other variation the system 1500 delivers pulsed NIR light. The Control unit 1500 of the system communicates with the light delivery device 1522, 1524 via power coupling 1518, 1520. In one embodiment, the stimulating tube is designed to have round shaped tip that can be inserted easily in the nasal cavity.

The top face of the case 1502 is further provided with an on/off switch 1510 and/or a two-power coupling 1518, 1520 connecting the light delivery device and/or the control unit by two power outlets 1414, 1516. During administration of optical ONS, typically stimulating tubes 1522, 1524 are inserted into both nasal vestibules and/or held in place via nasal clips.

As shown in FIG. 16, the light delivery device 1600 comprises a stimulating tube 1604 for providing optical stimulation to the nasal cavity in accordance with one embodiment of the present invention. The light delivery device 1600 in this embodiment generally includes a housing 1602 and/or a light source 1618 positioned in or near the housing. The distal end of the stimulating tube 1604 is configured to be inserted into the nasal cavity to stimulate V1 by administration of pulsed blue or NIR light to the nasal cavity. The frequency of pulsed blue or NIR light might be 10 Hz, 15 Hz, 20 Hz, 25 Hz, 30 Hz, 35 Hz, 40 Hz, 45 Hz, 50 Hz, 55 Hz, 60 Hz. or more.

In some embodiments, the housing of the light delivery device in combination with the light source 1618 are configured to be held in place by nasal clip 1606 for an extended period of time (therapeutic time) without undue effort or discomfort, due to the lightweight, portable design of the device.

In one embodiment, the stimulating tube 1604 comprised of proximal opaque part 1612 and/or distal transparent part 1614. As will be appreciated, optically transparent distal part 1614 comprised of components or materials that are transparent to blue light, (wavelengths between about 400 nm and/or about 500 nm) and/or NIRL (680-830 nm). In some cases, optically transparent part 1614 can refer to more narrow ranges of transparency. For example, optically transparent to blue light can refer to transparency in the range from about 455 nm to 505 nm; more specifically to 480 nm A sleeve 1608 may be provided to at least partially cover the stimulating tube 1604. In one embodiment, the sleeve 1608 is disposable and/or in another embodiment, the sleeve is not disposable. Non-disposable sleeve is sterilizable.

The stimulating tube 1604 is covered by a disposable or re-usable sleeve 1608. The sleeve is made of materials such as aluminum or a plastic coated with aluminum. In this embodiment, the inner material will transmit light with limited or not absorbing the light. These configurations generally allow optical energy, or light, generated by the light source 1618 to travel through the stimulating tube 1604 and/or exit both the tip 1614 of the tube 1614 and/or the tip of the sleeve 1616. At the distal end of the sleeve, there is a transparent window 1616 for the exit of light. The shape of the window defines the targeted area of the nasal cavity to be stimulated by blue light and/or NIR light. In some embodiment the window might be cylindrical in shape and/or include all the distal part of the sleeve. In another embodiment the window takes the shape of an incomplete cylinder with an opaque wall adjacent to the lateral wall of the vestibule. In another embodiment the window represented as a half of cylinder of transparent window facing the nasal septum. The covering sleeve can further control the illumination pattern by using different types of sleeves having different aperture sizes or pattern of the tip. In such embodiments, light energy is emitted from the stimulating tube 1604 to activate V1 within the nasal cavity of the patient.

The proximal end 1612 of the stimulating tube 1604 is coupled to the distal end of the housing 1602 by any of a variety of couplings such as a press-fit connection, a screw, or any other suitable coupling that ensure optimal mechanical, optical, and/or electrical couplings. In some variations, the stimulating tube 1604 may be permanently attached to the housing 1602.

In one embodiment, the housing 1602 of the body includes a light source 1618. Suitable lighting technologies, including, a bulb, an emitter, a light emitting diode (LED), a xenon lamp, a quartz halogen lamp, a standard halogen lamp. As will be appreciated by those skilled in the art, a variety of suitable lighting sources can be employed in the embodiments disclosed herein, without departing from the scope of the invention Light source: The Op-ONSor 1500 devices of the embodiments of the invention may include one or more light sources; such as light sources that is solid state or LEDs. Alternatively, the light sources may emit non-coherent light. In still other embodiments, the light sources may be blue light sources that emit non-coherent light in a range from 400 nm to 500 mm and in the range of 680-830 nm for NIR light. In other embodiments, the blue light source may be limited in wavelength to 460 nm to 500 nm. In still other embodiments, the light source may be adapted to emit substantially only blue light with a wave length 480 nm.

In still other embodiments, the light source may be adapted to emit substantially only NIR light with a wave length 820 nm. In some of the embodiments, the light source is located in the housing 1602. In other variation, light source resides outside the housing in the stimulating tube 1604, some of which may reside in the tip 1614 of the stimulating tube 1604. The light sources may each emit light at a different energy or optical power level, or at the same level. The light delivery device 1600 may be configured to provide light from three light sources, each having a different relative output energy, and/or relative energy density level (e.g., fluence) and different wavelengths.

The Op-ONSor devices of the embodiments of the invention can be adapted and/or configured such that the stimulating tube is further adapted to transfer heat proximally when the light source is at the distal end of the stimulating tube. In other embodiments, the stimulating tube can be adapted to focus light from the light source.

As will be appreciated by those skilled in the art, it may be desirable to control variables or control parameters associated with the output of the light delivery device 1600. Examples of such variables include power, timing, frequency, duty cycle, spectral output, and/or illumination pattern. In one embodiment, the control circuit 1626 controls the delivery of power from the power supply 1610 to the light source 1618 according to the activation or status of the controller 1626. For example, in one embodiment, the control circuit 1626 includes a relay, or a transistor, and/or the controller 1626 includes a button, or a switch. When the button or switch of the controller 1626 is pressed or activated, power from the power supply 1610 is able to flow through the control circuit 1576 and/or the light source 1618.

Intranasal transdermal optical stimulation of V1 for both nasal cavities may be simultaneous or alternating. In alternating mode of V1 stimulation, the optical stimulus activate one side for a time (3 seconds) while there is no stimulation of the other side during this period, followed by 3 second stimulation of the non stimulated side with no stimulation of the opposite side, and/or this cycle of alternating stimulation can be continued during the session of optical ONS.

Hybrid Electro-Optical Stimulation

In some embodiments, the present invention provides an apparatus and a method for optical, electrical or by hybrid electro-optical stimulation of neurons of V1 in the nasal cavity to obtain a physiological response in a subject (e.g., increased CBF/OBF) and to treat Cerebral or eye strokes.

In some embodiments, one or more electrodes are placed adjacent the AEN, a branch of V1 intranasally to provide a sensitizing stimulation signal that by itself, would not be sufficient to trigger a nerve action potential (NAP), but when combined with an optical stimulation signal applied in temporal proximity, enhances the probability of triggering a desired NAP along the V1

In some embodiments, simultaneous application of both an optical stimulation signal and an electrical stimulation signal provides more efficacious generation of NAP responses in the subject than either optical or electrical stimulation alone. In addition, the much higher precision possible when using optical stimulation permits many more channels of ophthalmic nerve pathway such as unmyelinated C nerve fibers and and/or Aδ fiber neurons to be individually and distinctly stimulated than is possible using electrical stimulation alone. In some embodiments, the application of an electrical field before or during the application of the optical stimulation pulse permits more reliable generation of NAP signals than is possible using the optical signal pulse alone, and permits reliable generation of NAP signals. In some embodiments, optical stimulation pulses are also provided at short repeated intervals (called "spikes) shortly after the threshold-level electrical stimulation signal, delivered to certain frequency-specific ophthalmic-nerve pathways in order to enhance the expression of SP and CGRP in neurovascular tissues of the brain, retina, and optic nerve.

As used herein, "light emitter' is the light-emitting end from which a light signal is delivered to assist in, or by itself cause, stimulation of a nerve action potential (NAP). In some embodiments, light emitter is the light-emitting end of an optical fiber or similar waveguide that couples light from a light source such as a laser, or light-emitting diode (LED) or the like, connected to an electrical controller to a location at a distance from the controller (i.e., the light is coupled from where it is generated in or near the controller to the nerve to be stimulated, which is at a distance from the controller), while in other embodiments, the light source is located proximate to the nerve to be stimulated, and is electrically coupled to the distal controller Hybrid Electro-Optical Ophthalmic Nerve Stimulator 1700 (HEOp-ONSor 1700)

FIG. 17 illustrates a diagram of a noninvasive system of HEOp-ONSor 1700 that uses both electrical stimulation and light stimulation of V1 to obtain ocular vascular response for a subject. In some embodiments, the device 1700 includes an optical portion and an electrical portion for the stimulation In one embodiment, the device comprised stimulating part 1702, housing 1704, and nasal clip 1706. In one embodiment, the optical portion of the device is represented by a stimulating tube 1710 comprised of proximal opaque part and/or distal transparent part. The proximal end of the stimulating tube 1710 is coupled to the distal end of the housing 1704 by any of a variety of couplings 1716. In one embodiment, the housing 1704 of the body includes a light source 1712.

In one embodiment, the electrical portion 1708 is represented by a sleeve covering the simulating tube wherein a plurality of electrodes is embedded in the wall sleeve 1718.

The stimulating sleeve 1708 may comprise a plurality of electrodes 1720, 1722 located on the wall 1718 of the stimulating sleeve 1708. Two or more electrodes may be spaced longitudinally along the length of the nasal aspect (in contact of the nasal septum) of the sleeve. The electrodes described herein may comprise any conductive materials, such as hydrogel or metals, conductive ceramics, or the like.

As shown in FIG. 17B the cut-sectional view of the stimulating sleeve 1708, of HEOp-ONSor 1700, the electrodes 1720 and/or 1722 may be connected to leads 1724 and/or 1726 located within stimulating sleeve 1708. The leads 1724 and 1726 may in turn be connected to connectors 1728 and/or 1730 respectively. Connectors 1728 and 1730 may extend through the proximal part of the housing 1704, and/or may connect directly or indirectly to the control subsystem (not shown) and/or power source 1734. In one variations of HEOp-ONSor 1700, may comprise a return contact 1732 located on the angle and/or inner surface of arm of the nasal clip 1706, and/or configured to be in contact with shin of nostril. As such, the electrical stimulus may travel from the control subsystem (not shown) through the connectors 1728 and 1730, through the leads 1724 and/or 1726, and/or through the electrodes 1720 and/or 1722 stimulating the nasal mucosa of the septum of the subject, activating TVS and/or TABRs for increasing the CBF/OBF in brain, eye stokes and acute dysregulated reduced CBF/OBF.

The proximal end of the stimulating sleeve 1708 is coupled to the distal end of the housing 1704 by any of a variety of couplings 1716 such as a press-fit connection, a screw, or any other suitable coupling that ensure optimal mechanical, optical, and/or electrical couplings. In some variations, the stimulating sleeve 1708 may be permanently attached to the housing 1704. In one embodiment, the sleeve 1708 is disposable and/or in another embodiment, the sleeve is not disposable. Non-disposable sleeve is sterilizable.

In some embodiments, the electro-optical application head of the present invention is used to stimulate selective melanopsin containing nerve fibers by using subthreshold stimulus of blue light energy (489 nm) to sensitize theses fibers combined with subthreshold electrical stimulus. Hybrid electro-optical stimulation of melanopsin containing nerve fibers is configured to produce nerve action potential in melanopsin containing nerve fibers of ophthalmic nerve, thereof, enhance expression of SP and CGRP in neurovascular tissues of the brain and the eye.

Hybrid Electro-Optical Ophthalmic Nerve Stimulator 1800 (HEOp-ONSor 1800)

FIG. 18A shows for illustrative purposes only show an example of HEOp-ONSor 1800 perspective longitudinal cut sectional view of one embodiment of the present invention. The said device uses both electrical stimulation and light stimulation of AEN to provide an effective method for increasing OBF in subjects with dysregulated blood flow ocular vascular response for patient. In some embodiments, the HEO-ONSor 1800 includes plurality of optical fibers for optical stimulation and a number of electrodes for electrical stimulation of V1.

As shown in FIG. 8A, device comprised of an application head 1802 which can be held in place by a nasal clip 1804 during the treatment session without undue effort. The optic fibers for example optic fiber 1806, 1808 are incorporated in the application head and run for variable lengths where it ends a light emitter 1810, 1810. In some embodiments, one or more of the light-delivery options is used in HEOp-ONSor 1810. In a first option, a waveguide 1806 ends in an angled facet 1810 and reflects or diffracts the light out in a radial or side 'side firing' direction 1810 of the waveguide 1806 as light/laser beam 1812 toward the nasal septum or lateral nasal wall. In a second option, a waveguide 1808 ends in an bullet like end facet 1810 that transmits the light out in an axial direction 1814 of the waveguide as laser beam 1818, Such that the length of the end of fiber 1808 is perpendicular or at some other steep angle to the nerve fibers of V1 to be stimulated at the nasal cavity. Proximate the proximal end of the housing, the preferred embodiment has a plurality of optic fibers gathered in a single port 1816 and connected to the light source by any connecting cable (not shown) via a suitable coupling 1820. In this way, the light signal having a specific wavelength is emitted through window 1850. 1852, 1854, 1856, 1858, and 1860 and focused on corresponding areas of the nasal septum or temporal wall of the nasal cavity, while axial emitter 1862 and 1864 deposits its light signal towards the mucosa of nasal cavity.

The intranasal application head 1802 of HEOp ONSor 1800 comprised also of a plurality of electrodes incorporated in the application head 1802 of the device. A plurality of electrodes for example 1816 and 1818 are present on either surface of the application. The inner surface of the nasal clip 1804 provides a place for return electrode 1820 that come in contact with skin of the lateral wall of the nose. During administration of electric ONS, typically electrodes for both sides of application head are held in contact with mucosal lining of the nasal septum and lateral wall of nasal cavity by the means of clipping 1804 method, while the return contact 1420 touching the skin of nostril.

FIG. 18B shows for illustrative purposes only shows an example of front view of one of the application surfaces of HEO-ONSor 1800 as an embodiment of the present invention. The application head 1802 surface 1850 comprised a plurality of optic fibers that end in a light side emitter arranged in horizontal rows of windows; 1852, 1854, 1856, 1858 that deliver pulsed blue and/or NIR light toward the nasal septum and lateral nasal wall, and axial emitters 1860 that dispose light stimulus toward the nasal cavity. In this way, the light signal having a specific wavelength is emitted through window in the horizontal rows 1852. 1854, 1856, 1856, and 1858, focused on corresponding areas of the nasal septum or temporal wall of the nasal cavity, while axial emitter 1860 deposits its light signal towards the mucosa of nasal cavity. A number of electrodes 1862, 1864, 1866, 1868 are distributed in a regular manner between the rows of widows for light emitters.

In some embodiments, the light signal used to stimulate a NAP 1 includes wavelengths in the range of 450-480 nm which responsible for activation/sensitization of melanopsin containing nerve fibers and in some particular embodiments wavelengths in the range of 630-820 nm where the red/NIR is suitable wavelength stimulation of unmyelinated nerve fibers at deeper levels. In some embodiment, all light signals having the same wavelength is emitted through all windows and focused on corresponding areas of excitable tissue of the AEN underneath the mucosa. In other embodiment the light emitters dispose subthreshold signal having a wave length of 480 nm and 840. The blue light signal is configured to stimulate the superficially located, electrically sensitized nerve fibers while the NIR light will stimulate nerve fibers at deeper levels preferably unmyelinated C fibers. In some embodiments, a plurality of electrical signals is also generated by sources 602 and electrically conducted (e.g., by conductors applied to the nasal mucosa near the site of optically stimulated tissues, and applied to pre-sensitize the excitable tissue 98 such that a lower-powered optical signal beam (e.g., 621) can be used to trigger a NAP. In some embodiments, the optical windows 622,625, and 628 include micro lenses between the gratings and the target tissue in collimated, diverging, or converging patterns. In some embodiments, the micro lenses direct light in circular path, or disperse light from 0 to 360 degrees in a radial pattern perpendicular to fiber with set area and divergence angle.

In some embodiments, electrical preconditioning/stimulation from the electrical-stimulation portion (through the electrical current sources of FIG. 1B) applies electrical current 116 to the nerve tissue to be stimulated using an electrode array (in some embodiments, the electrical signal is sub-threshold relative to triggering a NAP in the neuron (s), meaning that when applied by itself, it has a low probability of triggering a NAP), and a low-power, optical stimulus i.e., requiring little electrical current to initiate NAP) is selectively activated by electrical current from electrodes. The electro-optical probe selectively emits light from each of a plurality of light emitters in order that the optical energy combines with the electrical preconditioning to trigger NAPs with fine-grained and precise accuracy not available if using electrode stimulation alone, and with lower optical power than if using optical stimulation alone. The lower-power optical output provides at least some of the following advantages: it reduces the power needed from the battery, it reduces the amount of heat generated by the optical source, and it reduces the possibility of tissue damage from the optical signal. In some embodiments, the present invention is used in applications where there is a need for precise placement of an electrode, but with the requirement to stimulate a large number of nerves, either simultaneously or individually. A single-core optical element (e.g., a fiber with a single waveguide) allows for extremely precise stimulation but can lack the ability to supply and/or spread enough power to stimulate large areas of nerves. In some embodiments, the electrical portion of the probe lacks specificity (since even with a point source of electricity, the electrical signal will spread across electrically conductive tissue), but can provide sufficient power to stimulate large areas. In some embodiments, the electro-optical application head of the present invention is used in selective stimulation of unmyelinated C nerve fibers where locating the application head at nasal cavity wherein these targeted nerve fibers are pre conditioned by subthreshold electrical stimulation and selectively stimulated by deposition of subthreshold stimulus of blue light.

In some embodiments, the HEOp-ONSOR 1800 all of the light signals haves substantially the same wavelength, since each signal is carried by a separate waveguide from the sources to their respective ends where they emit the respective light beams, each directed at a different target of excitable tissue of AEN. In other embodiments the HEOp-ONSOR 1800 uses a plurality of sources (not shown) that each emit a different wavelength of light and that generate coordinated electrical stimulation signals to sensitize the excitable tissue of AEN. In some embodiments, the wavelength is matched to the desired penetration depth wherein a portion of the emitters distributed in the rows 1852,1854, 1856,1858 emit blue light (480 nm) to sensitize/activate superficially located melanopsin containing C unmyelinated nerve and to a lesser extent to sensitize and/activate melanopsin containing C unmyelinated nerve at deeper level. In other embodiments, other portion of emitters within said widows emit NIR light (630-820 nm) to further sensitize the deeply located melanopsin containing C unmyelinated nerve and to an extent make them selectively activated by sub-threshold electrical stimulus form adjacent electrodes of the application head In Some embodiments, the electro-optical application head housing heat sink is made of a heat-conducting biocompatible material that has a relatively large thermal mass that readily absorbs short heat spikes from the light emitters and then dissipates the heat over a longer period of time to the proximal aspect of the stimulator 1802. In some embodiments, the intranasal application head housing heatsink includes an inside layer (1830) of very-high thermal-conductivity material such as copper that readily absorbs short heat spikes from the pulsed signals, and an outer layer 1870 of thinner biocompatible material such as titanium, which has a lower thermal conductivity to dissipate the heat over a longer period of time in order to prevent thermal damage to nasal tissue.

Transdermal Electrical ONSor Devices

A Transdermal Electrical ONSor Devices relates to a transdermal electrical nerve stimulation (TENS) apparatus for treating brain and ocular strokes for example caused by acute dysregulated reduced CBF/OBF by up regulation of TVS and/or TABRs through stimulation to V1. The subject's TVS, ANS and/or SG of SNS are modulated in a manner that is effective to treat the subject for acute ischemic cerebral and ocular disorders. Generally, the devices are handheld or portable devices. The handheld devices may have a stimulator body and/or a stimulator probe having one or more intranasal application heads. The portable version of E-ONSor may have portable case, and/or intranasal heads, extra nasal application heads, upper lid and/or forehead adhesive electrodes.

Described here are methods for treating acute brain and ocular ischemic disorders by providing electrical stimulation to an anatomical structure located intranasally (mucosa of the nasal septum) or extra nasally over the nasal bridge and/or foreheads. Exemplary anatomical structures include different receptors and/or nerve fibers of V1. The electrical stimulation, when delivered to certain targets as described herein, is generally capable of initiating a reflex circuit that activates the TVS and/or TABRs to increase CBF/OBF, and/or enhance pancreas to increase its insulin secretion, controlling hyperglycemia, augmenting glycolysis and/or combat nerve cell starvation caused by acute ischemia. The reflex circuit may include stimulation of a nerve directly or a cutaneous sensory cell that in turn activates a nerve which then produces either direct sensory input to the blood vessels of the brain and the eye or indirectly via stimulating the brain stem centers. The electrical stimulation may additionally or alternatively be capable, when delivered to other certain targets as described herein, of directly driving efferent fibers innervating the cerebral and/or ocular circulation.

Portable Electric ONSor 1900

Turning now to the embodiments of the invention; the portable noninvasive transdermal electrical ONSor device. More specifically, the invention, in some embodiments thereof, relates to an E-TD-ONSor 1900 device that operates in the electrical current range of about 0.1 mA to 10 mA, preferably from 1-3.5 mA using a frequency ranged from 10-60 Hz. The device is configured to deliver a pulse-based electrical waveform, which might be biphasic, alternating monophasic, or monophasic or the like. In some embodiment the device has a portable case (housing) and/or different types of stimulating electrodes. The stimulation waveforms described herein may be delivered via one or more intranasal clipped application heads 1904, extra nasally clipped application heads 1950 to the nasal bridge (e.g., nose supported), and/or the foreheads (self supported adhesive electrodes).

FIG. 19A illustrates one particularly preferred embodiment of the present invention wherein the E-TD-ONSor 1900 consists of a portable housing 1902 with intranasal application head 1904. In this particular embodiment the case or housing 1902 is equipped with a clip 1918 that allows the unit to be worn on the belt or the like during use. The other side of the case 1902 relative to the clip 1918 is equipped with a user interface 1906 that allows the user to adjust different parameters of the electrical stimulus such as unilateral or bilateral stimulation, the frequency, amplitude, shape of waveform and/or etc., and/or modulating these parameters or select preset features of the stimulus.

The top face of the case 1902 is further provided with an on/off switch 1908 and/or a monitor light 1914. Also, there are two electrode connector terminals 1910 and/or 1912 provided on the top face of the case 1902. They are connected to electrodes incorporated in the intranasal application head 1904. The two inner surfaces of the distal end of the application accommodate electrodes 1920, 1922. One or more electrodes are present on the inner surface of the application head. The outer surface of the proximal end of the application head 1904 provides a place for return electrode 1924 that come in contact with the inner lateral wall of the vestibule. During administration of electric ONS, typically electrodes 1920, 1922 for both sides of nostril are held in contact with mucosal lining of the nasal septum by the means of clipping method, while the return contact 1924 touching the skin of nostril. Activation of right or left side via intranasal application head depend on the side of cerebral or ocular stroke.

Intranasal stimulation: In nose supported variations, intra nasal application head 1950 (FIG. 19B) with nasally supported clips and having two sets of electrodes 1952, 1954 may be used to stimulate one side of the nasal septum, while the return electrode 1960 is configured to touch the skin of exterior of the nose. The electrodes are connected by leads and/or wired to the body of the device 1900. This type of intranasal probe is used when unilateral ONS of the ipsilateral side of the stroke is required for the treatment of a subject to avoid intracerebral vascular steel phenomenon. The latter contain user interface 1906, controller, and/or feedback elements for various purposes. The user interface may comprise one or more operating mechanisms to adjust one or more parameters of the stimulus. Additionally or alternatively, the user interface may comprise one or more feedback elements.

When bilateral electrical ONS is required, Intranasal application head 1904 (FIG. 19A) with two sets of electrodes 1920, 1922 may be used to stimulate either side of the nasal septum of the nose, while the return electrode 1924 is configured to touch the skin of outlet of the nose. The electrodes are connected by leads and/or wired to the body of the device 1900. This type of intranasal probe is used when bilateral ONS is required as in case of stroke involving both sides of the brain.

Classically electrical stimulation of V1 is performed intranasally in one side whether the right or left side depending on the site of brain and or eye stroke. In certain conditions in which the stroke affects both sides of the brain, for example as a result of multiple emboli, electrical stimulation is delivered to both sides. Electrical stimulation of V1 in both sides of the nose may be simultaneous or alternating. In alternating mode of V1 stimulation the electrical current stimulates one side for a time (3 seconds) while there is no stimulation of the other side during this period, followed by 3 second stimulation of the non stimulated side with no stimulation of the opposite side, and/or this cycle of alternating stimulation can be continued during the session of electric ONS. Whenever simultaneous stimulation of V1 in both sides is considered, and/or the waveform comprises a biphasic pulse, it may be desirable to configure the biphasic pulse to be charge-balanced, so that the net charge delivered by the biphasic pulse is approximately zero. Each phase of biphasic pulse may be either voltage controlled or current controlled.

In this particular illustrated embodiment, a limited number of frequency settings are available to the user (typically 10 Hz, 20 Hz, 30 Hz or 40 Hz). As such this particular embodiment is easily operated by the physician. In a more complex embodiment, a greater number of preselected discrete frequency settings are provided (for example, by making the slot 10 of the stored preset of waveforms thus producing a specialized version of the instrument for use in stroke units.

Hand Held TD-E-ONSor 2000

FIG. 20 illustrates a hand held transdermal electric ONSor (TD-E-ONSor 2000). The handheld variations comprising a stimulator body 2002 and/or the stimulator probe 2004.

The body of E-ONSor is generally cylindrical or tetragonal in shape with blunt angles grasped by a hand of a user and/or a disposable, detachable stimulator probe 2004 formed at its top end with one or two L shaped application heads 2022 and/or 2024. The stimulator body 2002 may comprise a housing 2008 with front housing, back housing, side housings and/or proximal housing, which may fit together to define a body cavity 2010. The anterior housing of the body is equipped with a user interface 2036 that allows the user to adjust different parameters of the electrical stimulus such as the frequency, amplitude, shape of waveform, etc., and/or modulating these parameters or select preset features of the stimulus. The top of anterior housing is further provided with monitor lights 2038, while top of posterior housing provided with an on/off switch 2040. The stimulating probe 2004, which may be push-fitted onto the body of the stimulator 2002 in a manner inhibiting relative movement, while at the same time a secure electrical connection between the stimulator probe 2004 and/or the body of 2002 the stimulator is ensured. The stimulator body may comprise a power source 2014 and/or control subsystem 2012 and, which together may generate and/or control the stimulus.

The stimulator probe 2004 may comprise one or two L-shaped intra-nasal application heads 2022 and/or 2024. Each intranasal application head 2022, 2024 may comprise an electrode 2016, 2018 located on the inner surface of the distal end of the application head 2022, 2024. Two or more electrodes may be spaced longitudinally along the length of the inner aspect of the long arm of L-shaped intranasal application head. The electrodes described herein may comprise any conductive materials, such as hydrogel or metals (e.g., stainless steel, titanium, platinum, or the like), conductive ceramics (e.g., titanium nitride), or the like. As shown in the cut-away view of the E-ONSor 2000 in FIG. 20, the electrodes 2016 and/or 2018 may be connected to leads 2026 and/or 2028 located within application head 2022 and/or 2024, respectively. The leads 2026 and/or 2028 may in turn be connected to connectors 2030 and/or 2032, respectively. Connectors 2030 and/or 2032 may extend through lumens in the proximal housing, and/or may connect directly or indirectly to the control subsystem 2012 and/or power source 2014. As such, the electrical stimulus may travel from the control subsystem 2012 through the connectors 2030 and/or 2032, through the leads 2026 and/or 2028, and/or through the electrodes 2016 and/or 2018 stimulating the nasal mucosa of the septum of the subject, activating TVS and/or TABRs for increasing the CBF/OBF in the brain and/or the eyes with acute dysregulated reduced CBF/OBF.

In some variations of handheld stimulators, may comprise a return contact 2020 located on the angle and/or upper surface of short arm of L shaped application head, and/or configured to be in contact with shin of nostril. The return contact might be placed on the stimulator body, and/or may be configured to be in contact with the hand of the user.

It may be desirable that the electrode 2016, 2018 have smooth rounded edges, to help minimize the risk of tissue damage during advancement of the electrode into the nose. The shape of the electrode may have spherical, ovoid or rectangular design. The electrode may have any suitable length, such as between about 3 mm and/or about 10 mm. The shape and/or size of the electrode is configured to deliver current to the nasal mucosa of the septum of the vestibule of the same side of the stroke in order to stimulate septal branch of AEN, and/or to activate TVS and/or TABRS to increase CBF and/or OBF in patients with acute cerebral and/or ocular ischemic disorders. In some instances, the impedance provided by tissue may be at least partially dependent on the presence or absence of wetting substance such as gel or natural mucous secretion of the nose.

The electrical stimulation applied to the anatomical structures generally includes a plurality of waveform parameters that define a waveform delivery of the electrical stimulus may help to treat acute brain and eye strokes by inducing an increase in CBF and or OBF, or improving the delivery of oxygen glucose, anticoagulants, hormones, humoral and/or growth factors to the brain, retina and optic nerve. These waveforms may be capable of increasing the glucose uptake and glycolysis by nerve cells in ischemic tissue as well treatment of hyperglycemia associated with brain stroke. In some variations, the stimulus is a biphasic pulse waveform, which may but need not be symmetrical. The frequency of the biphasic pulse waveform may in some variations be between 10 Hz and/or 60 Hz.

In general, the methods disclosed herein include applying electrical stimulation to an anatomical structure in the nasal region and/or extra nasal sites to activate the TVS and/or TABRs, where the electrical stimulation is defined by a plurality of waveform parameters. In some instances, the methods may comprise spatially controlling the stimulus delivery to target particular anatomical structure(s) and/or to modify the current pathways over time. The method may further include confirming activation of TVS and/or TABRs by evaluating changes of CBF and or OBF parameters using the currently available methods such as MRI, CD and/or OCT.

FIGS. 2, 3, 4 shows a general schematic draw the flow of electrical stimulation to targeted vascular tissues of the brain and ocular circulation or indirectly through the brain. Stimulating the septal branch of AEN, electrical stimulation is provided in the nasal mucosa of the septum (more preferable site of stimulation) and/or from there is transmitted to the AEN, to the nasociliary nerve to trigeminal ganglion, and/or antidromically to branches of ophthalmic nerve supplying the ophthalmic and cerebral arteries causing vasodilatation and/or decreased vascular resistance in these arteries along with increased CBF and/or OBF. In other pathway, the electrical stimulus is transmitted to brain stem, activating the superior salivatory nucleus (SSN), and/or parasympathetic system through SPG and its pos-synaptic parasympathetic nerve fibers innervating the cerebral arteries and ophthalmic artery and their branches/or causing vasodilation of cerebral arteries and ophthalmic artery and its branches leading to increased CBF/OBF.

The plurality of waveform parameters that define the stimulation waveforms may be selected from the group consisting of on/off duration, frequency, pulse width, amplitude, and/or shape. Other suitable waveform parameters may also be used.

The frequency in some of these variations ranges from about 10 to 60 Hz. In some of these variations, the frequency ranges from about 20 to 50 Hz. In some of these variations, the frequency ranges from about 30 to 40 Hz. In some variations, the frequency is 30 Hz. In some variations, the frequency is 10, 20, 40 Hz. In some variations, the frequency might be fixed or modulated over time.

In some of these variations, the on/off duration ranges from about 0.1 to 5.0 seconds on, and/or about 0.1 to 5.0 seconds off. In some of these variations, the on/off duration is 1.0 second on, and/or 1.0 second off. In some of these variations, the on/off duration is 5.0 seconds on, and/or 5.0 seconds off.

The amplitude ranges from about 0.1 to 10 mA. In some of these variations, the maximum amplitude ranges from about 1 to 3 mA. In some variations, the amplitude might be steady or variable overtime. The increase or decrease of amplitude might be gradual or abrupt. Amplitude variation may ramp up, or ramp down; it might take the sinusoidal, angular or other forms. The aim of amplitude modulation is to increase the efficiency of ONS and/or increased CBF/OBF and/or minimize the accommodation to stimulation.

A particular combination of the parameters of the waveform, its modulation over time, and/or spatial or temporal patterning may be applied using a stimulator comprising a plurality of combinations stored in memory. Selection of the stored combinations may be random, predetermined, or controlled by a user.

In some variations the methods described herein comprise applying patterned electrical stimulation to an anatomical structure intranasally or extra nasally to stimulate V1, and/or activate the TVS, and/or TABRs, thereby increasing CBF/OBF, wherein the patterned electrical stimulation comprises a biphasic waveform having cathodic and/or anodic pulse pairs. In some of these variations, the ratio of duration to amplitude for the cathodic pulse varies over time according to a saw tooth function. In some of these variations, the ratio of duration to amplitude for the cathodic pulse varies over time according to a sinusoidal function.

The frequency, peak-to-peak amplitude, and/or pulse width of the waveforms may be constant, but in some variations the stimulator may be configured to vary the frequency, amplitude, and/or pulse width of the waveform. This variation may occur according to a predetermined plan, or may be configured to occur randomly within given parameters.

In some variations, the methods described herein comprise a method for inducing increased CBF/OBF of the same side of the stroke. In some variations the method comprises delivering an electrical stimulus to a patient having acute brain and ocular ischemic disorders for example with acute reduced dysregulated OBF, wherein the electrical stimulus can be one of a plurality of preset waveforms comprising at least a first preset waveform and/or a second preset waveform, and/or changing the electrical stimulus from the first preset waveform to the second preset waveform while delivering the electrical stimulus. The electrical stimulus may be changed from the first preset waveform to the second preset waveform by the physician. In some of these variations, the applied patterned stimulation is randomly selected from the plurality of stored patterned stimulation waveforms.

In some variations, the methods described herein comprise providing a device to physicians to treat a patient having acute ischemic disorders of the brain and/or the eye, wherein the device is configured to deliver a plurality of electrical waveforms to an anatomical target in a patient. In some of these variations, the anatomical target may be the nasal mucosa. In some of these variations, the anatomical target may be the nasal bridge. In others of these variations, the anatomical target may be the forehead. In some of these variations, at least one of the plurality of waveforms may have a pulse width that varies over time. In some of these variations, the pulse width may vary over time according to an exponential function.

In some variations, the nose supported stimulators are configured for placement on the skin of the nasal bridge. The stimulators, which may for example, comprise two, four, or more active electrodes. In some variations, the systems are configured for activating cutaneous sensors or nerve fibers innervating cutaneous sensors in one side of the nose ipsilateral to that of cerebral/ocular stroke in order to avoid intracerebral vascular steal phenomenon.

In some variations, the programmable memory is capable of storing up to 10 patterned stimulation waveforms. In some variations the system further comprises a user interface for selecting one or more of the stored plurality of patterned waveforms. In some variations, the controller is configured to execute a program of those cycles through a plurality of waveform parameter options.

In some variations, the devices described herein comprise a handheld stimulator comprising a stimulator body comprising a user interface, and/or a stimulator probe comprising an application head comprising an electrode. The stimulator may be configured to deliver a plurality of electrical waveforms, and/or the user interface may be configured for selection of one of the plurality of electrical waveforms. Each of the waveforms may have at least one of a pulse shape, maximum amplitude, pulse width, or frequency that is modulated over time. In some of these variations, each of the waveforms may have at least two of a pulse shape, maximum amplitude, pulse width, or frequency that is modulated over time. In some variations, each of the waveforms has a pulse shape that is modulated over time. In some variations, the waveform comprises a first period comprising a two-phase current-controlled waveform, and/or a second period comprising a current-controlled phase followed by a voltage-controlled phase.

Ischemic brain stroke is one of the most common causes of mortality and morbidity in the world. Ischemic brain injury is accompanied by several side effects, including brain oedema, destruction of blood-brain barrier (BBB), inflammation and induction of oxidative stress. Oxidative stress in turn leads to oedema and more destruction of BBB which causes additional brain damage.

Ascorbic Acid as a Neuromodulator

Ascorbic acid is a potential antioxidant factor that can neutralize free radicals (especially hydroxyl radicals) via electron transfer, especially in brain parenchyma. It has been shown that antioxidant treatment with AA significantly reduces lipid peroxidation and increases superoxide dismutase and catalase activities. Moreover, AA is an essential antioxidant for scavenging free radicals in the brain and may protect endothelial function against the exacerbated ischemic oxidative injury. Furthermore, oxidative stress is an early trigger for the up-regulation of MMP-9 which in turn contributes to BBB damage after cerebral ischemia reperfusion. AA ameliorates the adverse affects of late r-tPA therapy because the combination of treatments decreased MMP-9 levels, BBB disruption and brain oedema. AA alone or in combination with r-tPA also showed to be neuroprotective as assessed by decreased infarct volume. Pharmacological dose of AA may act as prodrug for hydrogen peroxide ($H_2O_2$). In the presence of catalase, high concentrations of $H_2O_2$ might act as a chemical source of oxygen, especially in ischemic tissue of the brain and the eye. Oxidative stress appears to be involved in the enhanced central sympathetic outflow. There are a number of studies supporting the hypothesis that increased oxidative stress may contribute to the pathogenesis of sympathetic overactivity in a number of diseases including cerebral stroke and essential hypertension. Intravenous infusion of antioxidants is able to blunt sympathetic overactivity. Intravenous administration of AA produces substantially higher plasma concentrations than those achievable with oral administration and/or proved to achieve sympatholytic effects. Therefore, it is reasonable to postulate that intravenous administration of high dose of AA is able to induce centrally mediated sympatholytic effect.

Various embodiments and/or aspects of the present invention as delineated hereinabove and/or as claimed in the claims section below find experimental support in the following examples.

PROTOCOL OF INTRAVENOUS VITAMIN C THERAPY FOR SYMPATHOLYSIS: Intravenous Administration of 10 gm of ascorbic acid in 100 cc saline in the first day, followed by 4 g ascorbic acid by intravenous rout for the rest of treatment period during the acute stage of the stroke (1 week). The first dose of ascorbic acid is given 15 minutes prior neuromodulation session to protect against oxidative damage induced by ischemia/reperfusion and ameliorates glutamate excitotoxicity.

SETTINGS AND EXAMPLES

Reference is now made to the following examples, which together with the above descriptions illustrate some embodiments of the invention in a non-limiting fashion.

Setting 1
PROTOCOL OF INTRAVENOUS VITAMIN C THERAPY FOR SYMPATHOLYSIS
AA Treatment: For adults, Intravenous administration of AA in a dose of 3 gm dissolved in 100 ml of saline infused at 5 ml min$^{-1}$ for 20 min in the first day, followed by a drip infusion of 1 g dissolved in 100 ml daily during the rest of the treatment period. For adolescents, AA is administered intravenously in a dose of 0.045 gm per kg body weight. In the first day, and 0.015 g per kg body weight thereafter. This dose of AA is given one-hour prior neuromodulation session Setting 2
Vibrotactile ONS is delivered intranasally via intranasal application head of V-ONSor 600, nasal clip of portable V-ONS 800, and/or nasal application heads of V-ONSor 900. Extra nasal stimulation of the nasal bridge and/or forehead is delivered by portable V-ONSor 600. Vibrotactile stimulation frequency is in the range of 40 Hz-90 Hz. with on/off periods of 4 second on and/or 1 seconds off; a minimum stimulation amplitude of 1.5 μm, a maximum stimulation amplitude of 3.5 μm, a variation in stimulation amplitude of 2.0 μm, and/or an amplitude modulation frequency of 2.0 Hz, a minimum pulse width of 0 μm; a maximum pulse width of 300 μm; a pulse width modulation frequency of 1 Hz. For example, a vibrotactile ONS is applied intranasally to the ipsilateral side of the stroke for 6 minutes and for another 6 minute to extranasal sites (side of the nose and forehead) and/or the duration of whole session of vibrotactile stimulation is 12 minutes Setting 3
Vibro-chemical ONS is delivered intranasally via intranasal application head of V-Ch-ONSor 1300, The V-Ch ONSor is a bi-modular device, with one system producing vibrotactile stimulation and/or a second system stimulate V1 chemically by TRPM8 agonist using a specific micro pump for delivering the chemical agent in a pulsatile way with a frequency ranging from 0.5 Hz to 2 Hz, and/or 2 second on/13 second off. Programming of vibrotactile and/or chemical stimulation might be in the form of initial 2 second of chemical stimulation followed by 11 second of vibration stimulation, followed by 2 second off for both chemical stimulation and/or vibrational stimulation. This pattern may be repeated during the session of treatment. The setting of Vibrotactile stimulation might be chosen from any of the above-mentioned parameters for vibrotactile setting Vibro-chemical ONS is applied intranasally and at extranasal sites to the ipsilateral side of the stroke for 12 minutes Setting 4
Ultrasonic ONS is delivered intranasally via intranasal application head of US-ONS 1400. After application of coupling gel on the ultrasound probe, and/or insertion of the probe intranasally opposite the nasal septal mucosa of the vestibule, the US-ONSor 1400 is activated using the following set up; the Ultrasonic stimulation frequency is between 500 Hz to 8 Mhz, with on/off periods of 3 second on and/or 1 seconds off; a minimum ultrasound power 30 mW/cm$^2$, a maximum ultrasound power 60 mW/cm$^2$, a variation in maximum ultrasound power of 30 mW/cm$^2$, and/or an ultrasound power modulation frequency of 2.0 Hz, with average burst time of 200 μs. After application of coupling gel on the ultrasound probe, and/or insertion of the probe intranasally to the ipsilateral side of the stroke for 6 minutes Setting 5
Optical ONS is delivered intranasally via intranasal stimulation tube of O-ONSor 1500. Blue light (wavelength; 480 nm) stimulation is delivered intranasally via O-ONSor 1500. The stimulation frequency is between 10 Hz to 50 Hz, duty cycle 50%, with on/off periods of 10 second on and/or 1 second off; the minimum energy output 10 mW/cm$^2$, and/or maximum energy output 40 mW/cm$^2$. Frequency modulation is 2.0 Hz with average duration of treatment session of 5-10 minutes. The optical stimulation is delivered through the nasal vestibule of the ipsilateral side of the stroke.

Setting 6
Electrical ONS is delivered intranasally via intranasal application head of portable E-ONSor 1900, or by the use of intranasal head of the hand-held version E-ONS 2000. Extra nasal electrical stimulation of the nasal bridge and/or forehead is delivered by portable E-ONSor 1900. The electrical stimulation features include a frequency of 10 Hz-60 Hz with on/off periods of 4 second on and/or 1 seconds off; a minimum stimulation amplitude of 7.0 mA, a maximum stimulation amplitude of 3.50 mA for intranasal stimulation and rang between 1-10 mA for extra-nasal stimulation, and/or an amplitude modulation frequency of 2.0 Hz, a minimum pulse width of 0 μm; a maximum pulse width of 300 μm; a pulse width modulation frequency of 1.0 Hz. The duration of extra-nasal stimulation (nasal bridge, forehead areas in both sides) varies from 8-12 minutes. The electric ONS is applied intranasally to the ipsilateral side of the stroke for 5-10 minutes

EXAMPLES

Example 1

Intranasal Vibrotactile Stimulation: A patterned waveform of ONS is delivered intranasally, to the subjects using intranasal application head of V-ONSor 600, nasally clipped application head of portable V-ONS 800, The head of intranasal probe is introduced intranasally to come in contact of the mucosa of the nasal septum. The delivered waveform is square shaped, with frequency of 60-90 Hz, and/or amplitude of 1.5 µm-3.0 µm, with on/off periods of 4 seconds on and/or 1 second off. The session duration is 3-5 minutes on each nostril. The application head of the probe is placed in contact of nasal side ipsilateral to the side of the stroke Example 2

Nasal bridge Vibrotactile Stimulation: A patterned waveform of ONS is delivered extra-nasally, to the subjects over the side of the nose using a device as described with respect to FIG. 6, FIG. 8 FIG. 9. The application head of the probe is placed in contact of nasal side ipsilateral to the side of the stroke. The delivered waveform is square shaped, with frequency of 35 Hz, and/or amplitude of 1.5 µm-3.0 µm, with on/off periods of 4 seconds on and/or 2 seconds off. The session duration is 3 minutes Example 3

Forehead Vibrotactile Stimulation: A patterned waveform of ONS is delivered extra-nasally, to the subjects over the forehead in one or both sides using a device as described with respect to FIG. 6, FIG. 9. The flat-topped shaped head of the probe is placed in contact of skin of the forehead of the ipsilateral side of the stroke. The delivered waveform is square shaped, with frequency of 35 Hz, and/or amplitude of 1.5 µm-3.0 µm, with on/off periods of 4 seconds on and/or 2 seconds off. The session duration is 3 minutes.

Example 4

Intranasal Vibro-chemical Stimulation: A patterned waveform of ONS is delivered intranasally, to the subjects using intranasal application head of V-Ch-ONSor 1300. The head of intranasal probe is introduced intranasally to come in contact of the mucosa of the nasal septum. The chemical stimulation might be adjusted regarding timing of stimulation, on/off and/or frequency of injection. For example, the micro pump is delivering the chemical agent for example 2% menthol in a pulsatile way with a frequency ranging from 0.5 Hz to 2 Hz, and/or 2 second on/13 second off. Programming of vibrotactile and/or chemical stimulation might be in the form of initial 2 second of chemical stimulation followed by 11 second of vibrotactile stimulation, followed by 2 second off for both chemical stimulation and/or vibrotactile stimulation. This pattern can be repeated over the session of treatment. The application head of the probe is placed in contact of nasal side ipsilateral to the side of the stroke Example 5

Intranasal ultrasonic ONS: A patterned waveform of ultrasonic ONS is delivered intranasally, to the subjects using a device as described with respect to FIGS. 14,A-B. A gel is applied to the head of intranasal probe and is introduced intranasally to come in contact of the mucosa of the nasal septum. The delivered waveform is square shaped, with a frequency between 500 Hz to 8 Mhz, with on/off periods of 3 second on and/or 1 seconds off; a minimum ultrasound power 30 mW/cm$^2$, a maximum ultrasound power 60 mW/cm$^2$, a variation in maximum ultrasound power of 30 mW/cm$^2$, and/or an ultrasound power modulation frequency of 2.0 Hz, with average burst time of 200 µs. The session duration is 6 minutes per nostril.

Example 6

Intranasal optical blue light Stimulation: A patterned waveform of ONS is delivered intranasally to the subjects using a device as described with respect to FIGS. 15A-B. Semiconductor light emitting diode (LED) is the Light source with Wavelength: 480 nm (blue light), and/or energy output: 10 mW/cm$^2$ to 40 mW/cm$^2$ using a pulse mode of 40 Hz at 50% duty cycle. The stimulating tube is introduced intranasally ipsilateral to the side of the stroke and/or self supported by a mean of clipping to the lateral nasal wall. A 5-10 minutes session per nostril is delivered 6 hourly in the acute stage of the stroke for one week.

Example 7

Intranasal hybrid electro-optical ONS: A patterned waveform of electrical ONS is delivered intranasally to the subjects using a device HEOp-ONSor 1700 as described with respect to FIGS. 17A-B. Preconditioning of the AEN is configured to be performed using subthreshold electrical stimulus of less than 1.0 mA to less than 3.0 mA. Semiconductor light emitting diode (LED) is the Light source with Wavelength: 480 nm (blue light), and/or subthreshold energy output: less than 10 mW/cm$^2$ to less than 40 mW/cm$^2$. Both electrical and optical stimulation are delivered simultaneously in a pulse mode of 40 Hz at 50% duty cycle. The application head is introduced intranasally ipsilateral to the side of the stroke and/or self supported by a mean of clipping to the lateral nasal wall. A 3-6 minutes session per nostril is delivered hourly during the first 6 hours and 3 hourly thereafter in the acute stage of the stroke (one week).

Example 8

Intranasal electric ONS: Stimulation: A patterned waveform of electric ONS is delivered intranasally to the subjects using a device as described with respect to FIGS. 17,18A-B and 19. Different Intranasal application head might be used to deliver intranasal electric ONS to one or both nostrils. Electrical stimulation frequency of 10 Hz-60 Hz with on/off periods of 4 second on and/or 1 seconds off; a minimum stimulation amplitude of 1.0 mA, a maximum stimulation amplitude of 10.0 mA, a variation in stimulation amplitude of 9.0 mA, and/or an amplitude modulation frequency of 2.0 Hz as shown in Table 10. The intranasal head 1800 is configured to be held in place by nasal clip for an extended period of time (therapeutic time) without undue effort or discomfort, due to the lightweight, portable design of the device. The application head is introduced intranasally ipsilateral to the side of the stroke and/or self supported by a mean of clipping to the lateral nasal wall. A 3-6 minutes session per nostril is delivered hourly during the first 6 hours and 3 hourly thereafter in the acute stage of the stroke (one week).

Example 9

Treatment Protocol for Ischemic Cerebral Stroke

As soon as the ischemic cerebral stroke is established by clinical, laboratory and radiological investigations the following protocol is delivered during the acute stage of the stroke (1 week).

Pharmacological dose of ascorbic acid given by intravenous rout in a dose of 10 grams of ascorbic acid dissolved in 100 cc normal saline in the first day, and 4 gram daily for the rest of the treatment period during the acute stage of the stroke (1 week).

A patterned modulated waveform of vibrotactile ONS is delivered intranasally to the subjects. The delivered waveform is square shaped, with modulated frequency and/or amplitude. The session duration is 6 minutes delivered into the nostril of the ipsilateral side of the stroke. Intranasal Vibrotactile ONS is given hourly (as a part of vibrochemical ONS) during the first 6 hours and 3 hourly thereafter.

A patterned waveform of vibrotactile ONS is delivered extra-nasally, to the subjects using a flat-topped shaped application head. The delivered waveform is square shaped, with modulated frequency and/or amplitude. The session duration is 6 minutes delivered to the side of the nose and the forehead of the ipsilateral side of the stroke. Extranasal Vibrotactile ONS is given hourly during the first 6 hours and 3 hourly thereafter.

Vibro-chemical ONS is delivered intranasally via intranasal application head of V-Ch-ONSor 1100. One system producing vibrotactile stimulation and/or a second system stimulate V1 chemically using TRPM8 agonist via a specific micro pump delivering a chemical agent such as 2% of menthol in a pulsatile way with a frequency ranging from 0.5 Hz to 2 Hz, and/or 2 second on/13 second off. Programming of vibrotactile and/or chemical stimulation might be in the form of initial 2 second of chemical stimulation followed by 11 second of vibrotactile stimulation, followed by 2 second off for both chemical stimulation and/or vibrational stimulation. This pattern may be repeated during the session of intranasal vibrotactile treatment (6 minutes). The setting of intranasal Vibrotactile stimulation might be chosen from any of the above-mentioned settings. Vibrochemical stimulation of V1 is given 6 hourly during the acute stage (1 week) and once daily during the sub acute or chronic stage of rehabilitation wherein the ONS is delivered to the nostril of ipsilateral side of the stroke.

Intranasal optical blue light Stimulation: A patterned waveform of ONS is delivered intranasally to the subjects using a device as described with respect to FIGS. 15, 16. Semiconductor light emitting diode (LED) is the light source with Wavelength: 480 nm (blue light), and/or energy output: 10 mW/cm$^2$ to 100 mW/cm$^2$, using a pulse mode of 40 Hz at 50% duty cycle. The stimulating tube is introduced intranasally ipsilateral to the side of the stroke and/or self supported by a mean of clipping to the lateral nasal wall. A 10 minutes session per nostril is delivered 6 hourly in the acute stage of the stroke (1 week).

Intermittent normobaric oxygen for 15 minutes every hour alternating with 45 minutes of breathing room air for 3 days.

Example 10

Treatment of Central Retinal Artery Occlusion (CRAO)

CRAO is an ocular emergency and is the ocular analogue of cerebral stroke. It results in profound, usually monocular vision loss, and is associated with significant functional morbidity. The incidence of acute CRAO is estimated at 8.5 in 100,000 people. It is typically produces severe and irreversible vision loss in the affected eye, with 92% of patients left with poor visual acuity of counting fingers or less, and only 8% may experience improvement. Despite significant advances in our understanding of the pathophysiology and management of this serious condition, to date, there are no drugs that have shown to improve patient outcomes significantly. As soon as CRAO is established by ophthalmic examination and fundoscopy the following protocol is delivered during the acute stage of the retinal stroke (3-4 days).

Pharmacological dose of ascorbic acid given by intravenous rout in a dose of 5 grams of ascorbic acid dissolved in 100 cc normal saline in the first day, and 2 gram daily for the rest of the treatment period during the acute stage of the stroke (3-4 days).

A patterned modulated waveform of vibrotactile ONS is delivered intranasally to the subjects. The delivered waveform is square shaped, with modulated frequency and/or amplitude. The session duration is 6 minutes delivered into the nostril of the ipsilateral side of the eye with a stroke. Intranasal Vibrotactile ONS is given hourly (as a part of vibrochemical ONS) during the first 6 hours and 3 hourly thereafter.

A patterned waveform of vibrotactile ONS is delivered extra-nasally, to the subjects using a flat-topped shaped application head. The delivered waveform is square shaped, with modulated frequency and/or amplitude. The session duration is 6 minutes delivered to the side of the nose and the forehead of the ipsilateral side of the eye with a stroke. Extranasal Vibrotactile ONS is given hourly during the first 6 hours and 3 hourly thereafter.

Vibro-chemical ONS is delivered intranasally via intranasal application head of V-Ch-ONSor 1100. One system producing vibrotactile stimulation and/or a second system stimulate V1 chemically using TRPM8 agonist via a specific micro pump delivering a chemical agent such as 2% of menthol in a pulsatile way with a frequency ranging from 0.5 Hz to 2 Hz, and/or 2 second on/13 second off. Programming of vibrotactile and/or chemical stimulation might be in the form of initial 2 second of chemical stimulation followed by 11 second of vibrotactile stimulation, followed by 2 second off for both chemical stimulation and/or vibrational stimulation. This pattern may be repeated during the session of intranasal vibrotactile treatment (6 minutes). The setting of intranasal Vibrotactile stimulation might be chosen from any of the above-mentioned setting. Vibrochemical stimulation of V1 is given 6 hourly during the acute stage (1 week) and once daily during the sub acute or chronic stage of rehabilitation wherein the ONS is delivered to the nostril of ipsilateral side of the stroke.

Intranasal optical blue light Stimulation: A patterned waveform of ONS is delivered intranasally to the subjects using a device as described with respect to FIGS. 15, 16. Semiconductor light emitting diode (LED) is the Light source with Wavelength: 480 nm (blue light), and/or energy output 10 mW/cm² to 100 mW/cm², using a pulse mode of 40 Hz at 50% duty cycle. The stimulating tube is introduced intranasally ipsilateral to the side of the stroke and/or self supported by a mean of clipping to the lateral nasal wall. A 10 minutes session per nostril is delivered 6 hourly in the acute stage of the stroke (1 week).

Intermittent normobaric oxygen for 15 minutes every hour alternating with 45 minutes of breathing room air for 3 days.

While the preceding description contains much specificity, these should not be construed as limitations on the scope of the invention, but rather as an exemplification of a preferred embodiment and/or additional embodiments. Many other variations are possible.

Skilled artisans will readily be able to change dimensions, shapes and/or construction materials of the various components described in the embodiment. Accordingly, the scope of the invention should be determined not by the embodiment illustrated, but by the appended claims and/or their legal equivalents.

The various embodiments described above are provided by way of illustration only and/or should not be construed to limit the invention. Based on the above discussion and/or illustrations, those skilled in the art will readily recognize that various modifications and/or changes may be made to the present invention without strictly following the exemplary embodiments and/or applications illustrated and/or described herein. Such modifications and/or changes do not depart from the true spirit and/or scope of the present invention It is expected that during the life of a patent maturing from this application many relevant technologies will be developed and/or the scope of the terms are intended to include all such new technologies a priori. As used herein the term "about" refers to ±10%

The terms "comprises", "comprising", "includes", "including", "having" and/or their conjugates mean "including but not limited to".

The term "consisting of" means "including and/or limited to".

The term "consisting essentially of" means that the composition, method or structure may include additional ingredients, steps and/or parts, but only if the additional ingredients, steps and/or parts do not materially alter the basic and/or novel characteristics of the claimed composition, method or structure.

As used herein, the singular form "a", "an" and/or "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and/or brevity and/or should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and/or 6. This applies regardless of the breadth of the range.

Whenever a numerical range is indicated herein, it is meant to include any cited numeral (fractional or integral) within the indicated range. The phrases "ranging/ranges between" a first indicate number and/or a second indicate number and/or "ranging/ranges from" a first indicate number "to" a second indicate number are used herein interchangeably and/or are meant to include the first and/or second indicated numbers and/or all the fractional and/or integral numerals there between.

As used herein the term "method" refers to manners, means, techniques and/or procedures for accomplishing a given task including, but not limited to, those manners, means, techniques and/or procedures either known to, or readily developed from known manners, means, techniques and/or procedures by practitioners of the chemical, pharmacological, biological, biochemical and/or medical arts.

As used herein, the term "treating" includes abrogating, substantially inhibiting, slowing or reversing the progression of a condition, substantially ameliorating clinical or aesthetical symptoms of a condition or substantially inhibiting the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and/or variations will be apparent to those skilled in the art. Accordingly, it is intended to embrace all such alternatives, modifications and/or variations that fall within the spirit and/or broad scope of the appended claims.

All publications, patents and/or patent applications mentioned in this specification are herein incorporated in their entirety by reference into the specification, to the same extent as if each individual publication, patent or patent application was specifically and/or individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for treatment of acute ischemic disorders of at least one of the brain and the eye comprising:
   repeated application of non-invasive ophthalmic nerve stimulation (ONS); and
   administration of pharmacological doses of at least of a sympatholytic agent and an anti-oxidant within 3-24 hours from an onset of the acute ischemic disorder, wherein an effective amount of ONS is administered to a subject in need thereof.

2. The method of claim 1, wherein said administration includes a pharmacological dose of ascorbic acid.

3. The method of 25a, wherein said administration is intravenous.

4. The method of claim 1, wherein the acute ischemic disorder is selected from the group comprising anterior cerebral artery occlusion, middle cerebral artery occlusion, posterior cerebral artery occlusion, basilar artery occlusion, ophthalmic artery occlusion, central retinal artery occlusion (CRAO), branch retinal artery occlusion (BRAO), posterior ciliary artery occlusion and anterior ciliary artery occlusion.

5. The method of claim 1, wherein the ONS is applied to branches of an ophthalmic nerve intranasally or at extranasal sites at a nasal bridge, supraorbital region and upper eyelids, wherein the stimulated branches of the ophthalmic nerve comprise anterior ethmoid nerve (AEN), supra-orbital nerve supra-trochlear nerve, infratrochlear nerve, branches of nasociliary and frontal nerves.

6. The method of claim 5, wherein the ophthalmic nerve of a same side of a stroke is stimulated mechanically using a vibrotactile signal, wherein a portable vibrotactile ophthalmic nerve stimulator device with appropriate application heads is used to deliver a modulated, low magnitude, high frequency vibrotactile stimulus to activate ophthalmic nerve in at least one of an intranasal site and an extranasal site, wherein the stimulus has a frequency of 40 Hz-90 Hz, amplitude of 2-5 μm for 10-15 minutes per session.

7. The method of claim 5, wherein the ophthalmic nerve of a same side of the stroke is stimulated mechanically using ultrasonic signal, wherein a portable ultrasonic ophthalmic nerve stimulator device with an intranasal application head is used to deliver a modulated ultrasonic stimulus with a frequency between 500 Hz to 8 Mhz, with an average burst time of 200 μs for 10-15 minutes per session.

8. The method of claim 5, wherein the ophthalmic nerve of a same side of the stroke is stimulated chemically via stimulation ophthalmic nerve fibers expressing Transient receptor potential cation channel subfamily M member 8 (TRPM8) using an automated micro-pump incorporated within an intranasal application head, wherein a content of a reservoir of said pump is released through multiple irrigation holes located at said application head in a pulsatile controlled fashion for stimulation of the anterior ethmoid nerve.

9. The method of claim 8, wherein a reservoir of intranasal application head of chemical ophthalmic nerve stimulator is loaded with a composition comprising a pharmacologically effective amount of a TRPM8 agonist selected from the group comprising menthol, icilin, eucalyptol, 1-diisopropylphosphoryl nonane, menthoxypropanediol, geraniol, hydroxycitronellal, linalool, N-ethyl-5-methyl-2-propan-2-ylcyclohexane-1-carboxamide, and N,2,3-trimethyl-2-propan-2-ylbutanamide.

10. The method of claim 5, wherein the ophthalmic nerve of a same side of stroke is activated intranasally by a modulated electrical or optical stimulus with a threshold amplitude or by a hybrid electro-optical stimulus comprising a combination of subthreshold electrical and optical stimuli to generate nerve action potential selectively on unmyelinated C nerve fibers expressing substance P (SP) and calcitonin gene reacting protein (CGRP) of the anterior ethmoid nerve.

11. The method of claim 5, wherein the ophthalmic nerve of a same side of the stroke is stimulated intranasally via a red or near infrared light with a wavelength between 630-820 nm, using an appropriate self-supported light emitting application head of an optical or electro-optical ophthalmic nerve stimulator, with a minimum energy output 10 mW/cm$^2$, and a maximum energy output of 40 mW/cm$^2$, with a stimulus frequency is between 10 Hz to 50 Hz for 10-15 minutes per session.

12. The method of claim 5, wherein melanopsin containing nerve fibers of the ophthalmic nerve are stimulated intranasally via a blue light with a wavelength of 480 nm using an appropriate self-supported light emitting application head of an optical or electro-optical ophthalmic nerve stimulator, wherein an energy output range is between 10 mW/cm$^2$ to 40 mW/cm$^2$, with a stimulus frequency between 10 Hz to 50 Hz for 10-15 minutes per session.

13. The method of claim 5, wherein the ophthalmic nerve of a same side of the stroke is stimulated by an electrical stimulus intranasally, wherein the stimulus is delivered to a subject via a plurality of electrodes located in an application head of an electrical ophthalmic nerve stimulator or electro-optical ophthalmic nerve stimulator, wherein the stimulator is configured to deliver a modulated pulse-based electrical waveform, with a frequency between 15 and 50 Hz, amplitude between 7/10 mA to 35/10 mA for intranasal stimulation and rang between 1 to 10 mA for extranasal stimulation for 10-15 minutes per session.

14. The method of claim 5, wherein the ophthalmic nerve of the subject is stimulated intranasally by a hybrid electro-optical stimulus by providing an electrical sensitizing stimulation signal combined with an optical stimulation signal applied in temporal proximity to trigger a desired nerve action potential NAP to selectively activate substance P SP and calcitonin gene reacting protein CGRP containing nerve fibers of the anterior ethmoid nerve for 10-15 minutes per session.

15. The method of claim 1, wherein said ONS is administered hourly in a first 6 hours, and once every 3 hours thereafter during an acute stage of the acute ischemic disorder, one every 6 hours during a sub-acute stage of the acute ischemic disorder and once daily during a rehabilitative stage of the acute ischemic disorder, once or twice daily or more when needed as a re-treatment for recurrent acute ischemic disorder.

16. The method of claim 2, wherein a first regime of the ascorbic acid is administered intravenously in a loading dose of 50-100 mg/kg of the subject in the first day.

17. The method of claim 6, wherein said first regime is followed by 25-50 mg/kg body weight as a daily maintenance dose thereof over a period of time during the acute stage, wherein the ascorbic acid is dissolved in 100 ml of saline and infused at 5 ml min$^{-1}$ for 20 minutes.

* * * * *